United States Patent
Gunasekar et al.

(10) Patent No.: US 11,622,709 B2
(45) Date of Patent: Apr. 11, 2023

(54) HEADSET AND ELECTRODES FOR SENSING BIOELECTRICAL POTENTIAL AND METHODS OF OPERATION THEREOF

(71) Applicant: Zeto, Inc., Santa Clara, CA (US)

(72) Inventors: Aswin K. Gunasekar, Santa Clara, CA (US); Christopher Bramley Fruhauf, San Anselmo, CA (US); Florian Strelzyk, Cary, NC (US)

(73) Assignee: Zeto, Inc., Santa Clara, CA (US)

( * ) Notice: Subject to any disclaimer, the term of this patent is extended or adjusted under 35 U.S.C. 154(b) by 406 days.

(21) Appl. No.: 16/844,360

(22) Filed: Apr. 9, 2020

(65) Prior Publication Data
US 2020/0237249 A1 Jul. 30, 2020

Related U.S. Application Data

(63) Continuation of application No. PCT/US2018/063367, filed on Nov. 30, 2018.
(Continued)

(51) Int. Cl.
*A61B 5/291* (2021.01)
*A61B 5/00* (2006.01)
*A61N 1/05* (2006.01)

(52) U.S. Cl.
CPC ............ *A61B 5/291* (2021.01); *A61B 5/4094* (2013.01); *A61B 5/6803* (2013.01);
(Continued)

(58) Field of Classification Search
CPC ..... A61B 5/291; A61B 5/4094; A61B 5/6803; A61B 2562/0209; A61B 2562/14; A61B 5/256; A61B 5/25
See application file for complete search history.

(56) References Cited

U.S. PATENT DOCUMENTS

| 2,426,958 A | 9/1947 | Ulett et al. |
| 2,549,836 A | 4/1951 | McIntyre et al. |

(Continued)

FOREIGN PATENT DOCUMENTS

| CN | 205144580 | 4/2015 |
| CN | 104618830 | 5/2015 |

(Continued)

OTHER PUBLICATIONS

Dao, Phuong T. et al., "Lossy compression techniques for EEG signals," *2015 International Conference on Advanced Technologies for Communications (ATC)*, IEEE, pp. 154-159, 2015.

(Continued)

*Primary Examiner* — Paula J Stice
(74) *Attorney, Agent, or Firm* — Levine Bagade Han LLP

(57) ABSTRACT

Disclosed are medical devices for sensing bioelectrical potential including an electroencephalography (EEG) headset, electrodes compatible therewith, and methods of operation thereof. The headset can comprise a left junction and a right junction, a plurality of length-adjustable bands connecting the left junction and the right junction, and a number of electrodes. Each of the electrodes can comprise an electrode body coupled to one of the plurality of length-adjustable bands and a detachable electrode tip configured to be detachably coupled to the electrode body. The electrode tip can comprise an electrode tip body, one or more deflectable electrode legs coupled to the electrode tip body, and a conductive cushioning material coupled to a segment of at least one of the one or more electrode legs. The conductive cushioning material can retain or be saturated with one or more conductors.

13 Claims, 30 Drawing Sheets

Related U.S. Application Data

(60) Provisional application No. 62/593,819, filed on Dec. 1, 2017.

(52) U.S. Cl.
CPC ......... *A61N 1/0529* (2013.01); *A61N 1/0534* (2013.01); *A61B 2562/0209* (2013.01); *A61B 2562/14* (2013.01)

(56) References Cited

U.S. PATENT DOCUMENTS

| | | |
|---|---|---|
| 3,735,753 A | 5/1973 | Pisarski |
| 3,998,213 A | 12/1976 | Price |
| 4,112,941 A | 9/1978 | Larimore |
| 4,638,807 A | 1/1987 | Ryder |
| 4,640,290 A | 2/1987 | Sherwin |
| 4,669,479 A | 6/1987 | Dunseath, Jr. |
| 4,683,892 A | 8/1987 | Johansson |
| 4,709,702 A | 12/1987 | Sherwin |
| 4,967,038 A | 10/1990 | Gevins et al. |
| 5,042,498 A | 8/1991 | Dukes |
| 5,169,380 A | 12/1992 | Brennan |
| 5,800,351 A | 9/1998 | Mann |
| 6,510,333 B1 | 1/2003 | Licata et al. |
| 6,636,754 B1 | 10/2003 | Baura et al. |
| 6,755,795 B2 | 6/2004 | Marmaropoulos et al. |
| 6,757,556 B2 | 6/2004 | Gopinathan et al. |
| 6,807,438 B1 | 10/2004 | Brun Del Re et al. |
| 6,842,636 B2 | 1/2005 | Perrault et al. |
| 6,968,575 B2 | 11/2005 | Durocher |
| 6,973,344 B2 | 12/2005 | Finneran et al. |
| 7,173,437 B2 | 2/2007 | Hervieux et al. |
| 7,174,575 B1 | 2/2007 | Scherer |
| 7,231,723 B1 | 6/2007 | O'Neill et al. |
| 8,326,396 B2 | 12/2012 | Picht et al. |
| 8,548,554 B2 | 10/2013 | Popescu et al. |
| 9,050,451 B2 | 6/2015 | Van Der Beek et al. |
| 9,237,857 B2 | 1/2016 | Guger et al. |
| 10,660,572 B2 | 5/2020 | Gunasekar et al. |
| 10,799,180 B2 | 10/2020 | Gunasekar et al. |
| 11,160,502 B2 | 11/2021 | Gunasekar et al. |
| 11,160,505 B2 | 11/2021 | Gunasekar et al. |
| 11,166,673 B2 | 11/2021 | Gunasekar et al. |
| 11,432,757 B2 | 9/2022 | Gunasekar et al. |
| 11,432,770 B2 | 9/2022 | Gunasekar et al. |
| 2002/0057850 A1 | 5/2002 | Sirohey et al. |
| 2002/0188216 A1 | 12/2002 | Kayyali et al. |
| 2003/0083584 A1 | 5/2003 | Yonce |
| 2005/0107716 A1 | 5/2005 | Eaton et al. |
| 2005/0197556 A1 | 9/2005 | Stoler |
| 2007/0225585 A1 | 9/2007 | Washbon et al. |
| 2009/0259137 A1 | 10/2009 | Delic et al. |
| 2009/0270745 A1 | 10/2009 | Sankai |
| 2010/0198042 A1 | 8/2010 | Popescu et al. |
| 2011/0040202 A1 | 2/2011 | Luo et al. |
| 2011/0066020 A1 | 3/2011 | Svojanovsky |
| 2011/0112418 A1 | 5/2011 | Field et al. |
| 2011/0237923 A1 | 9/2011 | Picht et al. |
| 2012/0143020 A1 | 6/2012 | Bordoley et al. |
| 2013/0097086 A1 | 4/2013 | Dala et al. |
| 2014/0051044 A1 | 2/2014 | Badower et al. |
| 2014/0088394 A1 | 3/2014 | Sunderland |
| 2014/0276183 A1 | 9/2014 | Badower |
| 2014/0324146 A1* | 10/2014 | Muller ................ A61N 1/0456 607/139 |
| 2015/0005608 A1 | 1/2015 | Evans et al. |
| 2015/0126846 A1 | 5/2015 | Jia et al. |
| 2015/0141788 A1* | 5/2015 | Chi ....................... A61B 5/291 600/383 |
| 2015/0182165 A1 | 7/2015 | Miller et al. |
| 2015/0282731 A1 | 10/2015 | Hill et al. |
| 2015/0282760 A1 | 10/2015 | Badower et al. |
| 2015/0313496 A1 | 11/2015 | Connor |
| 2016/0174859 A1 | 6/2016 | Oudenhoven et al. |
| 2017/0011210 A1 | 1/2017 | Cheong et al. |
| 2017/0035317 A1 | 2/2017 | Jung et al. |
| 2017/0258400 A1 | 9/2017 | Jovanovic et al. |
| 2017/0325724 A1 | 11/2017 | Wang et al. |
| 2018/0153470 A1 | 6/2018 | Gunasekar et al. |
| 2019/0274568 A1 | 6/2019 | Shahdoostfard et al. |
| 2020/0245942 A1 | 8/2020 | Gunasekar et al. |
| 2020/0245943 A1 | 8/2020 | Gunasekar et al. |
| 2020/0281527 A1 | 9/2020 | Gunasekar et al. |
| 2020/0397375 A1 | 12/2020 | Gunasekar et al. |
| 2022/0015701 A1 | 1/2022 | Gunasekar et al. |
| 2022/0022813 A1 | 1/2022 | Gunasekar et al. |

FOREIGN PATENT DOCUMENTS

| | | |
|---|---|---|
| CN | 205081913 | 3/2016 |
| CN | 106061375 | 10/2016 |
| EP | 3547912 | 4/2017 |
| JP | H0258410 U | 4/1990 |
| WO | WO 2008/056309 | 5/2008 |
| WO | WO 2014/169241 | 10/2014 |
| WO | WO 2018/102825 | 6/2018 |
| WO | WO 2019/108968 | 6/2019 |

OTHER PUBLICATIONS

Capurro, Ignacio et al., "Efficient Sequential Compression of Multichannel Biomedical Signals," *IEEE Journal of Biomedical and Health Informatics*, IEEE, vol. 21, No. 4, pp. 904-916, Jul. 2017, Piscataway, NJ.

Mullen, Tim R. et al., "Real-Time Neuroimaging and Cognitive Monitoring Using Wearable Dry EEG," IEEE Transactions on Bioledical Engineering, vol. 62, No. 11, pp. 2553-2567, 2015.

* cited by examiner

SECTION G-G

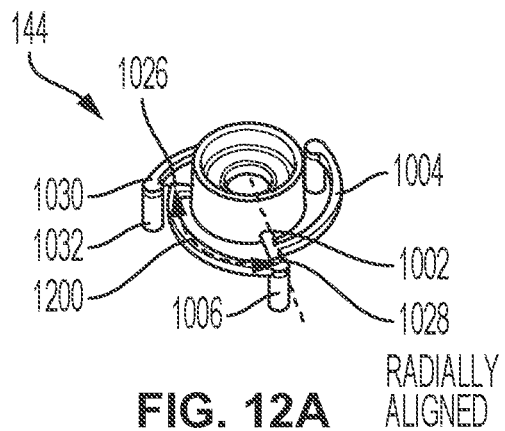
FIG. 12A RADIALLY ALIGNED
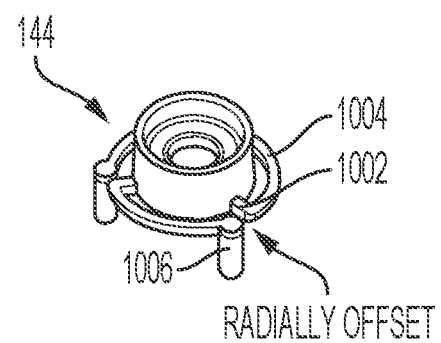
RADIALLY OFFSET
FIG. 12B
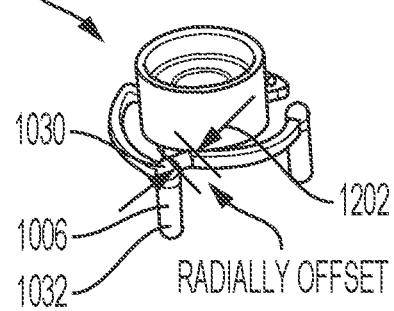
RADIALLY OFFSET
FIG. 12C
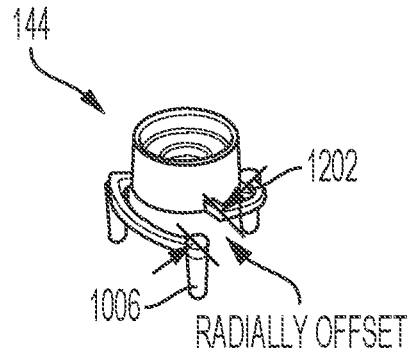
RADIALLY OFFSET
FIG. 12D

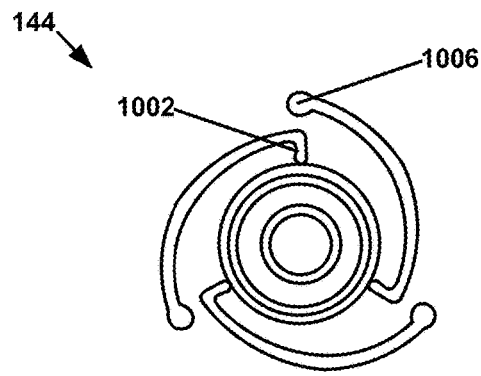
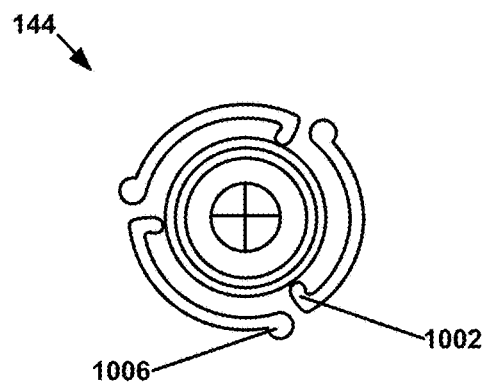
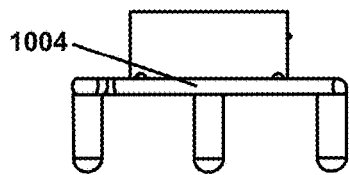
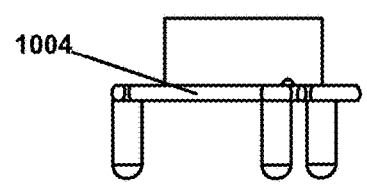
FIG. 13A  FIG. 13B
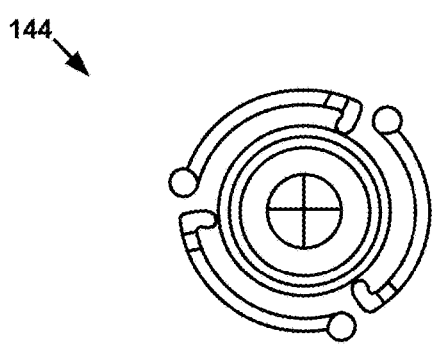
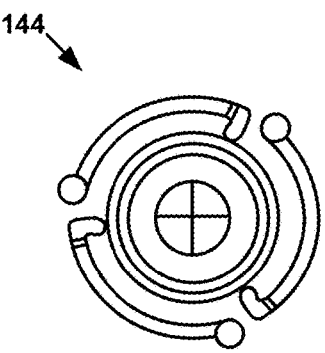
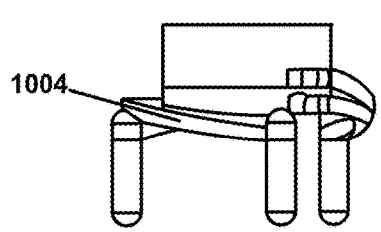
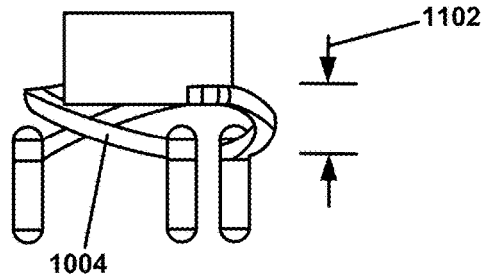
FIG. 14A  FIG. 14B

HEADSET AND ELECTRODES FOR SENSING BIOELECTRICAL POTENTIAL AND METHODS OF OPERATION THEREOF

CROSS-REFERENCE TO RELATED APPLICATION

This application is a continuation of International Application No. PCT/US2018/063367 filed Nov. 30, 2018, which claims the benefit of U.S. Provisional Application No. 62/593,819 filed on Dec. 1, 2017, both of which are incorporated herein by reference in their entireties.

TECHNICAL FIELD

The present disclosure relates generally to medical devices for sensing bioelectrical potential; more specifically, to an electroencephalography (EEG) headset, electrodes compatible therewith, and methods of operation thereof.

BACKGROUND

An electrocephalogram is a non-invasive test that detects and evaluates the electrical activity of the brain of a patient that provides information concerning the health and well-being of the patient's brain and brain functions. The test can be used to diagnose conditions such as epilepsy, seizures, head injuries including traumatic brain injuries, headaches, brain tumors, and certain sleep disorders. Conventional methods and apparatus used for conducting an electrocephalogram involve placing a number of conductive electrodes (usually metal discs or plates) on the scalp of a patient and applying a wet gel in between the electrode and skin surface. However, the use of such a gel—especially when applied to a patient's scalp populated by hair follicles—is often messy, time-consuming to apply and clean-up, and inconvenient when EEG measurements must be taken repeatedly or at regular intervals.

While so-called dry electrodes not requiring gels are gaining popularity in clinical and laboratory facilities, such electrodes also suffer from various drawbacks and limitations. Since EEG headgear often place electrodes over areas of a patient's head covered extensively by hair, the strength and quality of bioelectrical signals obtained using dry electrodes can be severely impeded when the tips of such dry electrodes do not make sufficient contact with the patient's scalp. While the design of such dry electrodes has been altered to allow the electrode tips to push through strands of hair to the patient's bare scalp, such electrodes often require a piece of headgear to be worn tightly around the patient's head, which can cause discomfort and reduce the patient's willingness to wear the headgear for long period of time. Moreover, since such dry electrodes are often made of a hard or rigid material, such electrodes can cause minor lacerations or bruising that further reduces the comfort level of such equipment.

As a result of the above limitations and restrictions, there is a need for an improved headset and electrodes for effectively and comfortably sensing bioelectrical potential and taking EEG measurements. Such a solution should be cost-effective and address the shortcomings of traditional headsets and electrodes.

SUMMARY

Disclosed are medical devices for sensing bioelectrical potential including an electroencephalography (EEG) headset, electrodes compatible therewith, and methods of operation thereof. In one aspect, an electrode tip for sensing bioelectrical potential is disclosed. The electrode tip can comprise an electrode tip body, one or more electrode legs coupled to the electrode tip body, and a conductive cushioning material coupled to a segment of at least one of the one or more electrode legs. The conductive cushioning material can retain or be saturated with one or more conductors. The electrode tip body and the one or more electrode legs can comprise or be made in part of a conductive material.

The conductive cushioning material can be a cured polymeric material. For example, the conductive cushioning material can be a hydrogel. In some instances, the conductive cushioning material can also be a crystallized hydrogel. The hydrogel can be cured by ultraviolet (UV) radiation. The hydrogel can comprise glycerin. The hydrogel can be coated on to a segment of at least one of the one or more electrode legs by dip-coating. The hydrogel can also be coupled to a segment of at least one of the one or more electrode legs by mold casting. The hydrogel can retain or be saturated with one or more conductors.

The conductive cushioning material can also be a foam saturated or infused with the one or more conductors. The conductive cushioning material can be an absorbent cotton padding saturated or infused with the one or more conductors. The conductive cushioning material can be a conductive sponge saturated or infused with the one or more conductors. The one or more conductors can comprise at least one of carbon, metal chlorides, conductive ions, and conductive nanoparticles. The conductive cushioning material can be non-residue-forming such that residue is not left on a skin surface of the patient.

The conductive cushioning material can have a maximum thickness ranging from about 0.05 mm to about 2.5 mm as measured from an exterior surface of an electrode leg. The conductive cushioning material can comprise a cushion distal end. Each of the one or more electrode legs can comprise a leg distal end. The cushion distal end can extend beyond the legal distal end such that the cushion distal end is vertically inferior to the leg distal end.

The conductive cushioning material can be ovoid-shaped. The conductive cushioning material can be substantially spherical-shaped.

The conductive cushioning material can have a cushion height as measured from a cushion proximal end to a cushion distal end. The electrode leg coated or covered by the conductive cushioning material can comprise an uncovered segment. In some instances, a height of the uncovered segment can be greater than the cushion height. In other instances, the height of the uncovered segment can be less than the cushion height.

The electrode legs can be deflectable such that the electrode legs have a non-biased configuration and a splayed configuration. Each of the electrode legs can have a leg longitudinal axis. The leg longitudinal axes of the electrode legs can be substantially parallel to one another when the two or more electrode legs are in the non-biased configuration. The leg longitudinal axes of the electrode legs can be substantially non-parallel to one another when the two or more electrode legs are in the splayed configuration.

Each of the one or more electrode legs can be an elongate rod having a leg diameter. The electrode tip body can be a cylindrical body having a tip body diameter. A ratio of the leg diameter to the tip body diameter can be between about 1:2 and 1:10.

The electrode tip can further comprise one or more electrode arms. At least one of the one or more electrode arms can couple at least one of the electrode legs to the electrode tip body. The one or more electrode arms comprise or be made in part of a conductive material.

The one or more electrode arms can curve along a spiral pattern or trajectory. Each of the one or more electrode arms can curve in at least one of a clockwise or left-handed rotational direction and a counterclockwise or right-handed rotational direction. Each of the electrode arms can comprise a proximal arm end and a distal arm end. Each of the one or more electrode arms can curve along a pitched or descending helical trajectory such that the distal arm end is vertically lower or below the proximal arm end.

The electrode tip can further comprise one or more lateral struts extending radially from the electrode tip body. At least one of the one or more lateral struts can couple at least one of the one or more electrode arms to the electrode tip body. The one or more lateral struts can comprise or be made in part of a conductive material. The electrode tip body can have a substantially circular transverse cross-section. A plurality of lateral struts can be coupled to the electrode tip body at positions arranged uniformly or equidistantly around a circumference of the electrode tip body.

The electrode tip body can comprise a cup-shaped portion surrounding a hollow center. A ferromagnetic component can be encased within a portion of the electrode tip body in proximity to a bottom surface of the cup-shaped portion. The cup-shaped portion can be configured to couple to and surround at least part of a ferromagnetic element of an electrode coupled to an EEG headset. The ferromagnetic component can be a permanent magnet. The ferromagnetic component can also be a ferromagnetic metal.

Disclosed also is an electrode tip for sensing bioelectrical potential. The electrode tip can comprise an electrode tip body, electrode arms coupled to the electrode tip body, and deflectable electrode legs coupled to the electrode arms. The electrode legs can have a non-biased configuration and a splayed configuration. The electrode legs can be configured to translate (e.g., spread out or splay inward) into the splayed configuration when a compressive force is applied to the electrode tip body and the one or more electrode legs. Alternatively, the electrode legs can be configured to splay inward into the splayed configuration when a compressive force is applied to the electrode tip body and the one or more electrode legs. For example, the electrode legs can be configured to splay inwards into an inward splayed configuration when a compressive force is applied to the electrode tip body and the one or more electrode legs. The electrode tip body, the electrode arms, and the electrode legs can comprise or be made in part of a conductive material.

Each of the electrode legs can have a leg longitudinal axis. The leg longitudinal axes of the electrode legs can be substantially parallel to one another when the electrode legs are in the non-biased configuration. The leg longitudinal axes of the electrode legs can be substantially non-parallel to one another when the electrode legs are in the splayed configuration.

Each of the electrode legs can be an elongate rod having a leg diameter and the electrode tip body can be a cylindrical body having a tip body diameter. A ratio of the leg diameter to the tip body diameter can be between about 1:2 and 1:10.

The electrode arms can curve along a spiral pattern or trajectory. Each of the electrode arms can curve in at least one of a clockwise or left-handed rotational direction and a counterclockwise or right-handed rotational direction. Each of the electrode arms can comprise a proximal arm end and a distal arm end. Each of the electrode arms can curve along a pitched or descending helical trajectory such that the distal arm end is vertically lower or below the proximal arm end.

The electrode tip can also comprise lateral struts extending radially from the electrode tip body. At least one of the lateral struts couple at least one of the electrode arms to the electrode tip body. The electrode tip body can have a substantially circular transverse cross-section. The lateral struts can be coupled to the electrode tip body at positions arranged uniformly or equidistantly around a circumference of the electrode tip body.

Each of the electrode legs can be an elongate rod having a leg diameter, a leg proximal end, and leg distal end. Each of the electrode legs can also have a leg height as measured from the leg proximal end to the leg distal end.

Moreover, each of the electrode legs can be coupled to an electrode foot at the leg distal end. The electrode foot can comprise or be made in part of a solid conductive material. The electrode foot can have a maximum foot diameter. The maximum foot diameter can be greater than the leg diameter. The electrode foot can also have a foot proximal end, a foot distal end, and a foot height as measured from the foot proximal end to the foot distal end. In some instances, the leg height can be greater than the foot height. The ratio of the foot height to the leg height can be between about 1:1 and 1:10.

The electrode tip body can comprise a cup-shaped portion surrounding a hollow center. The electrode tip can also comprise a ferromagnetic component encased within a portion of the electrode tip body in proximity to a bottom surface of the cup-shaped portion. The cup-shaped portion can be configured to couple to and surround at least part of a ferromagnetic element serving as part of an electrode. The ferromagnetic component can be a permanent magnet. The ferromagnetic component can also be a ferromagnetic metal. At least part of the electrode tip body can comprise or be made in part of a ferromagnetic material.

Disclosed is also an electrode for sensing bioelectrical potential. The electrode can comprise an electrode body comprising a first ferromagnetic component positioned at a distal end of the electrode body and a detachable electrode tip comprising an electrode tip body comprising a second ferromagnetic component configured to magnetically couple to the first ferromagnetic component to attach the electrode tip to the electrode body. The electrode tip can further comprise one or more electrode legs coupled to the electrode tip body. The electrode legs can be deflectable such that the electrode legs have a non-biased configuration and a splayed configuration. The electrode legs can be configured to translate (e.g., spread out or splay inward) into the splayed configuration when the electrode is compressed. In other instances, the electrode legs can be configured to splay inwards into an inward splayed configuration when a compressive force is applied to the electrode tip body and the one or more electrode legs.

The electrode can also comprise a conductive cushioning material coupled to a segment of at least one of the one or more electrode legs of the electrode tip. The conductive cushioning material can retain or be saturated with one or more conductors.

The conductive cushioning material can be a cured polymeric material. For example, the conductive cushioning material can be a hydrogel. In some instances, the hydrogel can be a crystallized hydrogel. The hydrogel can be cured by ultraviolet (UV) radiation. The hydrogel can comprise glycerin. The hydrogel can be coated on to a segment of at least one of the one or more electrode legs by dip-coating. The hydrogel can also be coupled to a segment of at least one of the one or more electrode legs by mold casting. The hydrogel can retain or be saturated with one or more conductors.

The conductive cushioning material can also be a foam saturated or infused with the one or more conductors. The conductive cushioning material can be an absorbent cotton padding saturated or infused with the one or more conductors. The conductive cushioning material can be a conductive sponge saturated or infused with the one or more conductors. The one or more conductors can comprise at least one of carbon, metal chlorides, conductive ions, and conductive nanoparticles. The conductive cushioning material can be non-residue-forming such that residue is not left on a skin surface of the patient.

The conductive cushioning material can have a maximum thickness ranging from about 0.05 mm to about 2.5 mm as measured from an exterior surface of an electrode leg. The conductive cushioning material can comprise a cushion distal end. Each of the one or more electrode legs can comprise a leg distal end. The cushion distal end can extend beyond the legal distal end such that the cushion distal end is vertically inferior to the leg distal end.

The conductive cushioning material can be ovoid-shaped. The conductive cushioning material can be substantially spherical-shaped.

The conductive cushioning material can have a cushion height as measured from a cushion proximal end to a cushion distal end. The electrode leg coated or covered by the conductive cushioning material can comprise an uncovered segment. In some instances, a height of the uncovered segment can be greater than the cushion height. In other instances, the height of the uncovered segment can be less than the cushion height.

Each of the electrode legs can have a leg longitudinal axis. The leg longitudinal axes of the electrode legs can be substantially parallel to one another when the two or more electrode legs are in the non-biased configuration. The leg longitudinal axes of the electrode legs can be substantially non-parallel to one another when the two or more electrode legs are in the splayed configuration.

Each of the one or more electrode legs can be an elongate rod having a leg diameter. The electrode tip body can be a cylindrical body having a tip body diameter. A ratio of the leg diameter to the tip body diameter can be between about 1:2 and 1:10.

The electrode tip can further comprise one or more electrode arms. At least one of the one or more electrode arms can couple at least one of the electrode legs to the electrode tip body. The one or more electrode arms comprise or be made in part of a conductive material.

The one or more electrode arms can curve along a spiral pattern or trajectory. Each of the one or more electrode arms can curve in at least one of a clockwise or left-handed rotational direction and a counterclockwise or right-handed rotational direction. Each of the electrode arms can comprise a proximal arm end and a distal arm end. Each of the one or more electrode arms can curve along a pitched or descending helical trajectory such that the distal arm end is vertically lower or below the proximal arm end.

The electrode tip can further comprise one or more lateral struts extending radially from the electrode tip body. At least one of the one or more lateral struts can couple at least one of the one or more electrode arms to the electrode tip body. The one or more lateral struts can comprise or be made in part of a conductive material. The electrode tip body can have a substantially circular transverse cross-section. A plurality of lateral struts can be coupled to the electrode tip body at positions arranged uniformly or equidistantly around a circumference of the electrode tip body.

The electrode tip body can comprise a cup-shaped portion surrounding a hollow center. A ferromagnetic component can be encased within a portion of the electrode tip body in proximity to a bottom surface of the cup-shaped portion. The cup-shaped portion can be configured to couple to and surround at least part of a ferromagnetic element of an electrode coupled to an EEG headset. The ferromagnetic component can be a permanent magnet. The ferromagnetic component can also be a ferromagnetic metal.

A headset for sensing bioelectrical potential is also disclosed. The headset can comprise a left junction and a right junction, a plurality of length-adjustable bands connecting the left junction and the right junction, and a number of electrodes. Each of the electrodes can comprise an electrode body coupled to one of the plurality of length-adjustable bands and a detachable electrode tip configured to be detachably coupled to the electrode body. The electrode tip can comprise an electrode tip body and one or more electrode legs coupled to the electrode tip body. The electrode legs can be deflectable such that the electrode legs have a non-biased configuration and a splayed configuration. The electrode legs can be configured to translate (e.g., spread out or splay inward) into the splayed configuration when the headset is worn by a user.

Each of the length-adjustable bands can comprise an arched segment. The arched segment of one of the length-adjustable bands can be separated from the arched segment of an immediately adjacent length-adjustable band by a gap or void space.

The plurality of length-adjustable bands can comprise at least a frontal band positioned closest to a nasion of a user when the headset is worn on a head of the user, a coronal band positioned closest to a vertex of the user, an occipital band positioned closest to an inion of the user, an antero-bregmatic band positioned in between the frontal band and the coronal band, and a parietal band positioned in between the coronal band and the occipital band.

The electrode can also comprise a conductive cushioning material coupled to a segment of at least one of the one or more electrode legs of the electrode tip. The conductive cushioning material can retain or be saturated with one or more conductors.

The conductive cushioning material can be a cured polymeric material. For example, the conductive cushioning material can be a hydrogel. In some instances, the hydrogel can be a crystallized hydrogel. The hydrogel can be cured by ultraviolet (UV) radiation. The hydrogel can comprise glycerin. The hydrogel can be coated on to a segment of at least one of the one or more electrode legs by dip-coating. The hydrogel can also be coupled to a segment of at least one of the one or more electrode legs by mold casting. The hydrogel can retain or be saturated with one or more conductors.

The conductive cushioning material can also be a foam saturated or infused with the one or more conductors. The conductive cushioning material can be an absorbent cotton padding saturated or infused with the one or more conductors. The conductive cushioning material can be a conductive sponge saturated or infused with the one or more conductors. The one or more conductors can comprise at least one of carbon, metal chlorides, conductive ions, and conductive nanoparticles. The conductive cushioning material can be non-residue-forming such that residue is not left on a skin surface of the patient.

The conductive cushioning material can have a maximum thickness ranging from about 0.05 mm to about 2.5 mm as measured from an exterior surface of an electrode leg. The conductive cushioning material can comprise a cushion distal end. Each of the one or more electrode legs can comprise a leg distal end. The cushion distal end can extend beyond the legal distal end such that the cushion distal end is vertically inferior to the leg distal end.

The conductive cushioning material can be ovoid-shaped. The conductive cushioning material can be substantially spherical-shaped.

The conductive cushioning material can have a cushion height as measured from a cushion proximal end to a cushion distal end. The electrode leg coated or covered by the conductive cushioning material can comprise an uncovered segment. In some instances, a height of the uncovered segment can be greater than the cushion height. In other instances, the height of the uncovered segment can be less than the cushion height.

Each of the electrode legs can have a leg longitudinal axis. The leg longitudinal axes of the electrode legs can be substantially parallel to one another when the two or more electrode legs are in the non-biased configuration. The leg longitudinal axes of the electrode legs can be substantially non-parallel to one another when the two or more electrode legs are in the splayed configuration.

Each of the one or more electrode legs can be an elongate rod having a leg diameter. The electrode tip body can be a cylindrical body having a tip body diameter. A ratio of the leg diameter to the tip body diameter can be between about 1:2 and 1:10.

The electrode tip can further comprise one or more electrode arms. At least one of the one or more electrode arms can couple at least one of the electrode legs to the electrode tip body. The one or more electrode arms comprise or be made in part of a conductive material.

The one or more electrode arms can curve along a spiral pattern or trajectory. Each of the one or more electrode arms can curve in at least one of a clockwise or left-handed rotational direction and a counterclockwise or right-handed rotational direction. Each of the electrode arms can comprise a proximal arm end and a distal arm end. Each of the one or more electrode arms can curve along a pitched or descending helical trajectory such that the distal arm end is vertically lower or below the proximal arm end.

The electrode tip can further comprise one or more lateral struts extending radially from the electrode tip body. At least one of the one or more lateral struts can couple at least one of the one or more electrode arms to the electrode tip body. The one or more lateral struts can comprise or be made in part of a conductive material. The electrode tip body can have a substantially circular transverse cross-section. A plurality of lateral struts can be coupled to the electrode tip body at positions arranged uniformly or equidistantly around a circumference of the electrode tip body.

The electrode tip body can comprise a cup-shaped portion surrounding a hollow center. A ferromagnetic component can be encased within a portion of the electrode tip body in proximity to a bottom surface of the cup-shaped portion. The cup-shaped portion can be configured to couple to and surround at least part of a ferromagnetic element of an electrode coupled to an EEG headset. The ferromagnetic component can be a permanent magnet. The ferromagnetic component can also be a ferromagnetic metal.

Another instance of an electrode tip for sensing bioelectrical potential is also disclosed. The electrode tip can comprise an electrode tip body comprising a proximal side and a substantially planar distal side or face. The distal side can be substantially planar. A conductive cushioning material can be coupled to or coated onto the distal side. The conductive cushioning material can retain or be saturated with one or more conductors.

The conductive cushioning material can be a cured polymeric material. The one or more conductors can comprise at least one of carbon, metal chlorides, conductive ions, and conductive nanoparticles. The conductive cushioning material can be a hydrogel. The hydrogel can be coated on to the distal side by dip-coating. The hydrogel can also be coupled to the distal side by mold casting.

The hydrogel can be cured by ultraviolet (UV) radiation. The hydrogel can comprise glycerin.

The conductive cushioning material can also be a foam saturated or infused with the one or more conductors. Alternatively, the conductive cushioning material can be an absorbent cotton padding saturated or infused with the one or more conductors. The conductive cushioning material can also be a conductive sponge saturated or infused with the one or more conductors.

The conductive cushioning material can have a maximum thickness ranging from about 0.05 mm to about 2.5 mm as measured from an exterior surface of the electrode tip body. The conductive cushioning material can be substantially cylindrical-shaped. The conductive cushioning material can also be substantially ovoid-shaped, spherical-shaped, hemispherical-shaped, cuboid-shaped, and frustoconical-shaped. The conductive cushioning material is non-residue-forming such that no residue is left on a skin surface of the patient after use.

The electrode tip can comprise a ferromagnetic component. The ferromagnetic component can be encased within the electrode tip body. The ferromagnetic component can be a permanent magnet. The ferromagnetic component can also be a ferromagnetic metal.

The electrode tip body can comprise a cup-shaped portion defined along the proximal side. The cup-shaped portion can surround a hollow center. The ferromagnetic component can be encased within a portion of the electrode tip body in proximity to a bottom surface of the cup-shaped portion. The cup-shaped portion can be configured to couple to and surround at least part of a ferromagnetic element serving as part of an electrode. At least part of the electrode tip body can also be made of a ferromagnetic material.

BRIEF DESCRIPTION OF THE DRAWINGS

FIG. 12A illustrates a perspective view of a variation of a detachable electrode tip having an electrode leg radially aligned with a neighboring or flanking lateral strut.

FIG. 12B illustrates a perspective view of a variation of a detachable electrode tip having an electrode leg radially offset from a neighboring or flanking lateral strut.

FIG. 12C illustrates a perspective view of another variation of a detachable electrode tip having an electrode leg radially offset from a neighboring or flanking lateral strut.

FIG. 12D illustrates a perspective view of another variation of a detachable electrode tip having an electrode leg radially offset from a neighboring or flanking lateral strut.

FIG. 13A illustrates top and side views of a variation of a detachable electrode tip having an electrode leg radially aligned with a neighboring or flanking lateral strut and electrode arms curving or spiraling in plane with other electrode arms.

FIG. 13B illustrates top and side views of a variation of a detachable electrode tip having an electrode leg radially offset from a neighboring or flanking lateral strut and electrode arms curving or spiraling in plane with other electrode arms.

FIG. 14A illustrates top and side views of a variation of a detachable electrode tip having an electrode leg radially offset from a neighboring or flanking lateral strut and electrode arms curving or spiraling out of plane with other electrode arms in a descending or helical manner.

FIG. 14B illustrates top and side views of another variation of a detachable electrode tip having an electrode leg radially offset from a neighboring or flanking lateral strut and electrode arms curving or spiraling out of plane with other electrode arms in a descending or helical manner.

DETAILED DESCRIPTION

Figure 1:
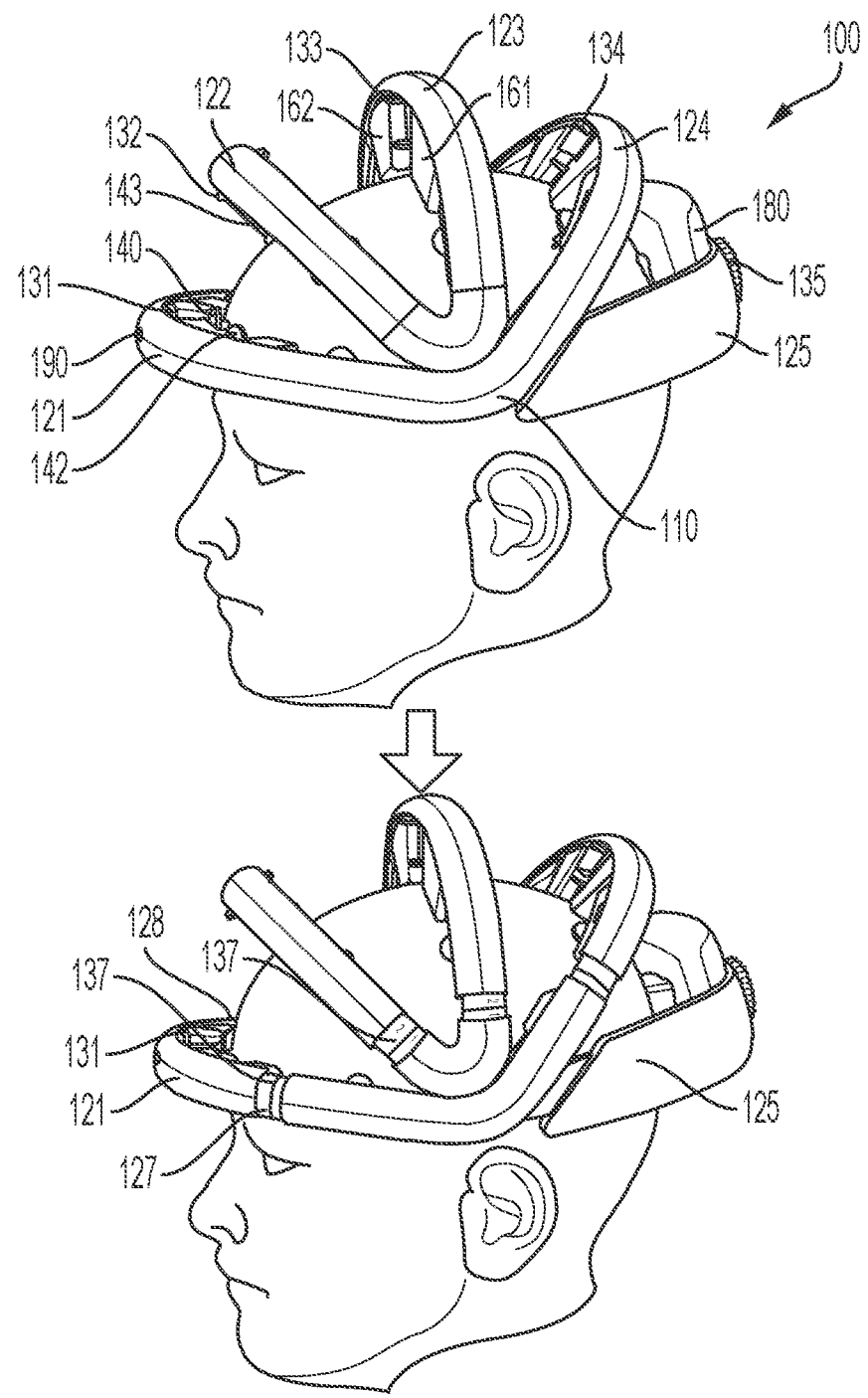
FIG. 1 illustrates the expansion of a headset for sensing bioelectrical potential.

Variations of the devices, systems, and methods described herein are best understood from the detailed description when read in conjunction with the accompanying drawings. It is emphasized that, according to common practice, the various features of the drawings may not be to scale. The dimensions of certain features have been expanded or reduced for clarity and not all features may be visible or labeled in every drawing. The drawings are taken for illustrative purposes only and are not intended to define or limit the scope of the claims to that which is shown.

Headset

As shown in FIGS. 1-8, a headset 100 for collecting biosignal data includes: a left junction 110; a right junction 112; a first band 121 spanning the left junction 110 and the right junction 112; a first band adjuster 131 configured to adjust a first length of the first band 121 between the left junction 110 and the right junction 112; a second band 122 spanning the left junction 110 and the right junction 112 and radially offset from the first band 121 about a lateral axis spanning the left junction 110 and the right junction 112; a second band adjuster 132 configured to adjust a second length of the second band 122 between the left junction 110 and the right junction 112; a first electrode 140 fixedly mounted to the first band 121 and centered between the left junction 110 and the right junction 112; a second electrode 152 mounted to the first band 121 between the first electrode 140 and the left junction 110 and laterally-adjustable along the first length of the first band 121; and a third electrode 153 mounted to the second band 122 between the left junction 110 and the right junction 112 and laterally-adjustable along the second length of the second band 122.

One variation of the electroencephalography (or "EEG") headset 100 includes a junction; a first band 121 coupled to the junction; a first band adjuster 131 configured to adjust a first length of the first band 121 extending from the junction; a first length scale 137 arranged on the first band 121 and configured to indicate a particular length value, along the length scale 137, corresponding to a current length setting of the first band 121; a second band 122 coupled to the junction and radially offset from the first band 121 about a lateral axis of the junction; a second band adjuster 132 configured to adjust a second length of the second band 122 extending from the junction; a first electrode 140; a first electrode adjuster 141 coupling the first electrode 140 to the first band 121 over a range of lateral positions along the first length of the first band 121 and including a set of electrode position labels 147 indicating discrete lateral positions of the first electrode 140 in the first electrode adjuster 141, each electrode position label, in the set of electrode position labels 147, indicating a target lateral position of the first electrode 140 in the first electrode adjuster 141 for a particular length value, along the length scale 137, indicated by the first band 121 according to an electrode placement standard; and a second electrode 152 mounted to the second band 122 offset from the junction.

Figure 2:
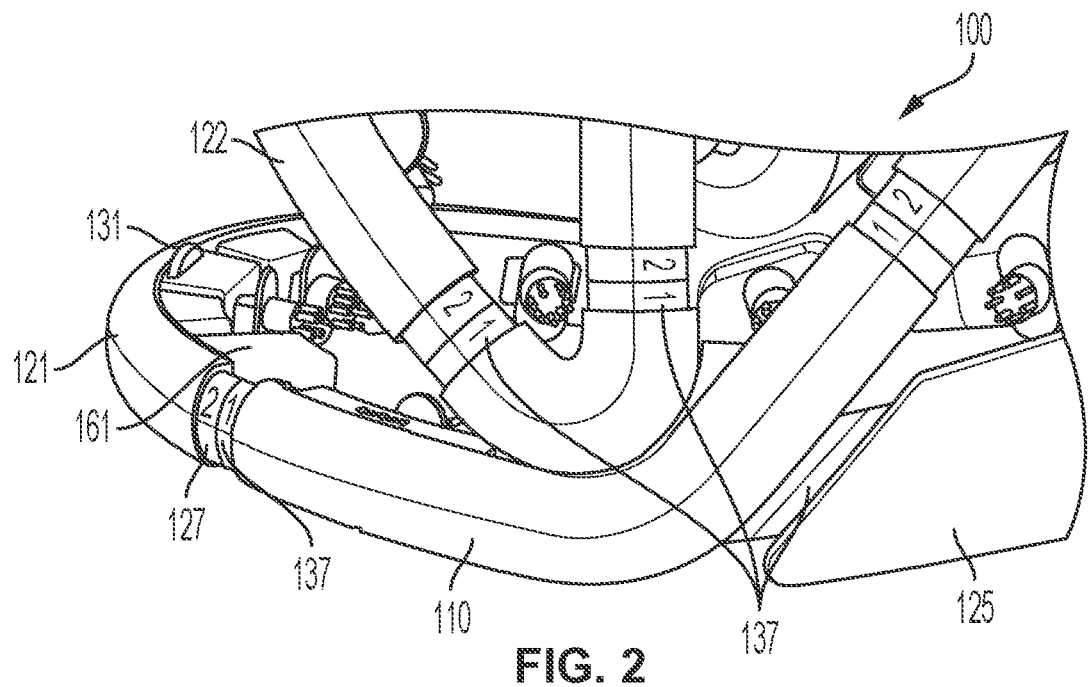
FIG. 2 illustrates a close-up perspective view of a junction of the headset.

As shown in FIGS. 1 and 2, another variation of the EEG headset 100 includes a left junction 110; a right junction 112; a first band 121 adjustably coupled to and spanning the left junction 110 and the right junction 112; a first set of electrodes arranged along the first band 121; a second band 122 adjustably coupled to and spanning the left junction 110 and the right junction 112 and radially offset from the first band 121; a second set of electrodes arranged along the second band 122, the second set of electrodes including a second electrode 152 fixedly coupled to the second band 122 and centered between the left junction 110 and the right junction 112; a third band 123 adjustably coupled to and spanning the left junction 110 and the right junction 112 and radially offset from the second band 122; a third set of electrodes arranged along the third band 123, the third set of electrodes including a third electrode 153 fixedly coupled to the third band 123 and centered between the left junction 110 and the right junction 112; a fourth band 124 adjustably coupled to and spanning the left junction 110 and the right junction 112 and radially offset from the third band 123; and a fourth set of electrodes arranged along the fourth band 124, the fourth set of electrodes including a fourth electrode 154 fixedly coupled to the fourth band 124 and centered between the left junction 110 and the right junction 112

Figure 3:
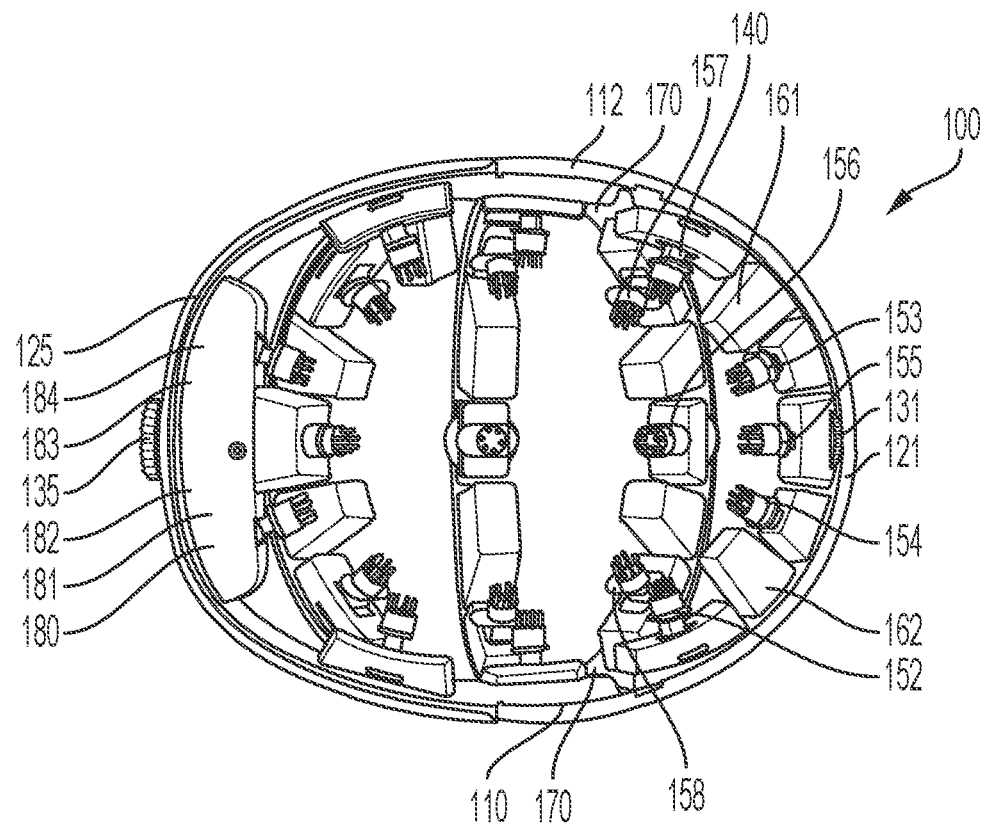
FIG. 3 illustrates a bottom plan view of the headset.

As shown in FIGS. 2 and 3, yet another variation of the EEG headset 100 includes a left junction 110 configured for placement adjacent a left ear of a user; a right junction 112 configured for placement adjacent a right ear of a user; a band 121 spanning the left junction 110 and the right junction 112; a band adjuster 131 configured to modify an effective length of the band 121 between the left junction 110 and the right junction 112; a first electrode 140 fixedly mounted to the band 121 and centered between the left junction 110 and the right junction 112; a second electrode 152; a second electrode 152 adjustor coupled to the band 121 between the first electrode 140 and the left junction 110 and supporting the second electrode 152 along a linear adjustment range; a third electrode 153; and a third electrode 153 adjustor coupled to the band 121 between the first electrode 140 and the right junction 112 and supporting the third electrode 153 along a linear adjustment range.

Applications

Generally, the EEG headset 100 defines a singular structure containing a set of integrated electrodes arranged across a set of adjustable bands that can be expanded and retracted to fit heads of various shapes and sizes. The set of adjustable bands are arranged in particular orientations and are configured to locate both fixed and adjustable electrodes in specific locations according to the 10-20 system (or other electrode placement standard). The set of integrated electrodes in the EEG headset 100 includes both: fixed electrodes, such as arranged at each junction and along the anteroposterior centerline of various bands and adjustable electrodes that can be adjusted along a limited adjustment range to re-center these electrodes following adjustment of their corresponding bands. In particular, the EEG headset 100 includes mechanisms supporting both a limited number of macro adjustments at various bands and a limited number of micro adjustments at adjustable electrodes to realize electrode placement rules defined by the 10-20 system (or other electrode placement standard) within a positional tolerance of the 10-20 system.

During setup of the EEG headset 100 on a user in preparation for an EEG test, an EEG test administrator can place the EEG headset 100 on the user's head and adjust the effective length of each band via band adjusters in order to achieve a sufficiently close fit between each band and the user's scalp. Because certain electrodes within the EEG headset 100 (e.g., electrodes at the F7, F3, F4, F8, C3, C4, T5, P3, P4, and T6 positions, shown in FIGS. 3 and 6) may no longer be properly centered between adjacent fixed electrodes, the EEG test administrator can then adjust these electrodes locally via their electrode adjusters to bring the complete set of electrodes back into alignment with the 10-20 system, as shown in FIG. 7.

The junctions and bands within the EEG headset 100 can define semi-rigid structures configured to accurately and repeatably locate electrodes on a user's head according to the 10-20 system (or other electrode placement standard). Furthermore, each electrode can be integrated into and irremovable from the EEG headset 100 (except for electrode tips, which may be replaceable, as described below) such that sense signals read from each electrode during an EEG test can be automatically tagged—by the EEG headset 100 or connected computing device—with a correct channel label based on predefined locations of each electrode within the EEG. In particular, the EEG headset 100 can include a set of junctions, bands, band adjusters, electrodes, and electrode adjusters that cooperate to define a system that can be relatively quickly reconfigured for a new user by an EEG test administrator (or by the user, etc.) to accurately and repeatably realize the 10-20 system (or any other EEG system), thereby enabling the EEG headset 100 to collect quality and properly-labeled EEG data during an EEG test.

Junctions, Bands, and Band Adjusters

The EEG headset 100 includes: a left junction 110; a right junction 112; a first band 121 including a first end coupled to the left junction 110, a second end coupled to the right junction 112, a first band adjuster 131 configured to adjust a distance between the first end and the left junction 110 and between the second end and the right junction 112; and a second band 122 radially offset from the first band 121 and including a third end coupled to the left junction 110, a fourth end coupled to the right junction 112, and a second band adjuster 132 configured to adjust a distance between the third end and the left junction 110 and between the fourth end and the right junction 112. Generally, the left and right junctions 110, 112 function to radially locate each band (e.g., the first, second, third, fourth, and fifth bands) in the EEG headset 100, and the bands function to support fixed and adjustable electrodes against a user's scalp according to electrode placement definitions and tolerance defined by the 10-20 EEG electrode configuration (or other EEG electrode placement standard).

3.1 Junctions

The left and right junctions 110, 112 can rest on a user's head just above and in front of the user's left and right ears, respectively, and can locate: the first band 121 at a 0° position; the second band 122 at a 40° position; the third band 123 at an 80° position; the fourth band 124 at a 125° position; and the fifth band 125 at the 170° position. In this implementation, when the EEG headset 100 is worn by a user, the left and right junctions 110, 112 can thus radially locate these band such that: the first band 121 extends across the user's forehead; the second band 122 passes over the user's frontal lobe; the third band 123 passes over the user's primary motor and somatosensory cortexes near the central sulcus; the fourth band 124 passes over the user's parietal lobe; and the fifth band 125 extends across the back of the user's skull adjacent the user's occipital lobe according to the 10-20 system.

For example, and as shown in FIG. 1, the left junction 110, the right junction 112, the first band 121, the first band adjuster 131, the second band 122, the second band adjuster 132, the first electrode 140, the second electrode 152, and the third electrode 153, etc. can cooperate to define an adjustable EEG headset configured to be worn on a head of a user. The left junction 110 can be configured to fall adjacent a left ear of the user when the adjustable EEG headset is worn on the head of the user; and the right junction 112 can be configured to fall adjacent a right ear of the user when the adjustable EEG headset is worn on the head of the user. The third band 123 can extend approximately along a coronal plane over the head of the user when the adjustable EEG headset is worn on the head of the user; and the second band 122 can extend over the head of the user between the third band 123 and a forehead of the user when the adjustable EEG headset is worn on the head of the user.

3.2 Band Adjustment

In one implementation shown in FIGS. 1 and 2, a band 121 includes: a left strap defining a left internal rack 127 (or "toothed strap") and extending from the left junction 110; a right strap defining a right internal rack 128 and extending from the right junction 112; and a sleeve 126 enclosing the left internal rack 127 and the right internal rack 128. In this implementation, the electrodes can be coupled to the sleeve 126; a band adjuster 131 for this band can include a gear arranged on the sleeve 126, engaged to the left internal rack 127 relative to the right internal rack 128, manually operable in a first direction to expand the first band 121, and manually operable in a second direction to contract the first band 121.

For example, a first band 121 extending toward the front of the EEG headset 100 (e.g., configured to fall along, contact, or otherwise engage a user's forehead) can include: a left strap extending from the left junction 110 toward the front of the EEG headset 100 and defining a left rack gear 127; and the right strap extending from the right junction 112 toward the front of the EEG headset 100, vertically offset from the left strap, curving toward and overlapping the left strap, and defining a right rack gear 128 facing the left rack gear 127. In this implementation, the first band 121 also includes a sleeve 126 that spans the left and right junctions 110, 112 and encases the left and right rack gears 127, 128. In this example, a first band adjuster 131 can include: a knurled knob arranged over or extending outside of the sleeve 126; and a pinion arranged inside the sleeve 126, interposed between and mating with the left and right rack gear 127, 128s and radially coupled to the knob. Thus, when the EEG test administrator rotates the knob in a first direction, the pinion can drive the left and right rack gears 127, 128 apart, thereby increasing the effective length of the first band 121. Similarly, when an EEG test administrator rotates the knob in a second direction, the pinion can drive the left and right rack gears 127, 128 toward each other, thereby shortening the effective length of the first band 121. In particular, rotation of the band adjuster 131 can uniformly shift the first and second ends of the first band 121 away from (or toward) the left and right junctions 110, 112, respectively. Furthermore, surfaces on the left and right straps extending from the left and right junctions 110, 112 can also include demarcations—such as printed, embossed, or debossed alphabetic or numerical symbols in the form of a scale—that are exposed as the first band 121 is expanded, thereby visually indicating the adjustment position of the first band 121.

In this implementation, the first band 121 can also include a length scale 137 corresponding to discrete lengths (or discrete length sub-ranges) of the first band 121, wherein each length value along the length scale 137 corresponds to a particular electrode position label—in a set of electrode position labels 147—on a linear rack that couples an adjustable electrode to the first band 121, as described below, as shown in FIG. 2. The first band 121 (and/or the first band adjuster 131) can thus indicate a particular length value—along this length scale 137—that corresponds to a current length setting of the first band 121 as a technician or EEG test administrator adjusts the EEG headset 100 for the unique size and shape of a user's head. For example: the length scale 137 can include discrete textual symbols highlighted in a range of discrete colors arranged on the left internal rack 127; and the sleeve 126 can indicate a particular textual symbol, in the first sequence of discrete textual symbols, corresponding to a current length setting of the first band 121 by obscuring all textual symbols other than the particular textual symbol corresponding to the current length of the first band 121 or by aligning a pointer to this particular textual symbol. As described below, the technician or EEG test administrator can then manually shift adjustable electrodes on the first band 121 to lateral positions labeled with the same textual symbol and/or color value in order to locate these adjustable electrodes within a threshold locational tolerance of their target locations on the user's scalp—relative to each other, relative to a fixed electrode on the first band 121, and/or relative to electrodes on other bands in the EEG headset 100, etc.—specified by a 10-20 EEG electrode configuration or (other electrode placement standard). The technician or EEG test administrator can repeat this process for each other band and adjustable electrode in the EEG headset 100 in order to configure the EEG headset 100 for the user.

In the foregoing implementation, each other band in the EEG headset 100 can similarly include a left strap 127, and right strap 128, a sleeve 126, and a band adjuster 131 configured to expand and contract the band 121 when manipulated by an EEG test administrator. These left straps can terminate at the left junction 110, and these right straps can terminate at the right junction 112. The left and right junctions 110, 112 can therefore form reference locations on a user's head (e.g., above and immediately ahead of the user's ears) and can radially locate the bands (e.g., the first, second, third, fourth, and fifth bands) relative to one another and relative to these reference locations such that—once the bands are adjusted to length and the adjustable electrodes positioned accordingly—the set of sense electrodes within the EEG headset 100 fall within threshold distances of target electrode positions specified in the 10-20 EEG electrode configuration (or other electrode placement standard).

Figure 9:
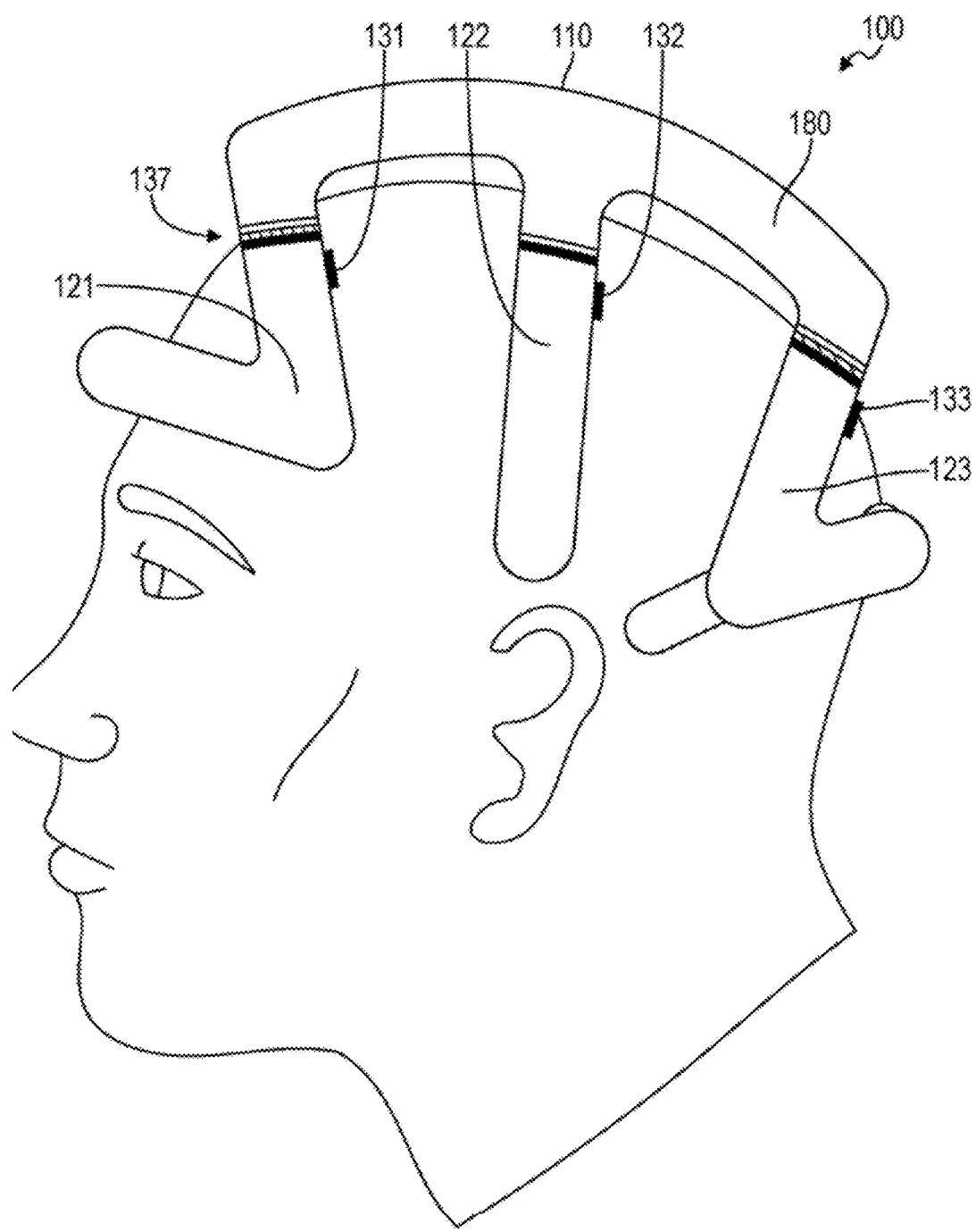
FIG. 9 illustrates a side view of a user wearing the headset.

In another implementation shown in FIG. 9, the EEG headset 100 includes: a central body configured for placement on the top of a user's head along the anteroposterior centerline of the user's skull; a set of adjustable bands extending downwardly from the central body; and a set of fixed electrodes and adjustable electrodes distributed across the interior surfaces of the bands and the central body. In this implementation, each band can be independently adjustable and can include at least one electrode (e.g., one fixed electrode or one fixed electrode and one adjustable electrode). Alternatively, pairs of like left and right bands can be linked by a common band adjuster such that pairs of like bands are uniformly adjusted relative to the centerline of the central body.

In the foregoing implementations, the left junction 110, right junction 112, bands, and band adjusters, etc. can be formed in a rigid material, such as injection-molded plastic (e.g., nylon) or molded fiber-impregnated polymer. However, the junctions, bands, and/or central body, etc. can be formed in any other material or define any other geometry.

Chin Strap

In one variation, the EEG headset 100 further includes a chin strap coupled to the left and right junctions (or to one or more bands) and configured to fix the EEG headset 100 to a user's chin, ears, or other head feature, thereby preventing the EEG headset 100 moving relative to the user's head and from falling off of the user's head if the user moves during an EEG test performed at the EEG headset 100.

Sense Electrodes

The EEG headset 100 includes a set of sense electrodes arranged across the set of bands. When the EEG headset 100 is worn by the user, a sense electrode can: contact the user's scalp; detect a high-impedance sense signal from the user's skin; convert the low-amplitude, high-impedance sense signal into a well-driven low-impedance sense signal; and pass the low-impedance sense signal to the controller 184.

Electrode Composition

Each sense electrode is configured to contact a user's skin and to pass neural oscillation data in the form of a sense signal from the user's skin to the controller 184 (e.g., to a signal processor within the controller 184). For example, each sense electrode in the set of sense electrodes can define a dry EEG electrode including: a substrate; a set of electrically-conductive prongs extending from a first side of the substrate; and an amplifier coupled to the substrate opposite the set of prongs and configured to amplify an electrical signal passing through the set of prongs. The electrically-conductive prongs can be elastic (e.g., gold-plated silicone bristles) or rigid (e.g., gold-plated copper prongs). A sense electrode can alternatively include a flat or domed contact disk configured to contact the user's skin.

Figure 4:
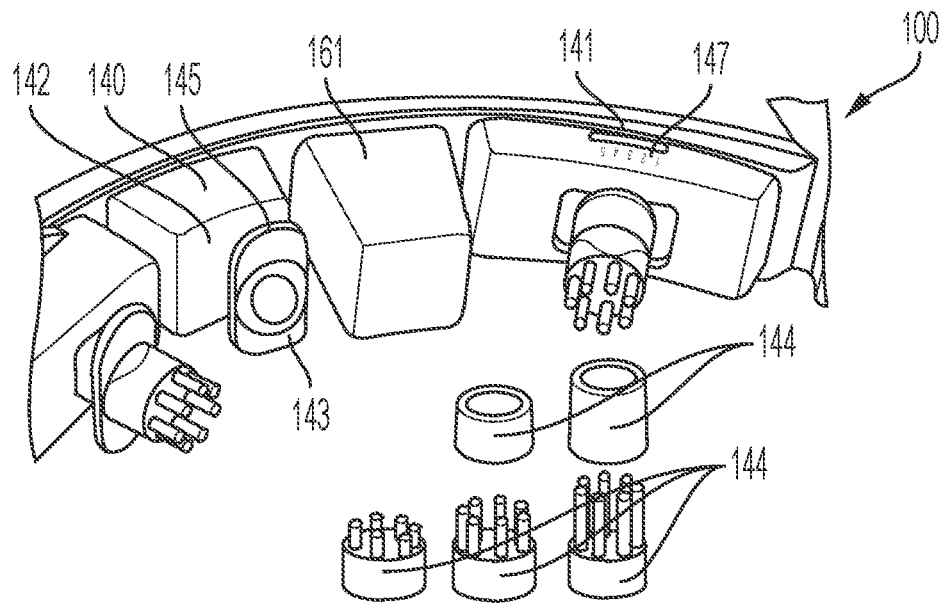
FIG. 4 illustrates a close-up perspective view of different variations of detachable electrode tips of the headset.

As shown in FIG. 4, the sense electrode can also be configured to accept interchangeable electrode tips 144, such as one of an elastic bristle electrode tip, a rigid prong electrode tip, a flat contact disk electrode tip, and a domed contact disk electrode tip, as described below. In one implementation, each sense electrode can include: an electrode body 142 coupled to the band 121 (e.g., via an electrode adjuster 141, such as in the form of a linear rack, for adjustable electrodes); a magnetic element 143 arranged on a distal end of the electrode body 142 and including a conductive surface; and a conductive lead 146 coupled to a face of the magnetic element 143, passing through the electrode body 142, and terminating at an amplifier electrically coupled to the controller 184, such as arranged in the control module 180 described below. In this implementation, the EEG headset 100 can be supplied with a kit of electrode tips 144, wherein each electrode tip in the kit of electrode tips 144 includes a ferrous element 148 configured to transiently magnetically couple to the magnetic element 143 and to transiently electrically couple to the conductive lead 146 via the conductive surface of the magnetic element 143. In this implementation, a hard or soft contact surface on an electrode tip can electrically couple to the ferrous element 148 on the back side of the electrode tip; the magnetic element 143 in an electrode can include an electrically-conductive surface (e.g., chrome or tin plating); and the amplifier—such as arranged inside the electrode body 142 or nearby in the adjacent band—can electrically couple to the magnetic element 143 via a wire arranged inside of the electrode body 142. When an electrode tip is thus installed on an electrode, the ferrous element 148 in the electrode tip can directly contact the magnetic element 143, thereby electrically coupling the contact surface of the electrode tip 144 to the amplifier. For example, a first end of the conductive lead 146 can be bonded to (e.g., potted around) a face of the magnetic element 143 with conductive adhesive, compressed against the face of the magnetic element 143 with a spring arranged inside the electrode body 142, and connected to a spring-loaded pin in contact with the face of the magnetic element 143. A separate conductive lead 146 connected to an output of the amplifier can pass through the band 121 and connect to an input of the controller 184.

In the foregoing implementation, the kit of electrode tips 144 can include electrode tips 144 defining different constant surfaces, such one each of a hard-domed electrode surface, a hard-pronged electrode surface, and a soft domed electrode surface. Electrodes in the kit can also define various lengths, such as matched to lengths of support blocks installed on adjacent regions of a band 121, as described below and shown in FIG. 4, such as to enable an EEG test administrator to reconfigure the EEG headset 100 for both adult and juvenile users.

Adjustable and Fixed Electrode Layout

As shown in FIGS. 3 and 4, the EEG headset 100 can include electrodes mounted to the interior surfaces of corresponding bands via electrode adjusters (hereinafter "adjustable electrodes") at select locations (e.g., at other than the lateral centerline of the EEG headset 100, the immediate front and rear of the EEG headset 100, and the lateral extents of the EEG headset 100). The EEG headset 100 can also include electrodes fixedly coupled to the interior surfaces of corresponding bands (hereinafter "fixed electrodes") at other locations.

Figure 6:
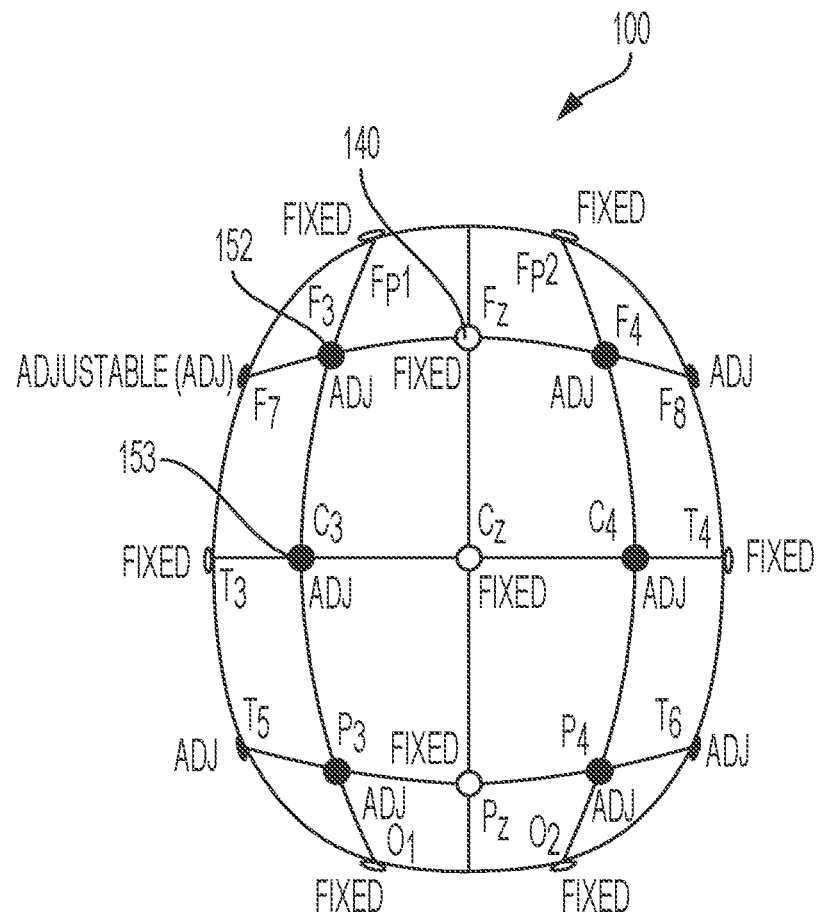
FIG. 6 illustrates a top plan view of a schematic of the headset showing the positioning of various adjustable and fixed electrodes.
Figure 7:
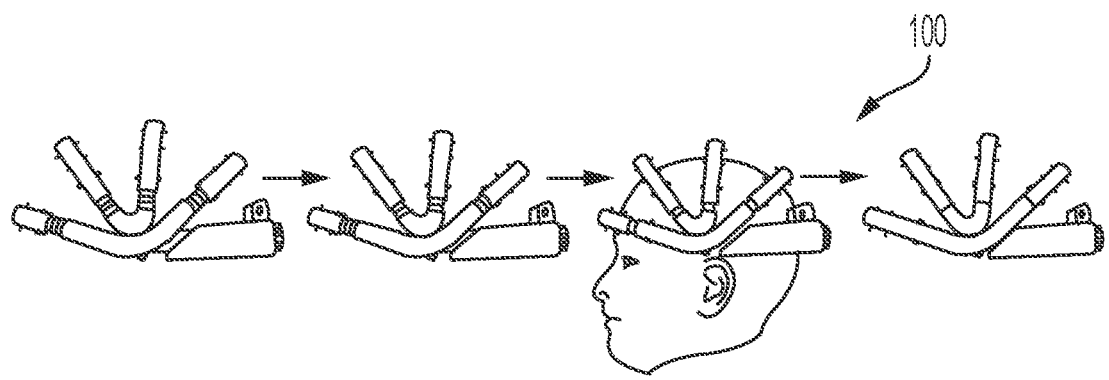
FIG. 7 illustrates an example method of adjusting a size of the headset when placing the headset on a scalp of a user.

In one implementation: the EEG headset 100 includes nineteen sense electrodes in a combination of fixed and adjustable configurations arranged across the set of bands, including one sense electrode for each of: the F7, Fp1, Fp2, and F8 positions (defined in the 10-20 system) along the first band 121; the F3, Fz, and F4 positions along the second band 122; the T3 position at the right junction 112; the T4 position at the left junction 110; the C3, Cz, and C4 positions along the third band 123; the P3, Pz, and P4 positions along the fourth band 124; and the T5, O1, O2, and T6 positions along the fifth band 125, as shown in FIGS. 3 and 6. In particular, in this example: the first band 121 can include fixed sense electrodes at the Fp1 and Fp2 sense electrode positions and adjustable sense electrodes at the F7 and F8 sense electrode positions; the second band 122 can include a fixed sense electrode at the Fz sense electrode position and adjustable sense electrodes at the F3 and F4 sense electrode positions; the third band 123 can include a fixed sense electrode at the Cz sense electrode position and adjustable sense electrodes at the C3 and C4 sense electrode positions; the fourth band 124 can include a fixed sense electrode at the Pz sense electrode position and adjustable sense electrodes at the P3 and P4 sense electrode positions; and the fifth band 125 can include fixed sense electrodes at the T5 and T6 sense electrode positions and adjustable (or fixed) sense electrodes at the O1 and O2 sense electrode positions. The EEG headset 100 can also include fixed sense electrodes at the T3 sense electrode position at the right junction 112 and at the T4 sense electrode position at the left junction 110, as shown in FIG. 6. The EEG headset 100 can further include a fixed drive electrode fixedly mounted to the first band 121 between the FP1 and FP2 sensor electrode positions, centered between the left junction 110 and the right junction 112, and configured to contact a user's skin proximal the user's forehead (e.g., centered just above the bridge of the user's nose).

In particular, in addition to the first band 121 and the second band 122, the EEG headset 100 can include: a third band 123 spanning the left junction 110 and the right junction 112 and supporting a laterally-adjustable C3 electrode, a fixed Cz electrode, and a laterally-adjustable C4 electrode in the 10-20 EEG electrode configuration; a third band adjuster 133 configured to adjust a length of the third band 123 between the left junction 110 and the right junction 112; a fourth band 124 spanning the left junction 110 and the right junction 112 and supporting a laterally-adjustable P3 electrode, a fixed Pz electrode, and a laterally-adjustable P4 electrode in the 10-20 EEG electrode configuration; a fourth band adjuster 134 configured to adjust a length of the fourth band 124 between the left junction 110 and the right junction 112; and a fifth band 125 spanning the left junction 110 and the right junction 112 and supporting a laterally-adjustable T5 electrode, a fixed O1 electrode, a fixed O2 electrode, and a laterally-adjustable T6 electrode in the 10-20 EEG electrode configuration, as shown in FIGS. 1, 3, and 6.

Therefore, in the foregoing example: a first electrode 140 mounted to the first band 121 can define a laterally-adjustable F7 electrode; a second electrode 152 mounted to the first band 121 between the first electrode 140 and the right junction 112 can be laterally-adjustable along the first length of the first band 121 to define a laterally-adjustable F8 electrode; a third electrode 153 fixedly mounted to the first band 121 between the first electrode 140 and the second electrode 152 can define a fixed FP1 electrode; a fourth electrode 154 fixedly mounted to the first band 121 between the second electrode 152 and the third electrode 153 can define a fixed FP2 electrode; a fifth electrode 155 fixedly mounted to the first band 121 between the third electrode 153 and the fourth electrode 154 (e.g., centered between the left junction 110 and the right junction 112) can define a fixed drive electrode; a sixth electrode 156 mounted at the lateral centerline of the second band 122 can define a fixed Fz electrode; a seventh electrode 157 mounted to the second band 122 between the second electrode 152 and the left junction 110 can define a laterally-adjustable F3 electrode; and an eighth electrode 158 mounted to the second band 122 between the second electrode 152 and the right junction 112 can be laterally-adjustable along the second length of the second band 122 to define a laterally-adjustable F4 electrode in the 10-20 EEG electrode configuration; etc.

Furthermore, each band adjuster can be configured to expand its corresponding band equally between the left junction 110 and the right junction 112 in order to maintain certain fixed electrodes along the lateral centerline of the EEG headset 100. For example, the second band 122 can include a fixed electrode in the Fz position, and the second band adjuster 132 can be configured to expand the second band 122 equally between the left junction 110 and the right junction 112 in order to maintain the Fz electrode along the lateral centerline of the EEG headset 100. Similarly, the third band 123 can include a fixed electrode in the Cz position, and the third band adjuster 133 can be configured to expand the third band 123 equally between the left junction 110 and the right junction 112 in order to maintain the Cz electrode along the lateral centerline of the EEG headset 100.

Adjustable Electrode

Figure 5:
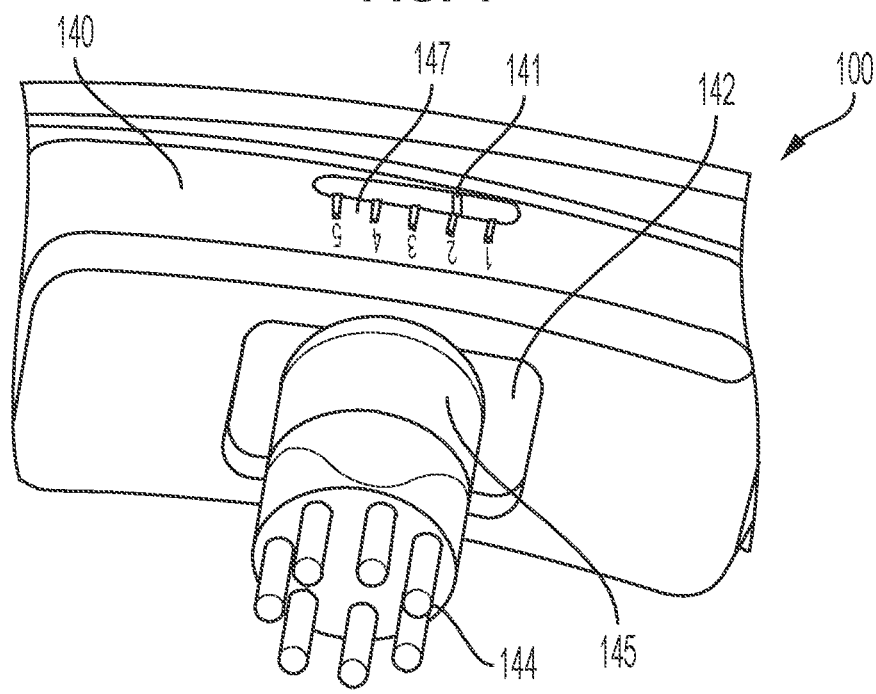
FIG. 5 illustrates a close-up perspective view of an adjustable electrode having a shoulder and a variation of a detachable electrode tip coupled to the rest of the electrode.
Figure 8:
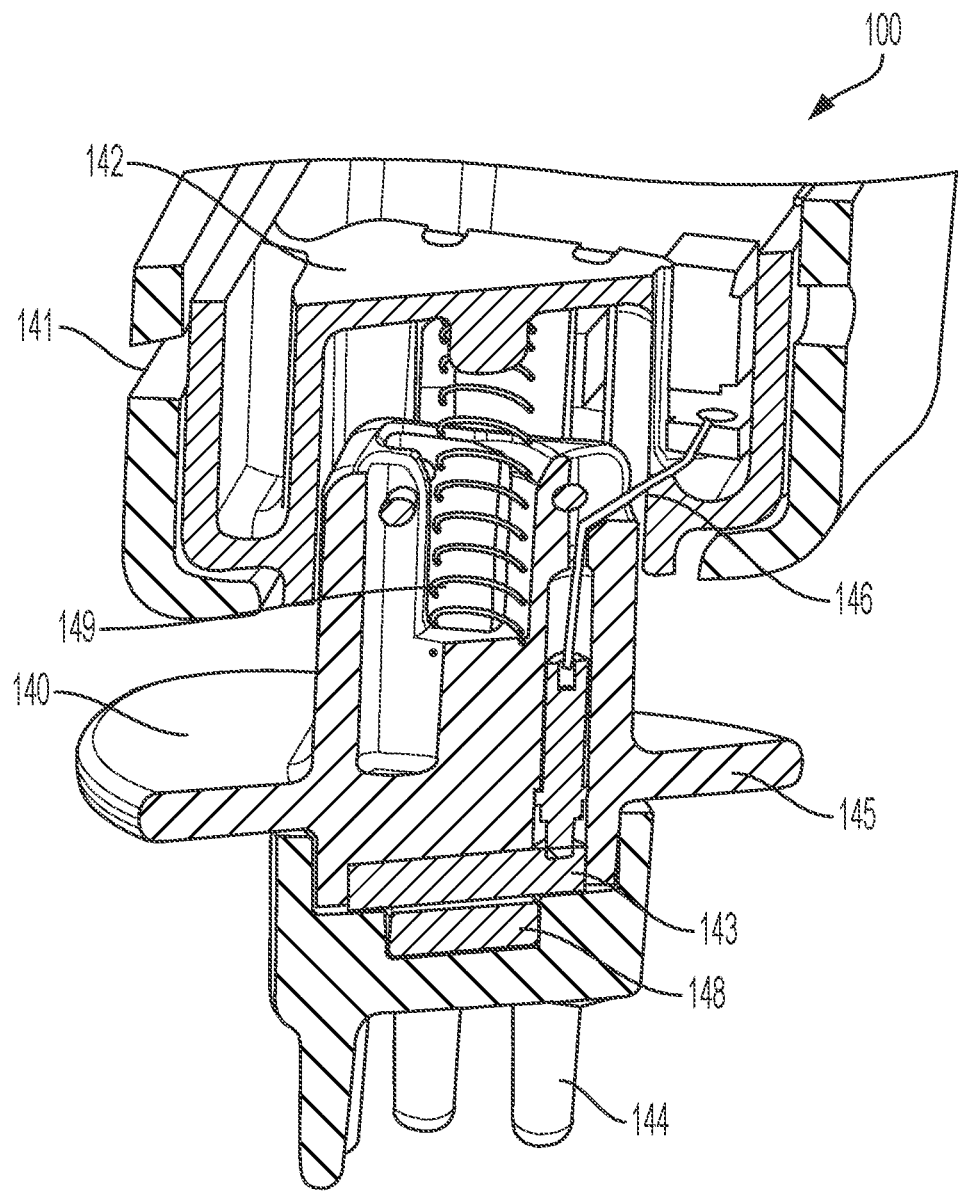
FIG. 8 illustrates a close-up cross-sectional view of a variation of an electrode having a detachable electrode tip coupled to the rest of the electrode.

In one implementation shown in FIGS. 4, 5, and 8, an adjustable electrode includes: a sense electrode; a sliding element supporting the sense electrode; a ratchet mechanism (or rack gear and follower) mounted to a band 121 and configured to retain the position of the sliding element relative to the band 121; and a button that, when manually depressed, releases the sliding element from the ratchet mechanism (or releases the follower from the rack gear), thereby enabling an EEG administrator to shift the position of the sliding element—and therefore the sense electrode—relative to the band 121. In this implementation, the sliding element and ratchet mechanism can cooperate to locate the sense electrode across a range of positions, including a linear distance parallel to the length of its corresponding band and equal to approximately half of the maximum change in effective length of the band 121 from its fully-retracted to fully-expanded positions such that the adjustable electrode can be centered between two adjacent fixed electrodes according to the 10-20 system substantially regardless of adjustment positions of the band 121. Furthermore, the band 121 supporting the adjustable electrode can include demarcations—such as printed, embossed, or debossed alphabetic or numerical symbols in the form of a scale—adjacent the button to visually indicate the adjustment position of the adjustable electrode, as shown in FIG. 5.

In a similar implementation shown in FIG. 5, an adjustable electrode includes a sense electrode; and an electrode adjuster 141 coupling the sense electrode to a corresponding band over a range of lateral positions along the length of the band 121. For example, the electrode adjuster 141 can include a linear rack, and the sense electrode can be mounted to the linear rack via a ratchet or detent mechanism that selectively retains the sense electrode in discrete locations along the linear rack. The electrode adjuster 141 can also include a set of electrode position labels 147 (e.g., a lateral position scale) indicating discrete lateral positions of the sense electrode along the electrode adjuster 141, wherein each electrode position label—in this set of electrode position labels 147—indicates a target lateral position of the sense electrode along the electrode adjuster 141 for a particular length value—along the length scale 137—indicated by the band 121, as described above, according to an electrode placement standard (e.g., a 10-20 EEG electrode configuration). In particular, the band 121 can include a length scale 137 corresponding to discrete lengths of the band 121, wherein each length value along the length scale 137 indicates correspondence to a particular electrode position label in the set of electrode position labels 147 on the linear rack. As described above, the band 121 can indicate a particular length value—along the length scale 137—corresponding to a current length setting of the band 121, and an EEG test administrator can adjust the sense electrode along the linear rack to match the electrode position label indicated by the sense electrode to the particular length value indicated by the band 121 in order to locate the sense electrode within a threshold tolerance of its target position relative to another sense electrode in the EEG headset 100.

For example, the length scale 137 on the band 121 can include a first sequence of discrete textual symbols highlighted in a range of discrete colors arranged on the left internal rack 127, as shown in FIG. 2; the adjustable electrode can be assigned a target location relative to another electrode (e.g., a fixed electrode arranged along the lateral centerline of the EEG headset 100) on the band 121 according to a 10-20 EEG electrode configuration; and the set of electrode position labels 147 on the linear rack can include a second sequence of discrete textual symbols highlighted in the range of discrete colors and arranged along the linear rack, as shown in FIG. 5, wherein each textual symbol in the second sequence of discrete textual symbols indicates a target lateral position of the second electrode 152 along the linear rack for a corresponding textual symbol—in the first sequence of discrete textual symbols—indicated by the band 121. Each adjustable band and each other adjustable electrode on each adjustable band can be similarly annotated with length scales and electrode position labels 147, respectively, to assist an EEG test administrator in rapidly adjusting the EEG headset 100 to a user's unique head geometry by adjusting the bands to fit the user's head and then shifting each sense electrode in its linear rack to match its electrode position label to the length value of its corresponding band.

Junction Electrodes

In one variation shown in FIGS. 1 and 3, the left junction 110 is configured for placement adjacent a left ear of the user, and the right junction 112 is laterally offset from the left junction 110 and configured for placement adjacent a right ear of the user when the adjustable EEG headset is worn on the head of the user. In this variation, a T3 electrode can be fixedly mounted to the left junction 110, and a T4 electrode can be fixedly mounted to the right junction 112.

Because the geometry of the left and right junctions 110, 112 and the user's ears and hair near the left and right junctions 110, 112 may visually obstruct these T3 and T4 electrodes and thus inhibit an EEG test administrator from easily observing contact between these electrodes and the user's scalp, the EEG headset 100 can also include: a left light element 170 adjacent the T3 electrode, facing inwardly from the left junction 110 toward the right junction 112, and configured to illuminate the T3 electrode adjacent a scalp of the user when the adjustable EEG headset is worn on the head of the user; and a right light element 170 adjacent the T4 electrode, facing inwardly from the right junction 112 toward the left junction 110, and configured to illuminate the T4 electrode adjacent the scalp of the user when the adjustable EEG headset is worn on the head of the user, as shown in FIG. 3. The EEG headset 100 (e.g., the controller 184) can therefore activate the left and right light elements 170 during a setup period preceding an EEG test and/or throughout the EEG test in order to illuminate the T3 and T4 electrodes, thereby better enabling the EEG test administrator to quickly visually observe these electrodes and make adjustments to these electrodes or to the band 121 to improve contact with the user's scalp.

Support Blocks

Each adjustable electrode (and each fixed electrode) can also include a spring element 149 between the sense electrode and the sliding element and configured to depress the electrode toward a user's head and to absorb variations in distances between the band 121 and users' scalps when the EEG headset 100 is worn by a variety of users.

In one implementation shown in FIGS. 2, 3, and 4, the EEG headset 100 further includes support blocks: arranged on each side of electrodes on the bands; configured to elevate the bands off of the scalp of the user and thus improve manual access to electrodes facing inwardly from these bands; and to rest on the head of a user and thus distribute the weight of EEG headset 100 on the user's head, which may be more comfortable for a user than smaller electrodes (such as with pronged tips) carrying the weight of the EEG headset 100 into the user's scalp. For example, the EEG headset 100 can include: a first support block 161 arranged on the first band 121 between the first electrode 140 and the second electrode 152, extending toward a median of a lateral axis coinciding with the left junction 110 and the right junction 112, and defining a first surface facing the lateral axis and configured to rest against a head of a user; and a second support block 162 arranged on the first band 121 adjacent the second electrode 152 laterally opposite the first support block 161, extending toward the median of the lateral axis, and defining a second surface facing the lateral axis and configured to rest against the head of the user. In this example, the support blocks can include solid or rigid hollow structures with soft (e.g., foam, rubber) surfaces configured to contact a user's head and to cushion the weight of the EEG headset 100 on the user's head.

In this implementation, the second electrode 152 can include: an electrode body 142 coupled to the first band 121; an electrode tip 144 coupled to the electrode body 142 opposite the first band 121, as described above; and a spring element 149 arranged inside the electrode body 142 and configured to bias the electrode tip 144 past the first surface and the second surface toward the median of the lateral axis, as shown in FIG. 8. In particular, the electrode tip 144 of the second element can extend inwardly past the soft surfaces of the support blocks by a minimal distance (e.g., approximately three millimeters) at full extension, and the spring element 149 can bias the second electrode 152 to full extension. When the EEG headset 100 is placed on a user's head, the tip of the second electrode 152 can fall against the user's scalp, and the weight of the EEG headset 100 over the second electrode 152 can compress the spring element 149 in the second electrode 152, thereby collapsing the second electrode 152 until the adjacent support blocks contact the user's scalp. The spring element 149 can thus compress the electrode tip 144 of the second electrode 152 against the user's scalp with substantially consistent force (e.g., within a narrow range of target electrode tip 144 forces or pressures); and the support blocks can carry (some of) the load of the EEG headset 100 into the user's head. Because the soft surfaces of the support blocks define larger surface areas than the second electrode 152, the support blocks can thus decrease local pressures of the EEG headset 100 on the user's scalp and yield improved comfort for the user.

In this implementation, the second electrode 152 can also include a shoulder 145 adjacent the electrode tip 144, such as defining a rim extending radially about the electrode body 142 aft of and coupled to the electrode tip 144, as shown in FIGS. 5 and 8. The spring element 149 can further support manual retraction of the electrode tip 144—via the shoulder 145—past the surfaces of the adjacent support blocks toward the first band 121 in order to separate the electrode tip 144 from the head of the user during lateral adjustment of the first electrode 140 on the first band 121. In particular, rather than maintaining contact between the electrode tip 144 of the second electrode 152 and the user's scalp while moving the second electrode 152 laterally along its electrode adjuster 141, while may be uncomfortable for the user and cause the electrode tip 144 to separate from the electrode body 142, an EEG test administrator may: grip the shoulder 145 between her thumb and forefinger (with the base of the thumb adjacent the first band 121); retract the second electrode 152 toward the first band 121 to separate the electrode tip 144 from the user's scalp; draw the second electrode 152 laterally to a target position—indicated by electrode position labels 147—on the electrode adjuster 141; and then release the shoulder 145. The spring element 149 can thus drive the electrode tip 144 forward and back into contact with the user's scalp and retain the electrode tip 144 in contact with the user's scalp within the target electrode tip 144 force range.

As described above and shown in FIG. 4, the electrodes can include replaceable electrode tips 144 of various geometries. The EEG headset 100 can therefore also include a kit of support blocks of various geometries (e.g., lengths) matched to the geometries of various electrode tips 144. For example, the electrode tip 144 of the second electrode 152 can be transiently coupled to the electrode body 142 of the second electrode 152 and can be configured for installation on the electrode body 142 in combination with installation of the first support block 161 and the second support block 162 on the first band 121 such that this electrode tip 144 extends inwardly just past the inner surfaces of the first and second support blocks 161, 162 when the second electrode 152 is at full extension with this electrode tip 144 installed. In this example, the EEG headset 100 can also include: a third support block defining a height greater than the height of the first support block 161 and interchangeable with the first support block 161 on the first band 121; a fourth support block 164 defining a height greater than the height of the second support block 162 and interchangeable with the second support block 162 on the first band 121; and including a second electrode 152 tip configured to transiently couple to the electrode body 142 of the second electrode 152, interchangeable with the electrode tip 144 on the electrode body 142 of the second electrode 152; defining a length greater than the electrode tip 144; and configured for installation on the electrode body 142 in combination with installation of the third support block and the fourth support block 164 on the first band 121. In particular, the heights of the third and fourth support blocks 163, 164 can be matched to the length of the second electrode 152 tip such that the longer second electrode 152 tip extends inwardly just past the inner surfaces of the third and fourth support blocks when the second electrode 152 is at full extension with the second electrode 152 tip installed. In this example, the support blocks can be snapped, fastened, or otherwise transiently connected to support block receptacles between electrodes on the bands.

Other electrodes on the EEG headset 100 can include similar spring elements 149 and shoulders 145, and the EEG headset 100 can include similar support blocks mounted to the ends adjacent these other electrodes. However, the EEG headset 100 can include any other type and geometry of electrode tips 144 and matched support blocks of any other material or geometry.

Furthermore, the adjustable electrode can include a slotted grommet arranged between the sliding element and the sense electrode. For example, the slotted grommet can be of a compressible material (e.g., silicone foam), configured to prevent ingress of debris into the ratchet mechanism, and configured to damp motion of the sense electrode relative to the band 121 and to retain the position of the sense electrode relative to the band 121 in order to reduce noise in a sense signal read from the sense electrode during an EEG test. Each adjustable electrode (and each fixed electrode) can additionally or alternatively include a screw element that, when adjusted by an EEG test administrator, drives the entire sense electrode (or the electrode tip 144 of the sense electrode exclusively) toward or away from the band 121, thereby enabling the EEG test administrator to tune a force applied by an electrode tip 144 to an adjacent surface of the users skin and to configure the EEG headset 100 for users having heads of different shapes and geometries.

However, an adjustable electrode within the EEG headset 100 can be of any other form and can be configured in any other way to locate a sense electrode across a variety of users' heads—of different shapes and sizes—according to the 10-20 EEG electrode configuration (or other EEG electrode placement standard). The EEG headset 100 can also include any other number and type of active or passive, dry or wet sense electrodes configured to output any other low- or high-impedance signal to a signal processor or controller 184 in the EEG headset 100, as described below.

Electrode Position Feedback

In this variation, the EEG headset 100 (and/or the native EEG test application executing on an external computing device) can detect global adjustments of the EEG headset 100 at each band and local adjustments at each adjustable electrode to confirm that the position of each adjustable electrode conforms to the 10-20 system, such as within a predefined tolerance (e.g., +/−five millimeters). The EEG headset 100 (or native EEG test application hosting an EEG portal on an external computing device connected to the EEG headset 100) can serve prompts to an EEG test administrator—in real-time—to adjust certain adjustable electrodes in order to bring the EEG headset 100 into alignment with the 10-20 system prior to start of an EEG test.

In one implementation, the first band 121 includes a band 121 potentiometer interposed between the first band 121 and the left (or right) junction, wherein the internal electrical resistance of the band 121 potentiometer changes as a function of an adjusted position of the first band 121, for example, as a function of a distance between a first end of the first band 121 and the left junction 110. In this implementation, the EEG headset 100 also includes: an F4 electrode adjuster supporting an F4 sense electrode proximal an F4F7 position on the first band 121; an F8 electrode adjuster supporting an F8 sense electrode proximal an F8 position on the first band 121; an F4F7 electrode potentiometer coupled to the first band 121 and to the F4F7 electrode adjuster and exhibiting a change in internal resistance as a function of the position of the F4F7 electrode adjuster on the first band 121; and an F8 electrode potentiometer coupled to the first band 121 and to the F8 electrode adjuster and exhibiting a change in internal resistance as a function of the position of the F8 electrode adjuster on the first band 121.

During setup, the controller 184 can sample the band 121, F4F7 electrode, and F8 electrode potentiometers and then implement methods and techniques described below to calculate: a length of the first band 121 based on a voltage (or internal resistance) read from the band 121 potentiometer; a position of the F4F7 electrode relative to the first band 121 based on a voltage (or internal resistance) read from the F4F7 electrode potentiometer; and a position of the F8 electrode relative to the first band 121 based on a voltage (or internal resistance) read from the F8 electrode potentiometer, such as based on a lookup table or set of parametric equations for each of these potentiometers. The controller 184 can then calculate a target position of the F4F7 electrode based on the length of the first band 121, such as a singular target position (e.g., in the form of a target voltage or resistance of the first electrode 140 potentiometer) or a target voltage range (e.g., in the form of a target voltage or resistance range of the first electrode 140 potentiometer) based on predefined rules of the 10-20 system. The controller 184 can implement similar methods and techniques to calculate a target position of the F8 electrode. The controller 184 can then compare the actual positions of the F4F7 and F8 electrodes to the target positions or target position ranges of the F4F7 and F8 electrodes to confirm that the F4F7 and F8 electrodes fulfill rules defined by the 10-20 system.

Alternatively, the controller 184 can: access a lookup table that links a voltage (or resistance) read from the band 121 potentiometer on the first band 121 directly to a singular target potentiometer voltage for each of the F4F7 and F8 electrode potentiometers; calculate a difference between the singular target potentiometer voltages and actual voltages read from the F4F7 and F8 potentiometers; and then directly confirm alignment of the F4F7 and F8 electrode to the 10-20 system if these differences do not exceed a threshold voltage difference representing a tolerance of the 10-20 system.

If the controller 184 confirms that one or both of the F4F7 and F8 electrodes are positioned outside of an acceptable range of positions on the first band 121 necessary to realize the 10-20 system, the controller 184 can transmit a notification to correct the position of the F4F7 and/or F8 electrodes to an external computing device connected to the EEG headset 100, such as to a computing device executing a native EEG test application hosting the EEG portal. For example, for the EEG headset 100 that includes symbolic position indicators adjacent each adjustable electrode, as described above, the EEG headset 100 can transmit to the connected computing device a notification to correct the position of the F4F7 electrode, including a target positional character (e.g., "5/10" or "E") at which to set the F4F7 electrode adjustor if the F4F7 electrode is determined to be outside of its acceptable positional range. In another example, the EEG headset 100 can transmit to the computing device a notification specifying an approximate physical distance and direction to shift the F4F7 electrode in order to realize the 10-20 system. In these examples, upon receipt of such a notification from the EEG headset 100, the native EEG test application can render this notification on a display of the computing device. The native EEG test application can additionally or alternatively update a virtual representation of the EEG headset 100 rendered on the computing device to indicate that the F4F7 electrode requires adjustment, such as by highlighting the F4F7 electrode in a virtual representation of the EEG headset 100 and inserting a directional arrow and target offset distance to shift the F4F7 electrode into alignment with the 10-20 system.

The EEG headset 100 can additionally or alternatively include light elements 170 (e.g., LEDs) arranged on the bands adjacent each adjustable electrode, and the controller 184 can update the state of each light element 170 to visually indicate directly on the EEG headset 100 which adjustable electrodes require repositioning to realize the 10-20 system. For example, the EEG headset 100 can include a first multicolor LED arranged on the first band 121 adjacent one end of the adjustment range of the F4F7 electrode and a second multicolor LED arranged on the first band 121 adjacent the opposite end of the adjustment range of the F4F7 electrode. The EEG headset 100 can then update the state of one of these multicolor LEDs to output a flashing "red" light to visually indicate a need to move the F4F7 electrode away from this LED and toward the opposing LED. Once the F4F7 electrode is correctly repositioned, the EEG headset 100 can update the first and second multicolor LEDs to output "green" light to visually indicate that the F4F7 electrode is properly positioned. Similarly, the EEG headset 100 can include a multicolor LED adjacent each adjustable electrode, and the EEG headset 100 can trigger each LED: to output a "red" color if the position of the adjacent electrode differs significantly from a target electrode position; to output a "yellow" color if the position of the adjacent electrode is just outside acceptable bounds of a target electrode position; and to output a "green" color if the position of the adjacent electrode is within acceptable bounds of a target electrode position.

The system can include similar arrangements of electrode potentiometers at other adjustable electrodes in the EEG headset 100, and the EEG headset 100 (and/or the native EEG test application executing on the connected computing device) can implement similar methods and techniques to confirm that the position of each adjustable electrode fulfills the 10-20 system. During setup, the EEG headset 100 can regularly sample these potentiometers to track the position of each adjustable electrode and provide feedback to the EEG test administrator in (near) real-time directly through the EEG headset 100 or through an EEG portal at the connected computing device until the EEG headset 100 is properly configured according to the 10-20 system (or other electrode placement standard). Furthermore, the EEG headset 100 (and/or the native EEG test application) can reject a request to start an EEG test at the EEG headset 100 until all electrodes in the EEG headset 100 are confirmed in their proper positions according to the 10-20 system. (Similarly, the EEG headset 100 and/or the native EEG test application can reject a request to start an EEG test at the EEG headset 100 until all electrodes specified as active in the upcoming EEG test or at least a threshold number of electrodes specified in the upcoming EEG headset are confirmed in their proper positions according to the 10-20 system, such as within a tolerance of three millimeters or 5%.) The EEG headset 100 (and/or the native EEG test application) can implement similar methods and techniques throughout the subsequent EEG test performed at the EEG headset 100 to confirm that adjustable electrodes within the band 121 remain in proper position on the user's head and to provide related notifications to the EEG test administrator in (near) real-time until the EEG test is complete.

However, each adjustable electrode and each band in the EEG headset 100 can include any other type of positional sensor arranged in any other way in the EEG headset 100 and configured to output a signal representative of the relative position of its corresponding electrode and the length of each band in the EEG headset 100. For example, rather than a linear potentiometer, each band can include a mechanical, optical, or magnetic optical encoder, such as in linear or rotational format.

Sense Electrode Contact Force

In this variation (and other variations described below), the EEG headset 100 can also include a pressure sensor interposed between each sense electrode and its corresponding band. For example, for each sense electrode, the EEG headset can include a conductive foam, diaphragm-type, or piezoelectric pressure sensor configured to output a signal representative of a force applied by the sense electrode to the user's skin. The EEG headset can thus sample each pressure sensor to confirm that each sense electrode is applying at least a minimum force (or pressure) to the user's skin, that each sense electrode is applying between a threshold minimum force and a threshold maximum force to the user's skin, and/or that all sense electrodes in the EEG headset are applying substantially similar forces (or pressures) to the user's skin. The EEG headset (or the native EEG test application executing on the connected computing device) can then serve prompts to the EEG test administrator to confirm that each sense electrode is properly depressed onto the user's skin and/or to prompt the EEG test administrator to tighten or loosen select electrodes in order to achieve these applied force targets before beginning the EEG test.

Contact Loss Feedback

The EEG headset 100 can additionally or alternatively include light elements 170 facing outwardly from the bands adjacent corresponding electrodes, and the controller 184 can selectively activate these light elements 170 during an EEG test in order to visually indicate to an EEG test administrator when an electrode has lost contact with the user's skin. For example, the EEG headset 100 can include a first light element 170 arranged on the first band 121 adjacent the first electrode 140 and facing outwardly from the first band 121; and the controller 184 can read a signal from the first electrode 140, characterize contact quality between the first electrode 140 and a scalp of a user (e.g., based on features in this signal or based on an output of a pressure sensor coupled to the first electrode 140), and selectively activate the first light element 170 in response to detecting improper contact between the first electrode 140 and the scalp of the user, as described in U.S. patent application Ser. No. 15/351,016.

Fixed Sense Electrodes

In one variation, rather than a single discrete electrode at each adjustable electrode position described below, the EEG headset includes a linear array of multiple discrete electrodes (hereinafter an "electrode array") fixedly coupled to a band 121, and the EEG headset 100 (e.g., the controller 184) or external computing device connected to the EEG headset 100 selectively activates one electrode in each electrode array that best realizes electrode placement rules of the 10-20 EEG electrode configuration (or other EEG electrode placement standard). For example, the EEG headset 100 includes one electrode array at each of the: F3 and F7F4 electrode positions along the first band 121; the F4F7 and F8 electrode positions along the second band 122; the C3 and C4 electrode positions along the third band 123; the P3 and P4 electrode positions along the fourth band 124; and the O1 and O2 electrode positions along the fifth band 125.

In this variation, each electrode array can include a set of discrete sense electrodes—as described above—packaged into a single block with the center-to-center distances between adjacent electrodes equal to or less than an electrode positional tolerance defined by the 10-20 system. For example, for an electrode positional tolerance of +/−five millimeters, the center-to-center distance between adjacent sense electrodes in one electrode array can be less than or equal to ten millimeters such that a particular electrode in an electrode array may fall within the positional tolerance of a target electrode positional—according to the 10-20 system and can then be activated accordingly, as described below. Furthermore, each sense electrode in an electrode array can include: a discrete substrate; a discrete set of electrically-conductive prongs extending from a first side of the substrate; and a discrete amplifier coupled to the substrate opposite the set of prongs and configured to amplify an electrical signal passing through the set of prongs. In particular, each electrode in an electrode array can be electrically isolated from other electrodes in the electrode array and can be selectively activated and deactivated independently of other electrodes in the same electrode array, such as by connecting and disconnecting the electrode from both power and ground terminals in the EEG headset 100.

Manual Activation

In one implementation, an EEG test administrator (or the user, etc.) enters a final adjustment position for each band—such as read from a scale arranged between the left and right junctions 110, 112 and each band—into the native EEG test application executing on the connected computing device; and the native EEG test application maps a final adjustment position for each band to known positions of electrode arrays along each band to select a particular electrode in each electrode array that best fulfills electrode position rules specified by the 10-20 system.

In one example, for the second band 122 that supports an F3 electrode array at the F3 position, an F4 electrode array at the F4 position, and a fixed Fz electrode at the Fz position, the native EEG test application accesses a lookup table or electrode map defining a position of each electrode in each of the F3 and F4 electrode arrays relative to the fixed Fz electrode. The native EEG test application can also retrieve a lookup table or parametric model (e.g., a mathematical equation) linking adjustment positions of the second band 122 to an effective distance between the fixed Fz electrode and the fixed T3 (or T4) electrode. The native EEG test application then divides this effective distance by two, selects a particular electrode from the electrode array at the F4 position that falls nearest this halved effective distance, activates this particular electrode in the F4 electrode array, and deactivates all other electrodes in the F4 electrode array. The native EEG test application can implement similar methods and techniques to activate a particular electrode in the F3 electrode array.

Alternatively, the native EEG test application can access a lookup table or other model that directly specifies electrodes in electrode arrays throughout the EEG headset 100 that meet electrode position rules of the 10-20 system for specific adjustment positions of each band. The native EEG test application can then implement similar methods and techniques described above to select specific electrodes in electrode arrays at the F7F4, F3 C3, C4, P3, P4, O1, and O2 positions along the first, third, fourth, and fifth bands. The native EEG test application can then push a command to activate these select electrodes back to the EEG headset 100, which can implement these electrode specifications during the subsequent EEG test.

Yet alternately, in this implementation, the native EEG test application can transmit final band adjustments—entered by the EEG test administrator into the native EEG test application—to the EEG headset 100, and a controller 184 within the EEG headset 100 can implement the foregoing methods and techniques locally to selectively activate and deactivate electrodes within electrode arrays throughout the EEG headset 100 based on these final band adjustments in order to achieve a best approximation of the 10-20 system (or other biosignal acquisition system) during the current EEG test.

Automatic Activation

Alternatively, each band in the EEG headset 100 can include a linear potentiometer interposed between the band 121 and the left (or right) junction, wherein the internal electrical resistance of each linear potentiometer changes as a function of the position of the band 121, for example, as a function of a distance from a first end of the band 121 to the left junction 110. The EEG headset 100 (e.g., a controller 184) can: sample linear potentiometers coupled to each band and transform voltages read from these linear potentiometers into adjustment positions of each band; and then transform a voltage read across each linear potentiometer (or a resistance of each potentiometer) into an adjustment position of the corresponding band, such as by passing the voltage read from the potentiometer into a lookup table or mathematical model. The controller 184 can then implement methods and techniques described above to select particular electrodes in each electrode array that best fit the 10-20 system. Alternatively, the EEG headset 100 can access a lookup table that directly maps a voltage read across each potentiometer (or a resistance of each potentiometer) to a particular electrode in each electrode array on the corresponding band, as described above. The EEG headset 100 can then activate these select electrodes and deactivate all other electrodes in the electrode arrays in the EEG headset 100 during the subsequent EEG test.

However, in this variation, each band can include a positional sensor of any other type, such as a mechanical, optical, or magnetic optical encoder, as described above.

Replacement Electrodes Tips

In one implementation, the sense electrodes include replaceable tips. For example, each sense electrode can include a magnetic element 143 adjacent or behind a terminal electrically coupled to an input of an amplifier within the sense electrode and configured to retain a removable electrode tip containing a ferrous element 148. In this example, the magnetic element 143 in each sense electrode can be configured to retain any of an elastic bristle electrode tip; a rigid prong electrode tip; a flat contact disk electrode tip; a domed contact disk electrode tip; and/or any other type or geometry of electrode tip. Alternatively, each electrode can include a mechanical electrode tip retainer (e.g., a latch) configured to accept, retain, and then release an electrode tip.

In the variation described above in which the EEG headset 100 includes electrode arrays, each electrode array can similarly include a magnetic element 143 or other mechanical feature configured to retain a removable array of like electrode tips 144 containing a ferrous element 148 or other mating feature. In this example, each array of electrode tips 144 can include multiple discrete and electrically isolated electrode tips 144 arranged in a single assembly that can be installed and then removed from an electrode array.

However, each electrode or electrode array in the EEG headset 100 can be configured to transiently receive electrode tips 144 (e.g., replacement electrode tips) of any other type or geometry.

Control Module

In one variation shown in FIGS. 1 and 3, the EEG headset 100 further includes a controller 184, a signal processor, a battery, and/or a wireless communication module 183 arranged within a control module 180 coupled to or physically coextensive with the fifth band 125 (or with the central body described above). Generally, the control module 180 can contain various controls, communication, and power components of the EEG headset 100 and can be mounted to or integrated into the rearmost (e.g., the fifth) band in order to: maintain access to various related controls and ports; limiting obstruction to the user's vision and movements; and/or to counterbalance the EEG headset 100, thereby improving stability of the EEG headset 100 during an EEG test.

For example, the EEG headset 100 can include: a fifth band 125 spanning the left junction 110 and the right junction 112 and configured to extend proximal a base of a skull of a user when the EEG headset 100 is worn on the head of the user; a housing 181 arranged on the fifth band 125; and a battery 182, a controller 184, and a wireless transmitter 183 arranged in the housing 181, as shown in FIGS. 1 and 3. In this example, the controller 184 can be configured to read a set of analog sense signals from active electrodes within the EEG headset 100 (e.g., the first electrode 140, the second electrode 152, the third electrode 153, etc.) during an EEG test performed at the EEG headset 100, such as described in U.S. patent application Ser. No. 15/351, 016. In this example, the wireless transmitter 183 can wirelessly transmit digital representations of the set of analog sense signals recorded by the controller 184, such as to a remote database via a local hub or wireless router in real-time during the EEG test.

The EEG headset 100 can also include a set of wires passing from the control module 180 (or the fifth band 125) to sense electrodes in other bands throughout the EEG headset 100 and configured to communicate sense signals from the sense electrodes back to the controller 184 and/or signal processor.

However, the control module 180 can be arranged within or distributed across the EEG headset 100 in any other form or format. Elements of the control module 180 can also be integrated into the connected computing device (e.g., the controller 184 or processor), and sensor signals and control commands can be communicated between the connected computing device and the EEG headset 100 via a wired or wireless connection.

Driven and Reference Electrodes

The EEG headset 100 can also include a reference electrode and a driven electrodedrive electrode (or a "driven right leg" electrode), as described in U.S. patent application Ser. No. 15/351,016. Like each sense electrode, the reference electrodedrive electrode can define a dry EEG sensor, and can include a substrate; an electrode tip extending from or (transiently) electrically coupled to a first side of the substrate; and an amplifier coupled to the substrate opposite the electrode tip and configured to amplify an electrical signal detected by the electrode tip. In this implementation, the amplifier can output a low-impedance reference signal that follows a high-impedance reference signal read at the electrode tip to the signal processor or controller 184 described above. However, the reference electrodedrive electrode can include any other type of dry- or wet-type EEG electrode and can output any other signal to the signal processor or controller 184. The driven electrodedrive electrode can include a fixed or interchangeable electrode tip of a similar geometry.

In one implementation, the drive electrode is fixedly mounted to the first band 121 between sense electrodes in the FP1 and FP2 positions. Alternatively, the driven electrodedrive electrode is can be mounted to a beam that pivots or extends downwardly from the right junction 112 or from the right side of the control module 180; the beam can be configured to locate and depress the driven electrodedrive electrode onto the user's skin, such as below the user's right ear. The reference electrode can be similarly mounted to a beam that pivots or extends downwardly from the left junction 110 or from the left side of the control module 180 to locate and depress the reference electrode onto the user's skin, such as below the user's left ear.

Alternatively, the EEG headset 100 can include a sixth band configured to drop (e.g., pivot downwardly) from the fifth band 125, and the driven and reference electrodes can be mounted to the sixth band. In yet another implementation, the driven and reference electrodes can be coupled to loose, elastic wires configured to (transiently) plug into the control module 180 and can be configured to stick onto or to be taped onto the user's skin substantially remotely from the user's scalp. However, the driven and reference electrodes can be arranged within the EEG headset 100 in any other way.

Optical Detector

In one variation, the EEG headset 100 further includes an optical detector 190 facing outwardly from the front band (e.g., configured to lie across a user's forehead) and configured to output a signal that follows variations in local light intensity. In this variation, the controller 184 can record a first EEG signal output by a first electrode 140 in the EEG headset 100 to a first sense channel and record a second EEG signal output by a second electrode 152 in the EEG headset 100 to a second sense channel; record a third EEG signal output by the third electrode 153 in the EEG headset 100 to a third sense channel; etc., as described above. The controller 184 can also record a signal output by the optical detector 190 to a strobe channel synchronized to the first sense channel, the second sense channel, and the third sense channel.

Therefore, in this variation, the optical detector 190 can output a signal that follows the intensity of light output by an active strobe light (or "photic stimulator") facing a user during an EEG test; and the controller 184 can record the output of the optical detector 190 to a strobe channel temporally synchronized to sense channels for each sense electrodes in the EEG headset 100. For example, during each sampling period (e.g., at a rate of 500 Hz) during an EEG test, the controller 184 can: write digital representations of the voltage at each sense electrode during the current sampling period to its corresponding sense channel; read the analog output of the optical detector 190 during the current sampling period; write a HI (or "1") value to the strobe channel if the value of the analog output signal of the optical detector 190 exceeds a threshold value; and write a LO (or "0") value to the strobe channel if the value of the analog output signal of the optical detector 190 is less than a threshold value. In this example, the controller 184 can repeat this process for each sampling period to record synchronized, temporal representations of electrical activity at various regions of the user's brain and strobe light activity near the user over the duration of an EEG test.

Tape

In one variation, the EEG headset 100 accompanies a measurement tape. In this variation, the measurement tape can include a first side containing a centerline measurement scale; and a second side containing a circumferential measurement scale. During setup, an EEG test administrator can run the measurement tape—first side facing up—from the base of a user's skull to the user's forehead, read a value from the measurement tape representing this centerline distance, and then set band adjusters in the second, third, and fourth bands in the EEG headset 100 such that their corresponding scales read this value. The EEG test administrator can thus adjust the second, third, and fourth bands—that extend over the top of the user's skull—to initial positions that may accept the user's upper skull shape and size and that may approximate final adjustment settings of the EEG headset 100 for the user, as shown in FIG. 7.

The EEG test administrator can then run the measurement tape—second side facing out—from around the circumference of the user's skull just above the user's ears, read a value from the measurement tape representing this circumferential distance, and then set band adjusters in the first and fifth bands in the EEG headset 100 such that their corresponding scales read this value. The EEG test administrator can thus adjust the first and fifth bands—that wrap around the circumference of the user's skull—to initial positions that may accept the full breadth and length of the user's head and that may approximate final adjustment settings of the EEG headset 100 for the user.

Once initial adjustment positions of the first, second, third, fourth, and fifth bands of the EEG headset 100 are thus set based on values read from the measurement tape, the EEG test administrator can place the EEG headset 100 onto the user's head and make final adjustments to the bands via the band adjusters to achieve proper contact between the sense electrodes and the user's skin.

Electrode Tips

Figure 10A:
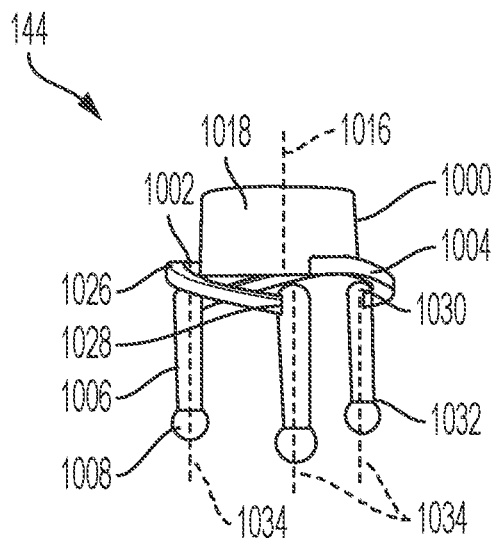
FIG. 10A illustrates a side view of a variation of a detachable electrode tip.
Figure 16:
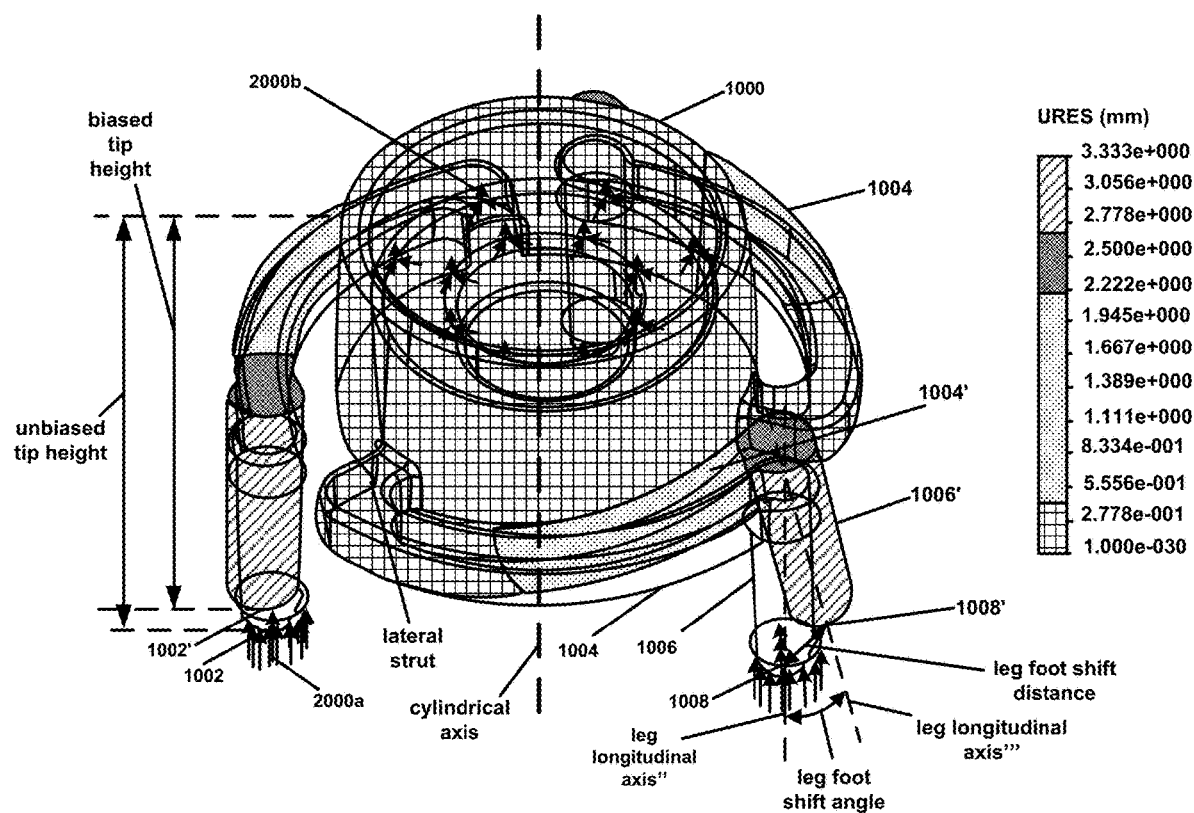
FIG. 16 is a computer-generated graphic illustrating the deflection of the electrode legs of a variation of an electrode tip in response to compressive forces applied to the electrode tip.
Figure 17:
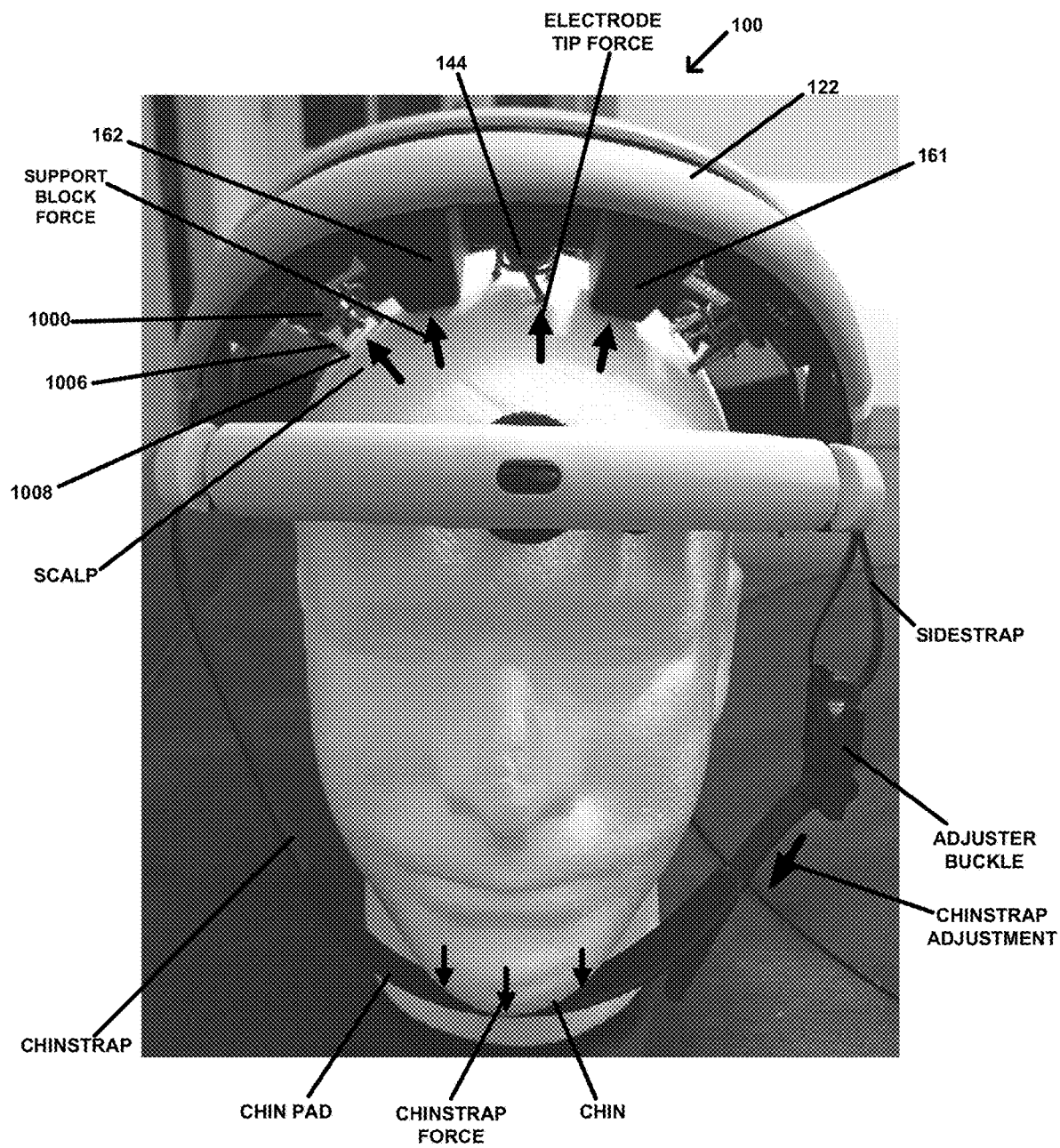
FIG. 17 is a black-and-white image showing deflection of the electrode legs of several electrode tips coupled to a variation of a headset when the headset is worn by a model user and at least one of a side-strap and chinstrap are tightened.
Figure 18:
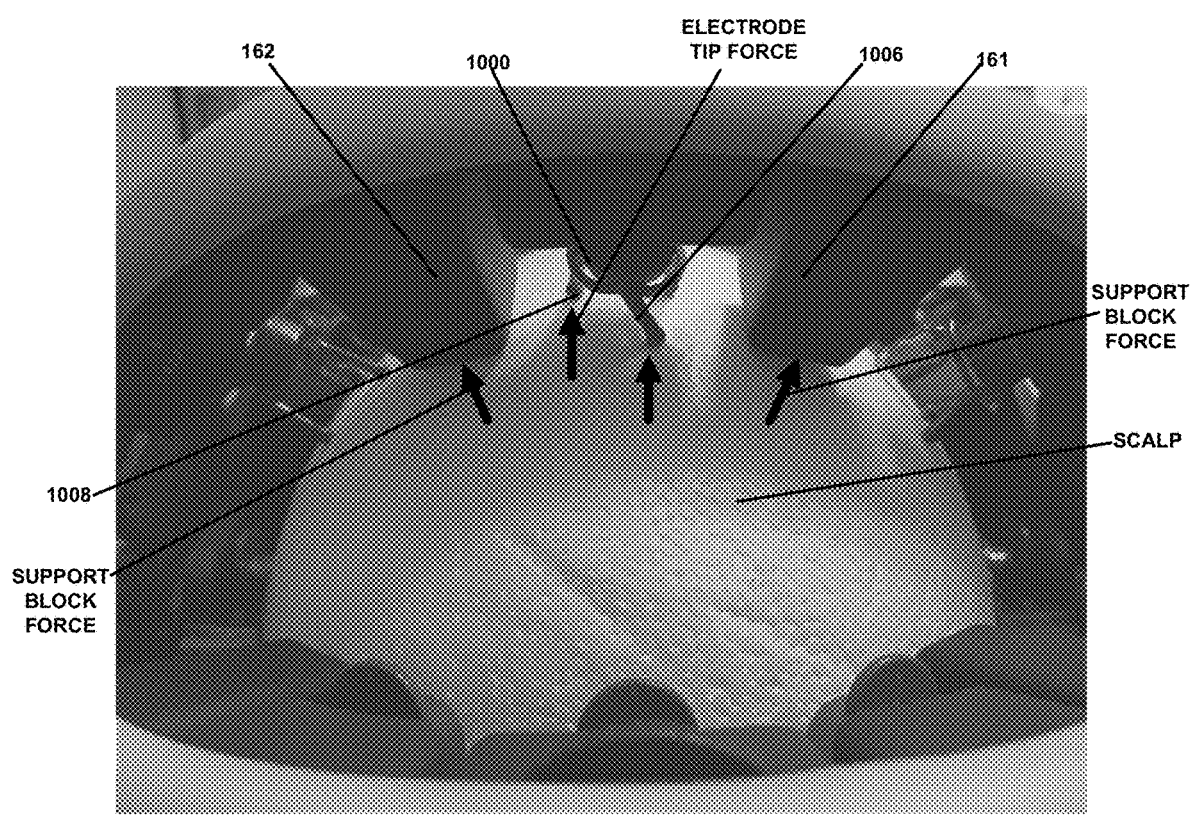
FIG. 18 is a black-and-white image showing a close-up view of the deflection of the electrode legs of one of the electrode tips shown in FIG. 17.

FIG. 10A illustrates that the electrode tip 144 can comprise an electrode tip body 1000, a lateral strut 1002 extending laterally from the electrode tip body 1000, one or more electrode arms 1004 extending from each of the lateral struts 1002, one or more deflectable electrode legs 1006 coupled to each of the one or more electrode arms 1004, and one or more electrode feet 1008 coupled to each of the one or more electrode legs 1006. The electrode legs 1006 can have a non-biased configuration (as shown in FIG. 10A) and a splayed configuration (as shown in FIGS. 16, 17, and 18). The electrode legs 1006 can be configured to spread out into the splayed configuration when a compressive force is applied to the electrode tip 144 including the electrode tip body 1000 and the electrode legs 1006. In other instances, the electrode legs 1006 can be configured to splay inwards into an inward splayed configuration when a compressive force is applied to the electrode tip body 1000 and the one or more electrode legs 1006.

The electrode tip body 1000, the lateral struts 1002, the electrode arms 1004, the electrode legs 1006, the electrode feet 1008, or a combination thereof can comprise or be made in part of a conductive material. The electrode tip body 1000, the lateral struts 1002, the electrode arms 1004, the electrode legs 1006, the electrode feet 1008, or a combination thereof can be made of a polymeric material, a metallic material, or a composite thereof. The electrode tip body 1000, the lateral struts 1002, the electrode arms 1004, the electrode legs 1006, the electrode feet 1008, or a combination thereof can comprise or be made of a polymeric material having conductive ions (e.g., silver/silver chloride), nanoparticles, or particles embedded, imbued, intermingled, or impregnated within the polymeric material. For example, the electrode tip body 1000, the lateral struts 1002, the electrode arms 1004, the electrode legs 1006, the electrode feet 1008, or a combination thereof can comprise or be made in part of nylon, a fiber-impregnated polymer, copper, silver, a metal oxide, or a combination thereof. The entire electrode tip 144 can be injection molded or parts of the electrode tip 144 including any of the electrode tip body 1000, the lateral struts 1002, the electrode arms 1004, the electrode legs 1006, and the electrode feet 1008 can be injection molded. The entire electrode tip 144 can be injection molded or parts of the electrode tip 144 including any of the electrode tip body 1000, the lateral struts 1002, the electrode arms 1004, the electrode legs 1006, and the electrode feet 1008 can also be cast molded using a prefabricated cast.

The electrode tip body 1000 can be substantially cylindrical. The electrode tip body 1000 can also be substantially cuboidal, pyramidal, rhomboid, spherical, or a combination thereof.

Figure 10B:
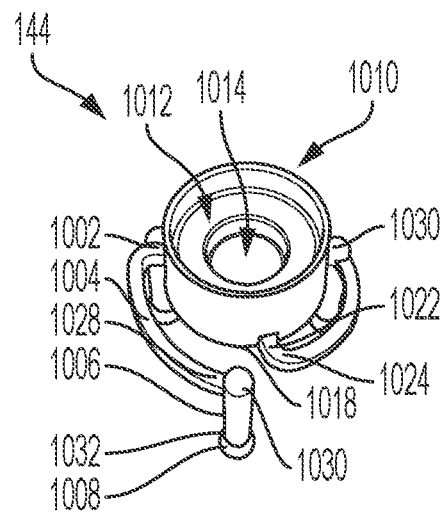
FIG. 10B illustrates a top perspective view of the detachable electrode tip.

FIG. 10B illustrates that the electrode tip body 1000 can have a cup-shaped portion surrounding a hollow center, divot, or void 1010. The cup-shaped portion can be defined along a top or proximal portion of the electrode tip body 1000. The void 1010 or divot can be substantially cylindrical-shaped, dome-shaped or shaped as a hemisphere, cuboidal-shaped, ovoid-shaped, ellipsoid-shaped, pyramidal-shaped, rhomboid-shaped, or a combination thereof. The void 1010 can extend partially into a top or proximal portion of the electrode tip body 1000. The void 1010 can comprise a first void portion 1012 and a smaller second void portion 1014 set within the first void portion 1012. For example, the first void portion 1012 can have a first void diameter and the second void portion 1014 can have a second void diameter shorter in length than the first void diameter. The first void portion 1012 can be substantially concentric with the second void portion 1014. The second void portion 1014 can extend further into the electrode tip body 1000 than the first void portion 1012.

As previously discussed, the electrode body 142 can comprise a first ferromagnetic component (e.g., the magnetic element 143, see FIG. 8). The first ferromagnetic component can be positioned at a distal or terminal end of the electrode body 142. For example, the first ferromagnetic component can be positioned distal or beyond the shoulder 145 of the electrode. The first ferromagnetic component (e.g., the magnetic element 143) can be partially encased or surrounded by part of the electrode body 142. The first ferromagnetic component can be coupled to the electrode body 142 by adhesives (e.g., conductive adhesives), an interference fit, latches, clips, or a combination thereof.

The electrode tip 144 can comprise a second ferromagnetic component (e.g., the ferrous element 148, see FIG. 8). The second ferromagnetic component can be complementary to the first ferromagnetic component such that the first ferromagnetic component can magnetically couple to the second ferromagnetic component when the first ferromagnetic component is positioned or placed in proximity to the second ferromagnetic component.

The second ferromagnetic component can be encased within a portion of the electrode tip body 1000. The second ferromagnetic component can be positioned or secured within part of the void 1010 such as within the second void portion 1014. The second ferromagnetic component (e.g., the ferrous element 148) can also be embedded or housed within the electrode tip body 1000 immediately below (i.e., vertically inferior to) the second void portion 1014.

The electrode tip 144 can detachably or removably couple to the electrode body 142 when the cup-shaped portion of the electrode tip body 1000 is pushed onto or otherwise biased toward the first ferromagnetic component. The void 1010 or hollow center defined by the cup-shaped portion can be configured to temporarily house or encompass the first ferromagnetic component. For example, the first void portion 1012 can surround or cup over at least part of the first ferromagnetic component. By doing so, the second ferromagnetic component can be biased or brought closer to the first ferromagnetic component and the electrode tip 144 can be magnetically coupled to the electrode body 142.

The first ferromagnetic component can comprise or be made in part of a permanent magnet, an electropermanent magnet, a ferromagnetic metal or ferrous metal, or a combination thereof. The second ferromagnetic component can comprise or be made in part of a permanent magnet, an electropermanent magnet, a ferromagnetic metal or ferrous metal, or a combination thereof. For example, the first ferromagnetic component can be a permanent magnet and the second ferromagnetic component can be a ferromagnetic or ferrous metal configured to magnetically couple to the permanent magnet. Alternatively, the first ferromagnetic component can be a ferromagnetic or ferrous metal and the second ferromagnetic component can be a permanent magnet configured to magnetically couple to the ferromagnetic or ferrous metal. At least part of the electrode tip body 1000 can also be made of a ferromagnetic material.

Figure 10C:
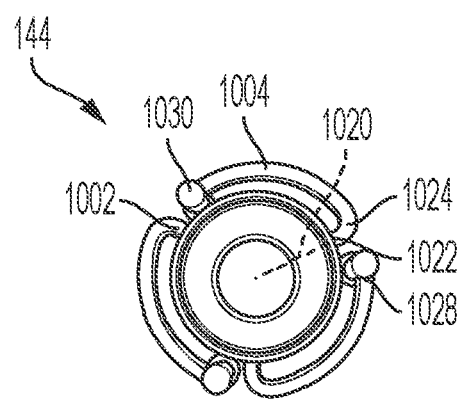
FIG. 10C illustrates a top plan view of the detachable electrode tip.

FIG. 10C illustrates that the lateral struts 1002 can extend radially (with respect to a longitudinal axis 1016 (see FIG. 10A) or cylindrical axis of the electrode tip body 1000) out from an outer surface 1018 (see FIGS. 10A, 10B, and 10D) of the electrode tip body 1000.

The lateral struts 1002 can extend out from the outer surface 1018 at an extension angle relative to a radius 1020 of the electrode tip body 1000. The extension angle can be from about 10 degrees to about −10 degrees (for example about 10 degrees, about 0 degrees, or about −10 degrees). The lateral struts 1002 can have the same cross-sectional shape and area as the electrode arms 1004 coupled to or most proximal to the lateral struts 1002. For example, the lateral struts 1002 can have a substantially rectangular cross-sectional shape, circular cross-sectional shape, triangular cross-sectional shape, rhombus cross-sectional shape, oval or elliptical cross-sectional shape, or a combination thereof.

As shown in FIGS. 10A-10D, the one or more electrode arms 1004 can be coupled to the outer surface 1018 of the electrode tip body 1000 via the lateral struts 1002. Although not shown in FIGS. 10A-10D, it is contemplated by this disclosure that the electrode arms 1004 can also be coupled directly to the outer surface 1018 of the electrode tip body 1000.

Although FIG. 10A-10D depict three electrode arms 1004 coupled to the electrode tip body 1000 (via lateral struts 1002), it is contemplated by this disclosure that four, five, or six or more electrode arms 1004 can be coupled to the electrode tip body 1000.

Figure 10D:
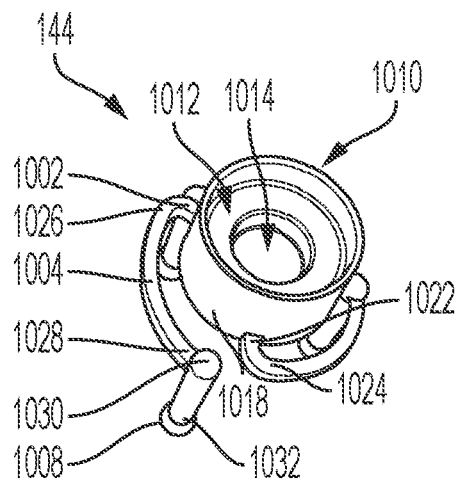
FIG. 10D illustrates another top perspective view of the detachable electrode tip.

The lateral struts 1002 (or the electrode arms 1004 if the electrode arms 1004 are coupled directly to the electrode tip body 1000) can be positioned or arranged evenly, uniformly, or equidistantly along the circumference of the electrode tip body 1000 when the electrode tip body 1000 has a substantially circular cross-section as shown in FIGS. 10B, 10C, and 10D. For example, the electrode tip 144 can comprise three lateral struts 1002 with each of the lateral struts 1002 coupled to an electrode arm 1004. For example, the electrode tip 144 can include a first lateral strut, a second lateral strut, and a third lateral strut. The first lateral strut can be coupled to the electrode tip body 1000 at a first attachment position, the second lateral strut can be coupled to the electrode tip body 1000 at a second attachment position, and the third lateral strut can be coupled to the electrode tip body 1000 at a third attachment position. Although three lateral struts 1002 are shown in FIGS. 10A to 10D, it is contemplated by this disclosure that any number of lateral struts 1002, electrode arms 1004, and electrode legs 1006 can be coupled to or extend from the electrode tip body 1000 (including two lateral struts 1002, four lateral struts 1002, five lateral struts 1002, six lateral struts 1002, seven lateral struts 1002, eight lateral struts 1002, etc.).

A circumferential length separating the first attachment position from the second attachment position can be equal to the circumferential length separating the first attachment position from the third attachment position. In addition, the circumferential length separating the second attachment position from the third attachment position can be equal to the circumferential length separating the first attachment position from the second attachment position. The lateral struts 1002 can also be positioned non-uniformly along the circumference of the electrode tip body 1000 such that the circumferential lengths separating the lateral struts 1002 from one another are not equal.

The lateral struts 1002 (or the electrode arms 1004 if the electrode arms 1004 are coupled directly to the electrode tip body 1000) can be coupled along a bottom portion or base of the electrode tip body 1000. The lateral struts 1002 (or the electrode arms 1004 if the electrode arms 1004 are coupled directly to the electrode tip body 1000) can also be coupled to a mid-portion of the electrode tip body 1000 or at a midpoint along a height or vertical length of the electrode tip body 1000. The lateral struts 1002 (or the electrode arms 1004 if the electrode arms 1004 are coupled directly to the electrode tip body 1000) can also be coupled to a top-portion or upper rim of the electrode tip body 1000.

The lateral struts 1002 can have a straight segment 1022 and a curved segment 1024 (or a segment having a curvature or radius). The straight segment 1022 can be a portion or segment of the lateral strut 1002 most laterally proximal to the electrode tip body 1000. The straight segment 1022 can have a substantially uniform cross-section. The straight segment 1022 can jut out normally or orthogonally from the outer surface 1018 of the electrode tip body 1000.

The curved segment 1024 can be a portion or segment of the lateral strut 1002 most proximal to the electrode arm 1004. All of the lateral struts 1002 coupled to the electrode tip body 1000 can have curved segments 1024 with the same curvature or radius. In some variations, at least one of the lateral struts 1002 can have a curved segment 1024 with a different shaped curvature or different radius than at least one of the other lateral struts 1002.

Each of the lateral struts 1002 can have a strut length dimension measured from an end of the lateral strut 1002 coupled to or extending from the outer surface 1018 of the electrode tip body 1000 to another end of the lateral strut 1002 coupled to the electrode arm 1004. The strut length dimension can be between approximately 1.0 mm to 10.0 mm (e.g., about 1.0 mm, about 5.0 mm, or about 10.0 mm). In other variations, the strut length dimension can be greater than 10.0 mm or less than 1.0 mm.

Each of the electrode arms 1004 can be coupled to or extend from the curved segment 1024 of the lateral strut 1002. The electrode arms 1004 can curve in a spiral pattern or trajectory. The electrode arms 1004 can curve or spiral in a clockwise or left-handed rotational direction, a counterclockwise right-handed rotational direction, or a combination thereof. For example, as shown in FIG. 10C, the electrode arms 1004 can curve or spiral in a counterclockwise or right-handed rotational direction when viewing the electrode tip 144 from a top plan view or top-down view. Although not shown in the figures, it is contemplated by this disclosure that at least one of the electrode arms 1004 can spiral or curve in a different rotational direction than at least one of the other electrode arms 1004.

As shown in FIGS. 10A-10D, the electrode arms 1004 can have a strut connecting end 1026 (or a proximal arm end) and a leg connecting end 1028 (or a distal arm end). The electrode arm 1004 can curve or rotate in a downward pitched or descending helical manner or trajectory such that the leg connecting end 1028 (or the distal arm end) is vertically lower or below the strut connecting end 1026 (or the proximal arm end). In other variations shown in FIGS. 12A and 12B, the electrode arms 1004 can curve or rotate along one transverse or horizontal plane such that the vertical position of the strut connecting end 1026 (or the proximal arm end) and the leg connecting end 1028 (or the distal arm end) do not differ (e.g., substantially equal) or differ only slightly (e.g., less than 0.5 mm apart).

FIGS. 10A-10D also illustrate that at least one electrode leg 1006 can be coupled to the leg connecting end 1028 of each of the electrode arms 1004. Each of the electrode legs 1006 can have an arm proximal end 1030 and a foot distal end 1032. The arm proximal end 1030 can refer to an end of the electrode leg 1006 most proximal or nearest to the leg connecting end 1028 of the electrode arm 1004. The foot distal end 1032 can refer to an end of the electrode leg 1006 opposite the arm proximal end 1030 and most proximal or nearest to the electrode foot 1008.

As shown in FIGS. 10A-10D, the arm proximal end 1030 of the electrode leg 1006 can be substantially dome-shaped or shaped as a hemisphere. The arm proximal end 1030 can also be substantially cuboidal, pyramidal, ovoid, ellipsoid, or a combination thereof. At least part of the arm proximal end 1030 of the electrode leg 1006 can extend past or vertically above the leg connecting end 1028 of the electrode arm 1004. In other variations, the arm proximal end 1030 of the electrode leg 1006 can be substantially flat or be flush with the leg connecting end 1028 of the electrode arm 1004 (as shown in FIGS. 16, 27A-27C, 28A, 29, and 30).

As shown in FIGS. 27A-27C, 28A, 29, and 30, the arm proximal end 1030 of the electrode leg 1006 can be angled or sloped with respect to a horizontal or transverse orientation plane. The arm proximal end 1030 of the electrode leg 1006 can be angled or sloped to match the angle or slope of the distal end of the electrode arm 1004 as the electrode arm 1004 curves or rotates in a downward pitched or descending helical trajectory.

The segment of the electrode leg 1006 in between the arm proximal end 1030 and the foot distal end 1032 can be substantially cylindrical-shaped, cuboid-shaped, or a combination thereof. For example, the segment of the electrode leg 1006 in between the arm proximal end 1030 and the foot distal end 1032 can have a uniform cross-sectional shape throughout the entire length of the segment. Although not shown in the figures, it is contemplated by this disclosure that the segment of the electrode leg 1006 in between the arm proximal end 1030 and the foot distal end 1032 can have a non-uniform cross-sectional shape or a varying cross-sectional shape. For example, the segment of the electrode leg 1006 in between the arm proximal end 1030 and the foot distal end 1032 can be shaped substantially as a conic, a frustoconic, a pyramid, a reverse-pyramid, or a combination thereof.

As shown in FIG. 10A, each of the electrode legs 1006 can have a leg longitudinal axis 1034. The leg longitudinal axis 1034 can be used to orient the position of the electrode leg 1006 in space and relative to other electrode legs 1006. For example, when little or no force is applied to the electrode tip body 1000 by the spring element 149 (either directly or indirectly via other intervening elements) and the scalp of the headset user, the electrode legs 1006 can be oriented substantially parallel to one another such that the longitudinal axis 1034 of each of the electrode legs 1006 is substantially parallel with one another and with the longitudinal axis 1016 of the electrode tip body 1000 when the electrode legs 1006 are in the non-biased configuration. However, when force is applied to the electrode tip body 1000 by the spring element 149 (either directly or indirectly via other intervening elements) and the scalp of the headset user, the electrode legs 1006 can be deflected or splayed out into the splayed configuration (see FIGS. 16, 17, 18, and 27C) such that the leg longitudinal axes 1034 are no longer parallel (or non-parallel) with one another or no longer parallel (or non-parallel) with the longitudinal axis 1016 of the electrode tip body 1000. Deflection and displacement of the electrode legs 1006 will be discussed in more detail in the following sections. In other instances, the electrode legs 1006 can be configured to splay inwards into an inward splayed configuration when a compressive force is applied to the electrode tip body 1000 and the one or more electrode legs 1006.

FIGS. 10A-10D also illustrate that the foot distal end 1032 of each of the electrode legs 1006 can be connected or otherwise coupled to an electrode foot 1008. The electrode foot 1008 can be substantially spherical, cuboidal, conical, frustoconical, oval, pyramidal, or a combination thereof. The electrode foot 1008 can also be a nub or cap positioned at the foot distal end 1032 of the electrode leg 1006. The electrode foot 1008 can also terminate in a pointed tip. When the electrode foot 1008 is shaped substantially as a sphere, a diameter of the sphere can be greater than a diameter or width of the electrode leg 1006. The larger size or contact footprint of the electrode foot 1008 can increase the comfort of the EEG headset 100 on the user's head. The shape of the electrode foot 1002 can be designed to allow the electrode foot 1002 to slide along the scalp or skin of a user, push hair away, and enable better contact with the scalp or skin of the user when the compressible and resilient electrode tip 144 is compressed against the scalp or skin.

Figure 11A:
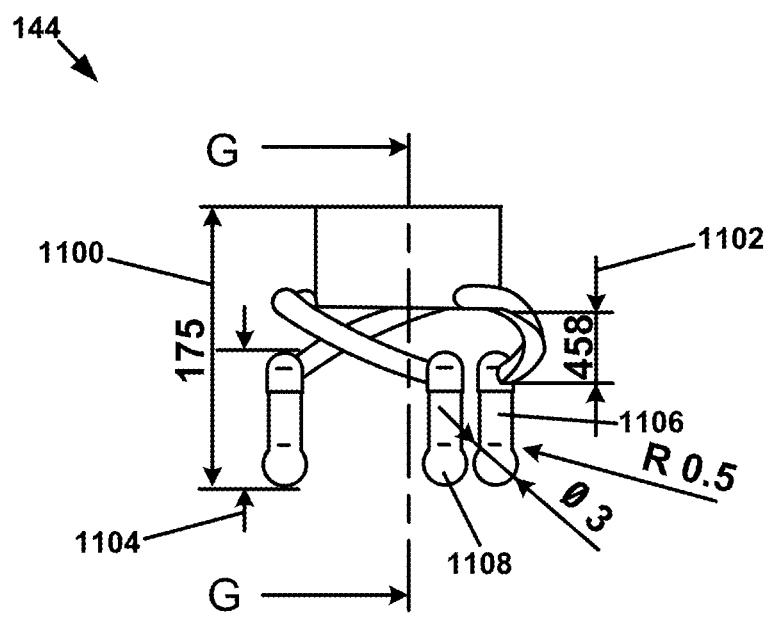
FIG. 11A is a side view of a schematic of a variation of a detachable electrode tip.

FIG. 11A illustrates that the electrode tip 144 can have an electrode tip height dimension 1100, an arm height dimension 1102, and a leg-foot height dimension 1104. In addition, FIG. 11A illustrates that when the electrode foot 1008 is substantially spherical-shaped, the electrode foot 1008 can have a foot diameter 1106. The electrode foot 1008 can also be substantially ovoid-shaped, ellipsoid-shaped, bulbous-shaped, teardrop-shaped, or a combination thereof.

The electrode legs 1006 can be shaped as elongate rods or cylinders. The electrode legs 1006 can also be shaped as elongate cuboids, conics, frustoconics, pyramids or polygonal pyramids, helices, or a combination thereof. When the electrode legs 1006 are shaped as elongate rods or cylinders, each of the electrode legs 1006 can have a leg diameter and a leg radius 1108.

The leg radius 1108 can be a radius of the electrode leg 1006 when the electrode leg 1006 is substantially cylindrical-shaped. The leg radius 1108 can be between about 0.25 mm and 2.0 mm (e.g., about 1.5 mm). The leg radius 1108 can also be between about 2.0 mm and 3.0 mm. The leg radius 1108 can also be between about 3.0 mm and 5.0 mm. The leg diameter can be between about 0.50 mm and 4.0 mm (e.g., about 3.0 mm). The leg diameter can also be between about 4.0 mm and 6.0 mm. The leg diameter can also be between about 6.0 mm and 1.0 cm.

The electrode tip body 1000 can also have a tip body diameter or a body radius 1020 (see FIG. 10C) when the electrode tip body 1000 is shaped as a cylinder. As shown if FIGS. 10A-10D and 11A-11B, the tip body diameter can be greater than the leg diameter. For example, a ratio of the leg diameter to the tip body diameter can be between about 1:2 and 1:10 (e.g., 1:4). For example, the leg diameter can be about 3.0 mm and the tip body diameter can be about 12.0 mm. The resiliency of the electrode tip 144 (i.e., the ability of the electrode legs 1006 to recover its original non-biased configuration from the splayed configuration) can be attributed to this ratio.

The electrode tip height dimension 1100 can be a total height of the entire electrode tip 144 measured from a top of the electrode tip body 1000 to the distal end of the electrode foot 1008. The electrode tip height dimension 1100 can be between approximately 10.0 mm to 20.0 mm (e.g., about 17.5 mm). In other variations, the electrode tip height dimension 1100 can be between approximately 5.0 mm and 10.0 mm. In additional variations, the electrode tip height dimension 1100 can be between approximately 20.0 mm and 50.0 mm.

The arm height dimension 1102 can be a pitch height or turn height of the electrode arm 1004 measured from a strut connecting end 1026 to the leg connecting end 1028 of the electrode arm 1004. The arm height dimension 1102 can be between approximately 2.0 mm to 5.0 mm (e.g., about 4.58 mm). In other variations, the arm height dimension 1102 can be between approximately 5.0 mm and 10.0 mm. In additional variations, the arm height dimension 1102 can be between approximately 10.0 mm and 20.0 mm.

The leg-foot height dimension 1104 can be a pitch height or turn height of the electrode arm 1004 measured from the arm proximal end 1030 of the electrode arm 1004 to the distal end of the electrode foot 1008. The leg-foot height dimension 1104 can be between approximately 10.0 mm to 15.0 mm. In other variations, the leg-foot height dimension 1104 can be between approximately 5.0 mm and 10.0 mm. In additional variations, the leg-foot height dimension 1104 can be between approximately 15.0 mm and 30.0 mm.

The foot diameter 1106 can be a diameter of the electrode foot 1008 when the electrode foot 1008 is substantially spherical shaped. The foot diameter 1106 can be between approximately 1.0 mm and 5.0 mm (about 3.0 mm). The foot diameter 1106 can also be between approximately 0.2 mm and 1.0 mm. The foot diameter 1106 can also be between approximately 5.0 mm and 10.0 mm. As shown in FIG. 11A, the foot diameter 1106 can be greater than the leg diameter of each of the electrode legs 1006. When the electrode foot 1008 is substantially ovoid-shaped, ellipsoid-shaped, bulbous-shaped, or teardrop-shaped, the electrode foot 1008 can have a maximum foot diameter measured along the thickest portion of the electrode foot 1008. In these instances, the maximum foot diameter can be greater than the leg diameter of each of the electrode legs 1006.

The electrode foot 1008 can be made in part or comprise a solid conductive material. For example, the electrode foot 1008 can be made of or comprise the same material as the electrode tip body 1000, the lateral struts 1002, the electrode arms 1004, and the electrode legs 1006. As shown in FIGS. 27A-27C, 28A-28B, 29, 30, 31, and 32A-32B, the electrode feet 1008 can be replaced by, coupled to, or coated/covered by a conductive cushioning material.

Figure 11B:
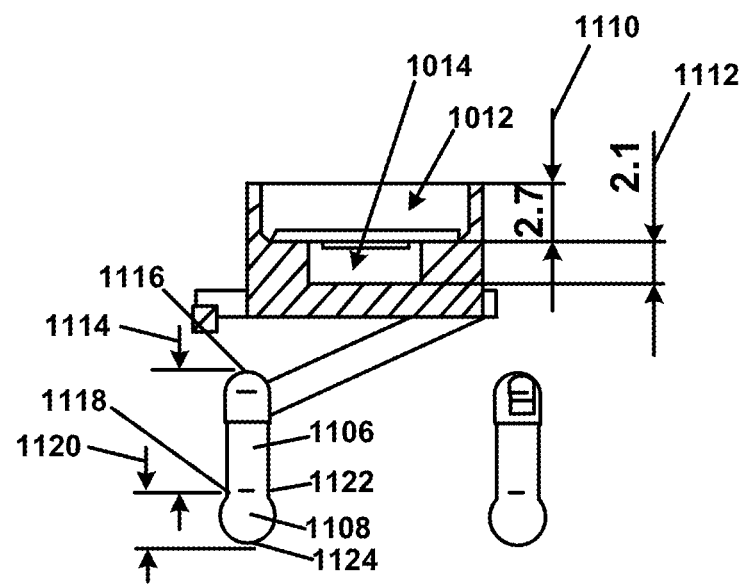
FIG. 11B is a cross-sectional view of the detachable electrode tip of FIG. 11A taking along cross-section G-G.

FIG. 11B illustrates that the first void portion 1012 can have a first void depth dimension 1110 and the second void portion 1014 can have a second void depth dimension 1112. The first void depth dimension 1110 can be between approximately 2.0 mm and 5.0 mm (e.g., about 2.7 mm). The second void depth dimension 1112 can be between approximately 1.5 mm and 5.0 mm (e.g., about 2.1 mm).

FIG. 11B also illustrates that each of the electrode legs 1006 can have a leg height 1114. The leg height 1114 can be measured from a leg proximal end 1116 to a leg distal end 1118. For example, the leg height 1114 can be between about 2.0 mm to about 20.0 mm. The leg height 1114 can also be between about 20.0 mm to about 30.0 mm.

Each of the electrode feet 1008 can have a foot height 1120. The foot height 1120 can be measured from a foot proximal end 1122 to a foot distal end 1124. The leg height 1114 can be greater than the foot height 1120. A ratio of the foot height 1120 to the leg height 1114 can be between about 1:1 to about 1:10 (e.g., about 1:3). For example, the leg height 1114 can be about 10.0 mm and the foot height 1120 can be about 3.0 mm.

FIG. 12A illustrates that the electrode leg 1006 can be radially aligned with a neighboring or flanking lateral strut 1002. Radial alignment can refer to the electrode leg 1006 being positioned radially outward from the neighboring or flanking lateral strut 1002 but substantially in line with the neighboring or flanking lateral strut 1002. FIG. 12A also illustrates that the electrode tip 144 can have an arm curvature length 1200. The arm curvature length 1200 can be a curved length of the electrode arm 1004 measured from the strut connecting end 1026 to the leg connecting end 1028.

FIG. 12B illustrates that the electrode leg 1006 can also be radially offset from a neighboring or flanking lateral strut 1002. The electrode leg 1006 can be radially offset from the neighboring or flanking lateral strut 1002 when the position of the electrode leg 1006 is not radially in line with the position of the neighboring or flanking lateral strut 1002. The arm curvature length 1200 of the electrode arm 1004 depicted in FIG. 12A can be greater than the arm curvature length 1200 of the electrode arm 1004 depicted in FIG. 12B.

FIGS. 12A and 12B illustrate that the electrode leg 1006 can have a substantially flat arm proximal end 1030 instead of a dome-shaped or rounded arm proximal end 1030. In addition, FIGS. 12A and 12B also illustrate that the foot distal end 1032 of the electrode leg 1006 can be uncoupled or unconnected to the electrode foot 1008 and the foot distal end 1032 of the electrode leg 1006 can directly contact the scalp or skin of the patient without an intervening electrode foot 1008.

FIGS. 12C and 12D illustrate that the electrode leg 1006 can be offset from the lateral strut 1002 by an offset distance 1202. In the variation of the electrode tip 144 shown in FIG. 12D, the offset distance 1202 can be greater than the offset distance 1202 shown in FIG. 12C. The offset distance 1202 between the electrode leg 1006 and the lateral strut 1002 can be increased by increasing the arm curvature length 1200, increasing the length of the latera strut 1002, decreasing the leg-foot height dimension 1104 (see FIG. 11A), or a combination thereof.

FIG. 13A illustrates that the electrode arm 1004 can be substantially planar and not curve or twist out of plane with the lateral strut 1002. For example, as shown in the side view of FIG. 13A, the entire electrode arm 1004 can curve along the same plane as the lateral strut 1002 such that the electrode arms 1004 form a spiral disk. In the variation of the electrode tip 144 shown in FIG. 13A, the electrode leg 1006 can be radially aligned with the neighboring or flanking lateral strut 1002.

FIG. 13B illustrates another variation of the electrode tip 144 where the electrode leg 1006 is radially offset from the neighboring or flanking lateral strut 1002 but the electrode arms 1004 are substantially planar or curve in plane along the entirety of the electrode arm or in plane with the lateral strut 1002.

FIGS. 14A and 14B illustrate variations of the electrode tip 144 with electrode arms 1004 that curve or rotate in a downward pitched or descending helical manner or trajectory. FIGS. 14A and 14B also illustrate that the arm height dimensions 1102 of the electrode arms 1004 can vary. For example, in the variation of the electrode tip 144 shown in FIG. 14B, the arm height dimension 1102 of the electrode arms 1004 can be greater than the arm height dimension 1102 of the electrode arms 1004 shown in FIG. 14A.

Figure 15:
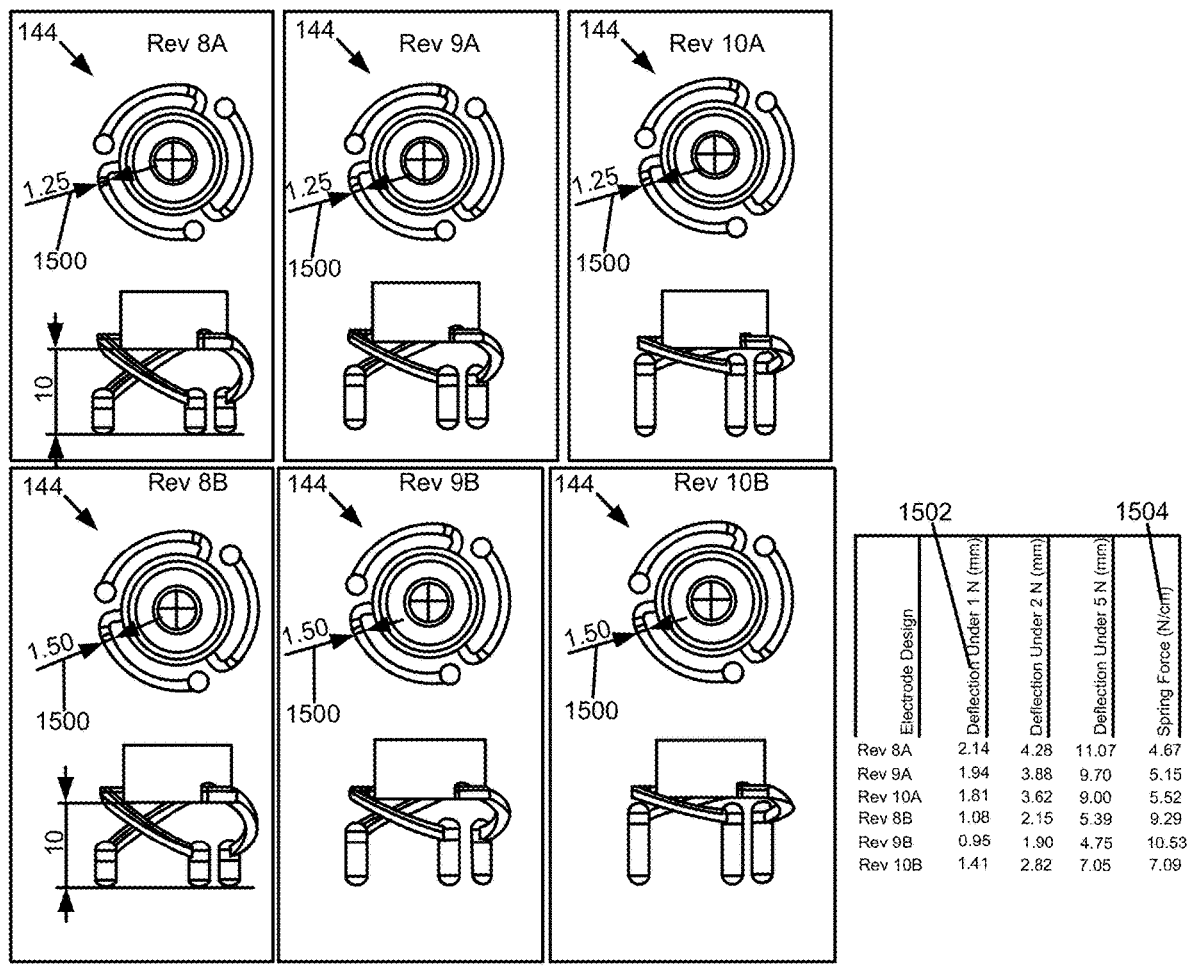
FIG. 15 illustrates top and side views of six separate variations of a detachable electrode tip having different electrode leg heights and electrode arm thicknesses.

FIG. 15 illustrates that varying a cross-sectional width 1500 of the electrode arms 1004 can affect the deflection distance 1502 exhibited by the electrode legs 1006 when the compressible and compliant electrode tip 144 is subjected to a compressive force.

The electrode tip 144 can exhibit a spring force of between about 4 N/cm to about 11 N/cm when the electrode tip 144 is subjected to one or more compressive forces. For example, the electrode tip 144 can exhibit a spring force of between about 4.67 N/cm to about 10.53 N/cm.

In addition, varying the cross-sectional width 1500 of the electrode arms 1004 can also affect a spring force 1504 exhibited by the entire electrode tip 144. Moreover, varying a combination of the leg-foot height dimension 1104 or the arm height dimension 1102 of the compressible and compliant electrode tip 144 can also affect the deflection distance 1502 exhibited by the electrode legs 1006 and the spring force 1504 exhibited by the entire electrode tip 144 when the electrode tip 144 is subjected to a compressive force.

For example, FIG. 15 illustrates six design variations of the compressible and compliant electrode tip 144. In the variations labeled Rev 8A, Rev 9A, and Rev 10A, the electrode arms 1004 have a cross-sectional width 1500 of approximately 1.25 mm. Moreover, the variation labeled Rev 8A has the shortest leg-foot height dimension 1104 (e.g., about 10.0 mm) but the longest arm height dimension 1102 and the variation labeled Rev 10A has the longest leg-foot height dimension 1104 but the shortest arm height dimension 1102.

As seen in FIG. 15, the electrode legs 1006 of Rev 8A can deflect: (1) a distance of 2.14 mm from an unbiased position when subjected to a compressive force of 1N; (2) a distance of 4.28 mm from an unbiased position when subjected to a compressive force of 2N; (3) a distance of 11.07 mm when subjected to a compressive force of 5N. In addition, the Rev 8A electrode tip 144 exhibits a spring force of 4.67 N/cm.

Furthermore, the electrode legs 1006 of Rev 9A can deflect: (1) a distance of 1.94 mm from an unbiased position when subjected to a compressive force of 1N; (2) a distance of 3.88 mm from an unbiased position when subjected to a compressive force of 2N; (3) a distance of 9.70 mm when subjected to a compressive force of 5N. In addition, the Rev 9A electrode tip 144 can exhibit a spring force of 5.15 N/cm.

Moreover, the electrode legs 1006 of Rev 10A can deflect: (1) a distance of 1.81 mm from an unbiased position when subjected to a compressive force of 1N; (2) a distance of 3.62 mm from an unbiased position when subjected to a compressive force of 2N; (3) a distance of 9.00 mm from an unbiased position when subjected to a compressive force of 5N. In addition, the Rev 9A electrode tip 144 can exhibit a spring force of 5.52 N/cm.

As shown by the aforementioned deflection and spring force values, the deflection distance 1502 can decrease as the leg-foot height dimension 1104 is increased and the spring force exhibited by the compressible and compliant electrode tip 144 can increase as the leg-foot height dimension 1104 is increased.

In the variations labeled Rev 8B, Rev 9B, and Rev 10B, the electrode arms 1004 have a cross-sectional width 1500 of approximately 1.50 mm (an increase of 0.25 mm from the cross-sectional widths shown in Rev 8A, Rev 9A, and Rev 10A). Moreover, the variation labeled Rev 8B has the shortest leg-foot height dimension 1104 (e.g., about 10.0 mm) but the longest arm height dimension 1102 and the variation labeled Rev 10B has the longest leg-foot height dimension 1104 but the shortest arm height dimension 1102.

As seen in FIG. 15, the electrode legs 1006 of Rev 8B deflect: (1) a distance of 1.08 mm when subjected to a compressive force of 1N; (2) a distance of 2.15 mm when subjected to a compressive force of 2N; (3) a distance of 5.39 mm when subjected to a compressive force of 5N. In addition, the Rev 8B electrode tip 144 exhibits a spring force of 9.29 N/cm.

Furthermore, the electrode legs 1006 of Rev 9B deflect: (1) a distance of 0.95 mm when subjected to a compressive force of 1N; (2) a distance of 1.90 mm when subjected to a compressive force of 2N; (3) a distance of 4.75 mm when subjected to a compressive force of 5N. In addition, the Rev 9B electrode tip 144 exhibits a spring force of 10.53 N/cm.

Moreover, the electrode legs 1006 of Rev 10B deflect: (1) a distance of 1.41 mm when subjected to a compressive force of 1N; (2) a distance of 2.82 mm when subjected to a compressive force of 2N; (3) a distance of 7.05 mm when subjected to a compressive force of 5N. In addition, the Rev 9B electrode tip 144 exhibits a spring force of 7.09 N/cm.

As shown by the aforementioned deflection and spring force values, the deflection distance 1502 decreases as the cross-sectional width 1500 of each of the electrode arms 1004 is increased. Moreover, the spring force 1504 exhibited by the entire electrode tip 144 increases as the cross-sectional width 1500 of each of the electrode arms 1004 is increased.

The force applied to the electrode tip 144 can be a result of the EEG headset 100 placement on a user's head. Adjustment of any of the band adjusters 131, 132, 133, 134, 135 and electrode adjusters 141 can vary the force applied to the electrode tip 144.

FIG. 16 illustrates that opposing compressive forces 2000*a* and 2000*b* can be applied to the body one or more of the electrode feet 1008 and electrode tip body 1000. The compressive forces 2000*a* and 2000*b* can be parallel to the cylindrical axis. When the electrode tip 144 is compressed, the electrode arms 1004 and electrode legs 1006 can deform, rotate, and translate from their unbiased positions to an angled orientation, as shown in FIG. 16 by the electrode arms 1004' and electrode legs 1006'.

Each electrode leg can have a leg longitudinal axis. The leg longitudinal axis can extend perpendicularly from the distal terminal end of the electrode arm 1004 when the electrode tip 144 is in an uncompressed, unbiased configuration. When the electrode tip 144 is in a compressed configuration, the electrode legs 1006' can resiliently deform into a biased configuration. The distance from the electrode foot 1008 when the electrode leg 1000 in the unbiased configuration to the electrode foot 1008' in when the electrode leg 1000' is in the biased configuration can be a leg foot shift distance. The leg foot shift distance can be from about 2 mm to about 5 mm, for example about 3.3 mm.

The angle from the leg longitudinal axis" when the electrode leg 1000 is in the unbiased configuration to the leg longitudinal axis'" when the electrode leg is in the biased configuration can be a leg foot shift angle. The leg foot shift angle can be from about 1 degree to about 90 degrees, more narrowly from about 10 degrees to about 45 degrees, for example about 20 degrees. When the electrode tip 144 is in an unbiased configuration, the leg longitudinal axis can be parallel with the cylindrical axis.

The height of the electrode tip 144 from the terminal end of the electrode tip body 1000 to the opposite terminal end of the electrode leg 1000 at the electrode foot 1008 can be an unbiased tip height when the electrode tip is in an unbiased tip configuration. The unbiased tip height can be from about 1 cm to about 10 cm, for example about 5 cm.

The height of the electrode tip 144 from the terminal end of the electrode tip body 1000 to the opposite terminal end of the electrode leg 1000' at the electrode foot 1008' can be a biased tip height when the electrode tip 144 is in a compressed configuration at maximum compression or during median expected use. The biased tip height can be from about 0.5 cm to about 5 cm, for example about 3 cm.

The difference between the biased tip height at maximum compression or during median expected use and the unbiased tip height can be from about 20% to about 80% of the unbiased tip height, for example about 50% of the unbiased tip height. The difference between the biased tip height and the unbiased tip height at maximum compression or during median expected use can be from about 0.5 cm to about 8 cm, more narrowly from about 1 cm to about 5 cm, for example about 2.5 cm or about 3 cm.

FIG. 17 illustrates that the headset 100 can have a chinstrap fixedly attached to a first side of the frame of the headset 100, for example at the right junction 112. The headset 100 can have a sidestrap attached to a second side of the frame of the headset 100, for example at the left junction 110, opposite the first side of the frame. The sidestrap can be slidably or fixedly attached to a first component of an adjuster buckle. The chinstrap can be slidably and adjustably attached to a second component of the adjuster buckle. The first and second components of the adjuster buckle can be detachably snap-connected to each other. The chinstrap can be slidably adjusted through the adjuster buckle, as shown by the chinstrap adjustment. The chinstrap can be slidably attached to a chinstrap pad. The chinstrap pad can be adjusted under the chin when the headset 100 is worn on a head and the adjuster buckle is fastened.

The chin can exert a chinstrap force against the chinstrap, for example through the chinstrap pad. The scalp can exert substantially oppositely directed forces relative to the chinstrap force. The forces exerted by the scalp can be the support block force against the support blocks and/or electrode tip forces against the electrode tips.

For example, support blocks, the spring elements 149, and electrode tips 144 can be compressed between (A) the effective chinstrap force, any force exerted by tightening the forces from adjusting the band adjusters, and weight of the frame of the headset 100 (which are effectively exerted against the top of the support blocks and electrodes) directed toward the scalp, and (B) the electrode tip forces and the support block forces exerted by the scalp against the bottom of the electrode tips and the support blocks.

Because scalps are often uneven and asymmetrical, some spring elements 149, and electrode tips 144 on opposite lateral positions of the scalp may be at different lengths of compression/expansion to accommodate for the topographical irregularities of the scalp. For example, the spring element 149, and electrode tip 144 at the C3 position may both be 50% compressed while the spring element 149, and electrode tip 144 at the C4 position may both be 25% compressed.

The spring element 149 and the electrode tip 144 for the same electrode can be at equal or unequal compression ratios. For example, the electrode tip 144 at the C4 position may be at 25% compression while the spring element 149 can concurrently be at 0% compression.

When the spring element 149 and/or the electrode tip 144 are sufficiently compressed, one or both of the support blocks adjacent to the given spring element 149 and/or electrode tip can contact the scalp, as shown in FIGS. 17 and 18.

The spring element travel length can be a total travel length of the spring element 149 from an unbiased configuration to maximum compression during use in the headset 100. The electrode tip travel length can be the unbiased tip height minus the biased tip height. The total travel length of the electrode can be the spring element travel length plus the electrode tip travel length. The total travel length as a ratio of the spring element travel length to the electrode tip travel length can be from about 0 (i.e., the spring element is not present or does not compress) to about 1 (i.e., the electrode tip is not compressible or is not present), more narrowly from about 0.25 to about 0.75, more narrowly from about 0.4 to about 0.6, for example about 0.5 or about 0.6.

The total travel length can be from about 1 cm to about 20 cm, more narrowly from about 3 cm to about 13 cm, yet more narrowly from about 5 cm to about 12 cm, for example about 10 cm or about 8 cm.

Figure 19:
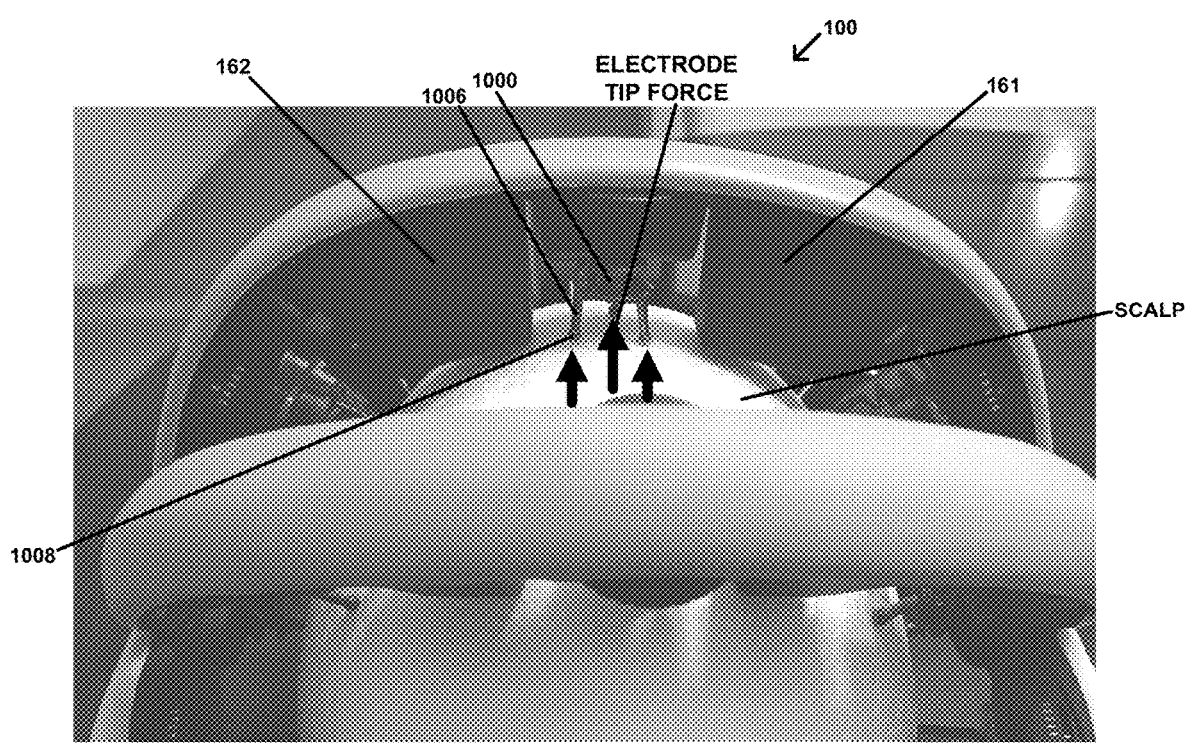
FIGS. 19 and 20 are black-and-white images showing a slight deflection of the electrode legs of an electrode tip coupled to a variation of a headset when the headset is worn by a model user and at least one of a side-strap and chinstrap is partially tightened.

FIG. 19 illustrates that the spring element 149 can be in a partially or completely compressed configuration while the electrode tip 144 is in an uncompressed/unbiased configuration. The support blocks may or may not (the latter as shown) contact the scalp.

Figure 20:
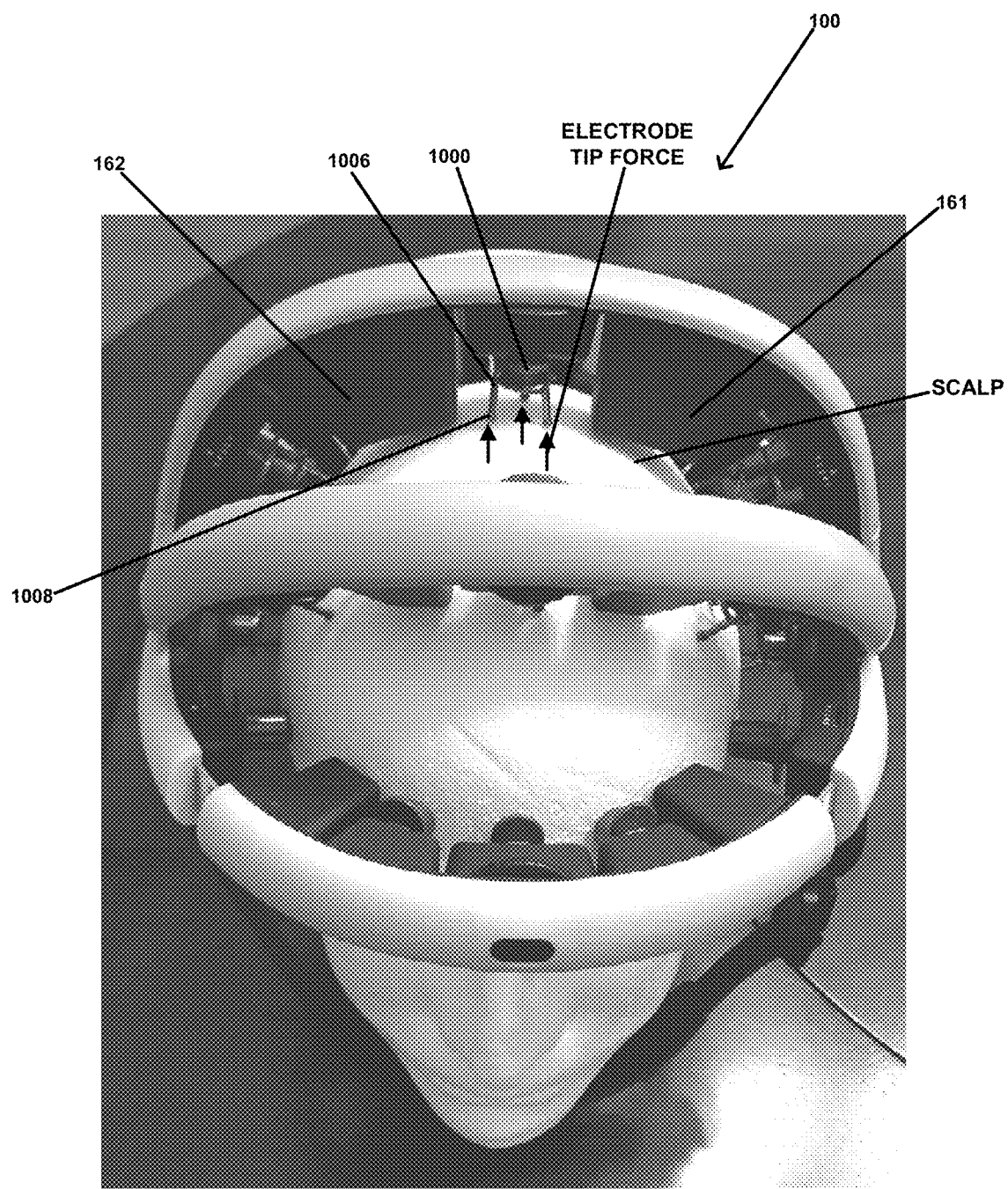
Figure 21:
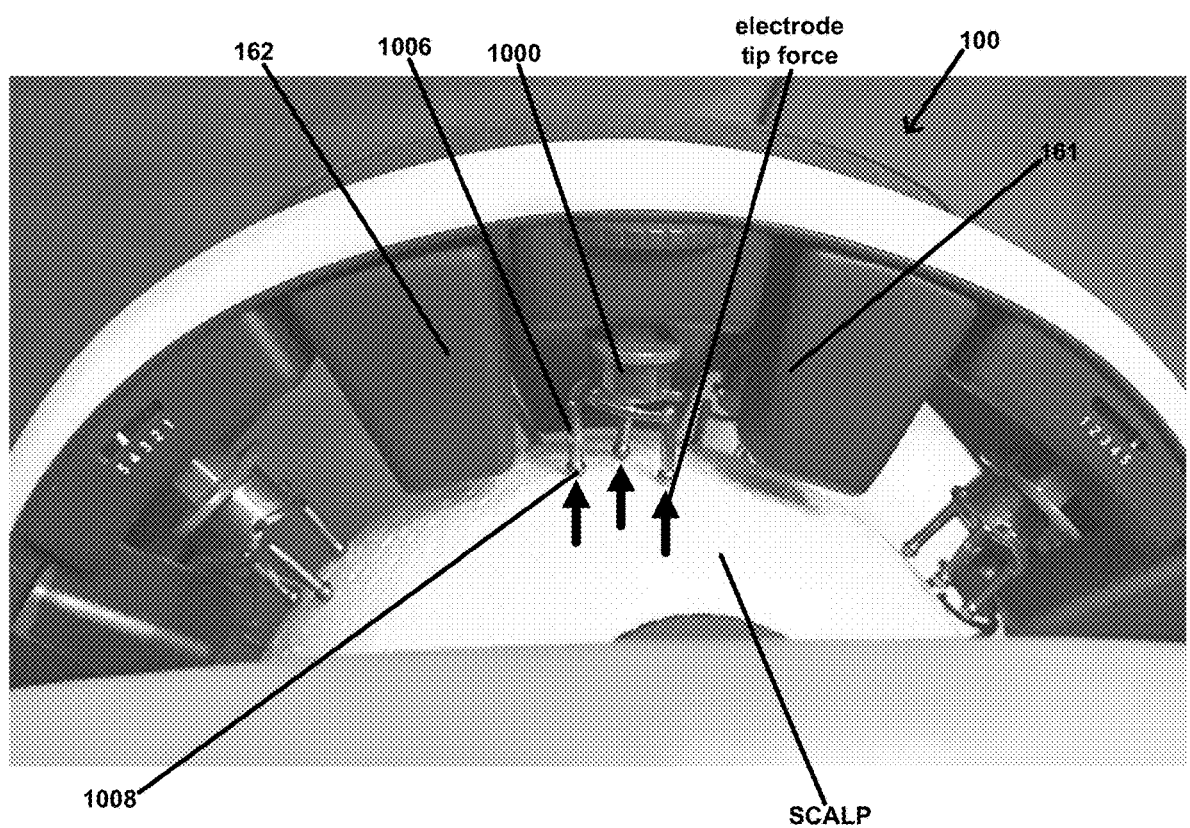
FIG. 21 is a black-and-white image showing electrode feet of electrode tips contacting a scalp of a model user prior to support blocks making contact with the scalp of the model user.

FIGS. 20 and 21 illustrate that the spring element 149 and the electrode tip 144 can be in uncompressed/unbiased configurations. The support blocks can be not contacting the scalp and spaced apart from the scalp by a gap.

When the spring element 149 and/or the electrode tip 144 are in unbiased/uncompressed configurations, such as in the configurations shown in FIGS. 19 through 21, the electrode tip can extend radially past the support blocks in the direction of the scalp. The electrode tip can be in contact with the scalp in the configuration as shown in FIGS. 17 through 23.

If the support blocks do not contact the scalp, such as shown in FIGS. 19 through 21, and the chinstrap force, weight of the frame, and the forces exerted by the band adjuster are equal between the configurations shown in FIGS. 17 and 18 as compared with FIGS. 19 through 21, then the force load that would have been exerted by the support block force can be added to the electrode tip forces otherwise exerted as shown in FIGS. 17 and 18. Accordingly, in this situation the pressure of the electrode feet 1008 on the scalp can be higher in the configurations shown in FIGS. 19 through 21 than the pressure of the electrode feet 1008 on the scalp in the configurations shown in FIGS. 17 and 18.

The electrode tip 144, for example, the spiral pitch height or electrode arm deflection 1018, can be changed by adjusting the tightness of the chinstrap, band adjuster 131, electrode adjuster 141, repositioning the frame of the headset 100 on the scalp, or combinations thereof.

Figure 22:
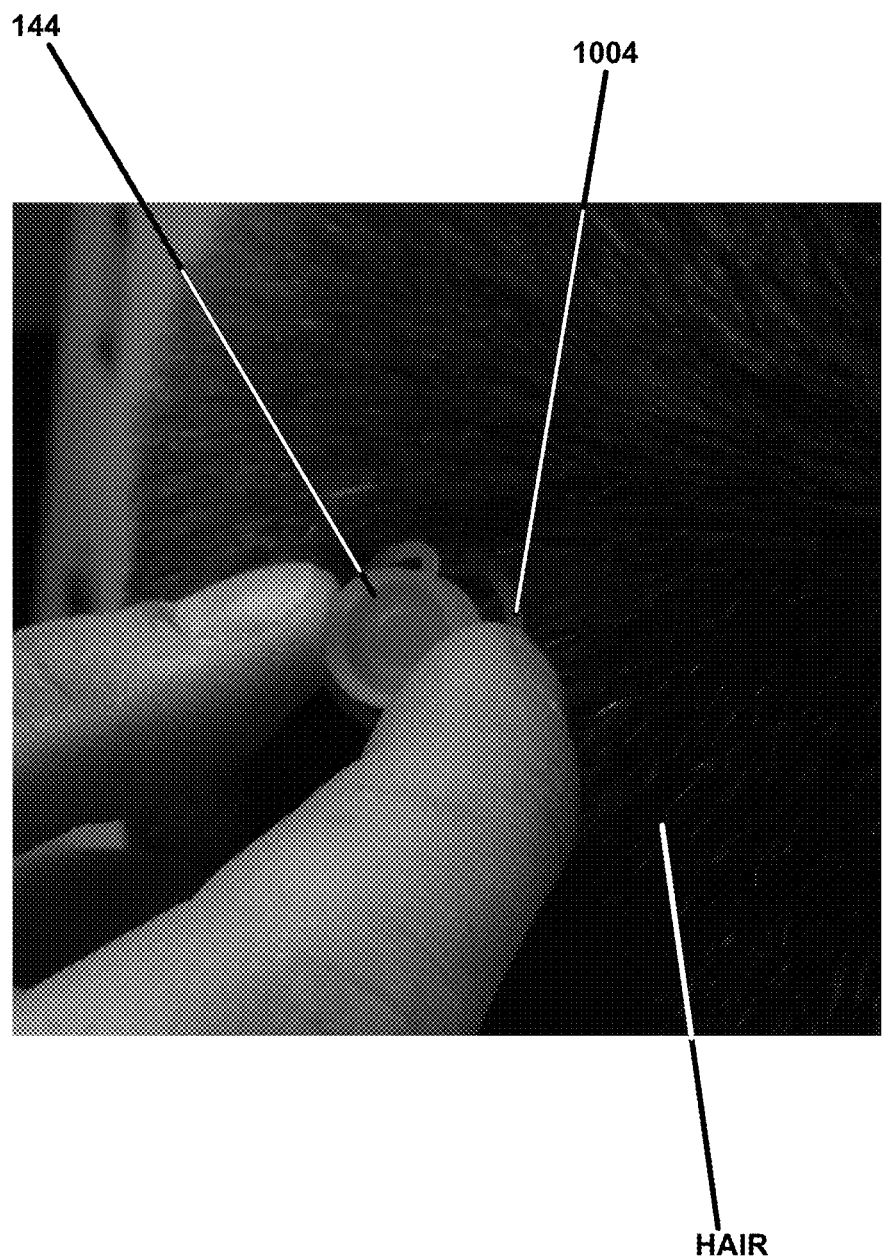
FIGS. 22 and 23 are black-and-white images showing a variation of a detachable electrode tip extending into the hair of a user.
Figure 23:
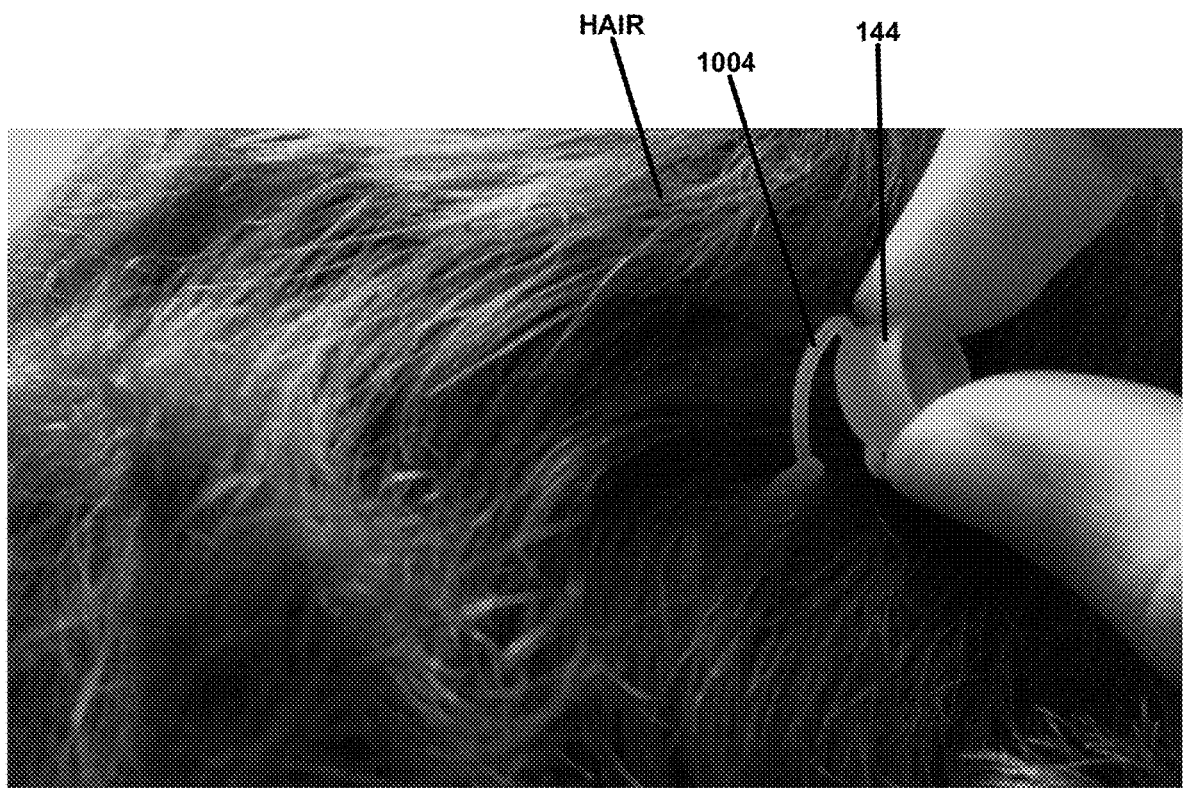

FIGS. 22 and 23 illustrate that the electrode tips 144 can be used on individuals with different lengths of hair. The electrode legs 1000 and electrode feet 1008 can push the hair out of the way and make contact with the user's scalp or skin during use. The deflection of the electrode tip 144 during compression can cause the electrode legs 1000 to translate and rotate, for example, pushing the hair strands aside of the electrode legs 1006 and pressing the electrode feet 1008 over the hair strands and into the scalp. The electrode feet 1008 can make an electrical connection with the user's head when in contact with the scalp.

Figure 24:
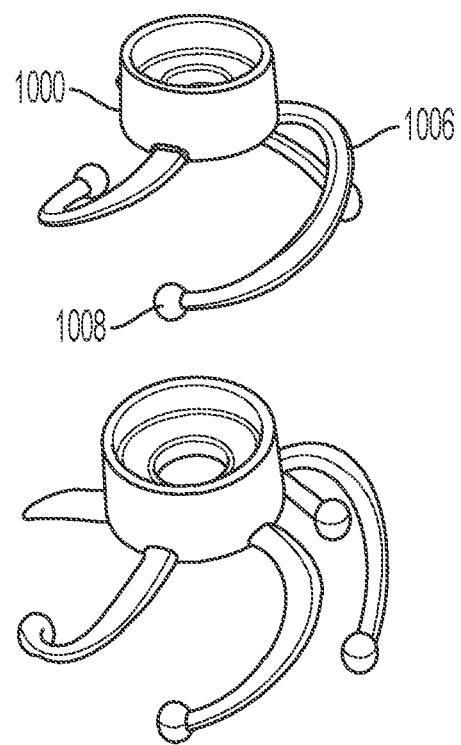
FIG. 24 illustrates two variations of a detachable electrode tip having three spiraled electrode arms extending from an electrode tip body and five spiraled electrode arms extending from an electrode tip body.
Figure 25:
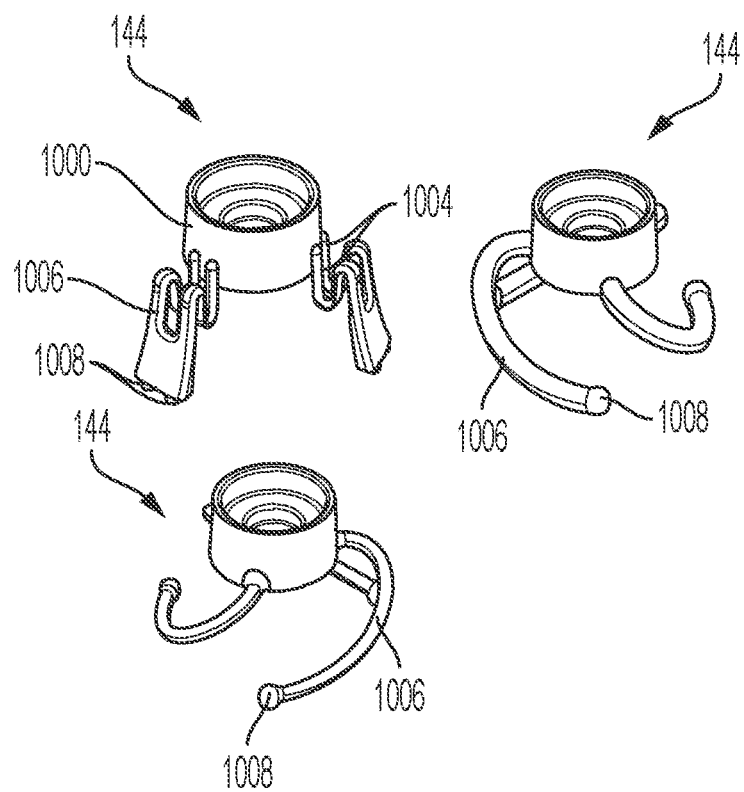
FIG. 25 illustrates three variations of a detachable electrode tip having multiple flipper-shaped electrode arms and legs, three spiraled electrode arms having a thick cross-sectional arm width, and three spiraled electrode arms having a thin cross-sectional arm width.
Figure 26:
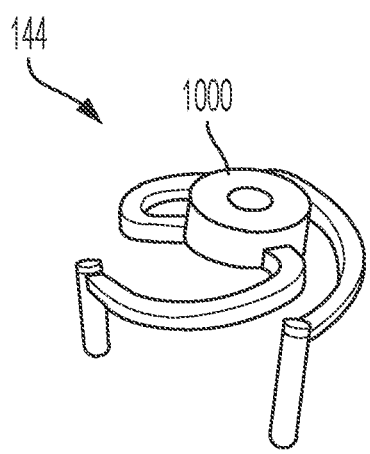
FIG. 26 is a black-and-white image showing a variation of a detachable electrode tip having an electrode tip body without a cup-shaped portion defined along a top of the electrode tip body.

FIGS. 24 through 26 illustrate variations of the electrode tip 144. FIG. 24 shows 3-arm (top) and 5-arm (bottom) versions of an electrode tip 144. The electrode tip 144 can have no lateral strut. The electrode leg 1006 can be coupled directly to the electrode tip body 1000. The electrode tips can be compliant or non-compliant. FIG. 25 shows that an electrode tip 144 can have two electrode arms 1004 and two electrode feet 1008 for each electrode leg 1006. Moreover, FIG. 25 shows that an electrode tip 144 can have electrode legs 1006 that can attach directly to the electrode tip body 1000.

FIG. 26 illustrates that the electrode tip body 1000 can be configured without the cup-shaped portion defining the void 1010. Even without the cup-shaped portion or void 1010, the electrode tip body 1000 can have a ferromagnetic component (e.g., the ferrous element 148) encased or embedded within the electrode tip body 1000 or at least part of the electrode tip body 1000 can be made of a ferromagnetic material.

Figure 27A:
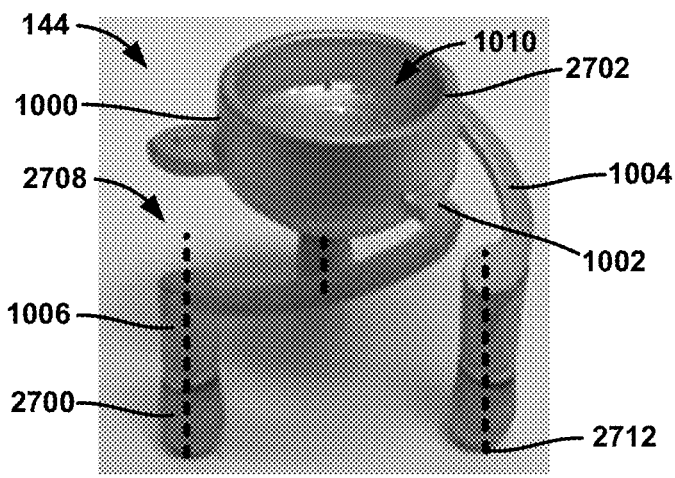
FIGS. 27A and 27B are black-and-white images showing perspective and top views, respectively, of a variation of a detachable electrode tip having a conductive cushioning material coating the electrode legs of the electrode tip.
Figure 27B:
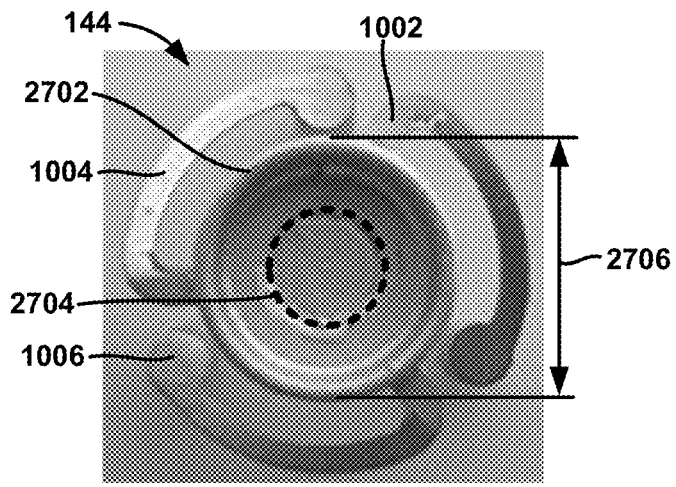

FIGS. 27A and 27B illustrate that a variation of a detachable electrode tip 144 can have a conductive cushioning material 2700 coating or covering each of the electrode legs 1006 of the electrode tip 144. The electrode tip 144 shown in FIGS. 27A and 27B (as well as FIGS. 27C, 28A-28B, 29, 30, 31A-32C, 32A-32C, 33, and 34) can be any of the electrode tips 144 disclosed herein, including the electrode tips 144 depicted in and described with respect to FIGS. 10A-10D, 11A-11B, 12A-12D, 13A-13B, 14A-14B, 15, 16, 17, 18, 19, 20, 21, 22, 23, 24, 25, and 26). Moreover, the conductive cushioning material 2700 can also coat, cover, or be coupled to any of the electrode legs of electrode tips 144 depicted in and described with respect to FIGS. 1, 2, 3, 4, 5, 6, 7, 8, and 9.

As shown in FIGS. 27A and 27B, the electrode tip 144 can comprise an electrode tip body 1000, one or more deflectable electrode legs 1006 coupled to or extending from the electrode tip body 1000, and a conductive cushioning material 2700 coupled to, coated onto, or covering at least a segment of each of the electrode legs 1006. The conductive cushioning material 2700 can be infused or saturated with or retain one or more conductors (e.g., ionic species or compounds, etc.). The material composition of the conductive cushioning material 2700 will be discussed in more detail in the following sections.

FIGS. 27A and 27B also illustrate that the electrode legs 1006 can be coupled to the electrode tip body 100 via one or more lateral struts 1002 and one or more electrode arms 1004. The lateral struts 1002 can extend radially from the electrode tip body 1000. The lateral struts 1002 can be coupled to the electrode tip body 1000 at positions arranged uniformly or equidistantly around a circumference of the electrode tip body 1000.

The one or more electrode arms 1004 can curve along a spiral trajectory or pattern around a circumference of the electrode tip body 1000. For example, the one or more electrode arms 1004 can curve in a clockwise or left-handed rotational direction, a counterclockwise or right-handed rotational direction, or a combination thereof. Each of the electrode arms 1004 can comprise a proximal arm end (in proximity to the electrode tip body 1000) and a distal arm end (in proximity to the electrode legs 1006), the electrode arms 1004 can curve along a downward pitched or descending helical trajectory such that the distal arm end is vertically lower or below the proximal arm end.

The electrode tip body 1000, the one or more lateral struts 1002, the one or more electrode arms 1004, and the one or more electrode legs 1006 can be made in part or comprise a conductive material. The electrode tip body 1000, the one or more lateral struts 1002, the one or more electrode arms 1004, and the one or more electrode legs 1006 can be made in part or comprise a conductive polymeric material, a conductive metallic material, or a composite thereof. The electrode tip body 1000, the one or more lateral struts 1002, the one or more electrode arms 1004, and the one or more electrode legs 1006 of the electrode tips 144 depicted in and described with respect to FIGS. 27A-27C, 28A-28B, 29, 30, 31A-32C, 32A-32C, 33, and 34 can be made of or comprise the same materials as the electrode tips 144 depicted in and described with respect to FIGS. 10A-10D, 11A-11B, 12A-12D, 13A-13B, 14A-14B, 15, 16, 17, 18, 19, 20, 21, 22, 23, 24, 25, and 26. Since the electrode legs 1006 can also be coated or covered by a conductive cushioning material *, the entire electrode tip 144 can be coupled to an active electrode (e.g., the first electrode 140, the second electrode 152, and the third electrode 153, etc.) of the headset 100 to sense a bioelectrical potential of a user wearing the headset 100.

FIGS. 27A and 27B also illustrate that the electrode tip body 1000 can have a cup-shaped portion 2702 surrounding a hollow center, divot, or void 1010. The cup-shaped portion 2702 can be defined along a top or proximal portion of the electrode tip body 1000. The void 1010 or divot can be substantially cylindrical-shaped, dome-shaped or shaped as a hemisphere, cuboidal-shaped, ovoid-shaped, ellipsoid-shaped, pyramidal-shaped, rhomboid-shaped, or a combination thereof. The void 1010 can extend partially into a top or proximal portion of the electrode tip body 1000. The void 1010 can comprise a first void portion and a smaller second void portion set within the first void portion. For example, the first void portion can have a first void diameter and the second void portion can have a second void diameter shorter in length than the first void diameter. The first void portion can be substantially concentric with the second void portion. The second void portion 1014 can extend further into the electrode tip body 1000 than the first void portion.

As previously discussed, the electrode body 142 can comprise a first ferromagnetic component or a magnetic element 143 (see FIG. 8). The first ferromagnetic component can be positioned at a distal or terminal end of the electrode body 142. For example, the first ferromagnetic component can be positioned distal or beyond the shoulder 145 of the electrode. The first ferromagnetic component (e.g., the magnetic element 143) can be partially encased or surrounded by part of the electrode body 142. The first ferromagnetic component can be coupled to the electrode body 142 by adhesives (e.g., conductive adhesives), an interference fit, latches, clips, or a combination thereof.

The electrode tip 144 can comprise a second ferromagnetic component 2704 (represented using the circle in broken lines in FIG. 27B). The second ferromagnetic component 2704 can be complementary to the first ferromagnetic component such that the first ferromagnetic component can magnetically couple to the second ferromagnetic component 2704 when the first ferromagnetic component is positioned or placed in proximity to the second ferromagnetic component 2704. The second ferromagnetic component 2704 can also refer to or be the same as the ferrous element 148 (see FIG. 8).

As shown in FIG. 27B, the second ferromagnetic component 2704 can be encased within a portion of the electrode tip body 1000. The second ferromagnetic component 2704 can be positioned or secured within part of the void 1010 such as within the second void portion and covered or sealed by additional material used to make the remainder of the electrode tip body 1000. For example, the second ferromagnetic component 2704 can be embedded or encased within the electrode tip body 1000 immediately below (i.e., vertically inferior to) the bottom of the void 1010. In other variations, the second ferromagnetic component 2704 can be visible and extend out from the void 1010, fill at least part of the void 1010, be coupled to the bottom of the cup-shaped portion 2702, or a combination thereof.

The electrode tip 144 can detachably or removably couple to the electrode body 142 when the cup-shaped portion 2702 of the electrode tip body 1000 is pushed onto or otherwise biased toward the first ferromagnetic component. The void 1010 or hollow center defined by the cup-shaped portion 2702 can be configured to surround or cup over at least part of the first ferromagnetic component. By doing so, the second ferromagnetic component 2704 can be biased or brought closer to the first ferromagnetic component and the electrode tip 144 can be magnetically coupled to the electrode body 142.

The first ferromagnetic component can comprise or be made in part of a permanent magnet, an electropermanent magnet, a ferromagnetic metal or ferrous metal, or a combination thereof. The second ferromagnetic component 2704 can comprise or be made in part of a permanent magnet, an electropermanent magnet, a ferromagnetic metal or ferrous metal, or a combination thereof. For example, the first ferromagnetic component (e.g., the magnetic element 143) can be a permanent magnet and the second ferromagnetic component 2704 can be a ferromagnetic or ferrous metal configured to magnetically couple to the permanent magnet. Alternatively, the first ferromagnetic component can be a ferromagnetic or ferrous metal and the second ferromagnetic component 2704 can be a permanent magnet configured to magnetically couple to the ferromagnetic or ferrous metal. At least part of the electrode tip body 1000 can also be made of a ferromagnetic material.

The second ferromagnetic component 2704 can be sized to fit within the void 1010 defined by the cup-shaped portion 2702. For example, the second ferromagnetic component 2704 can have a component diameter or width and the component diameter or width can be smaller than a tip body diameter 2706 of the electrode tip body 1000.

Figure 27C:
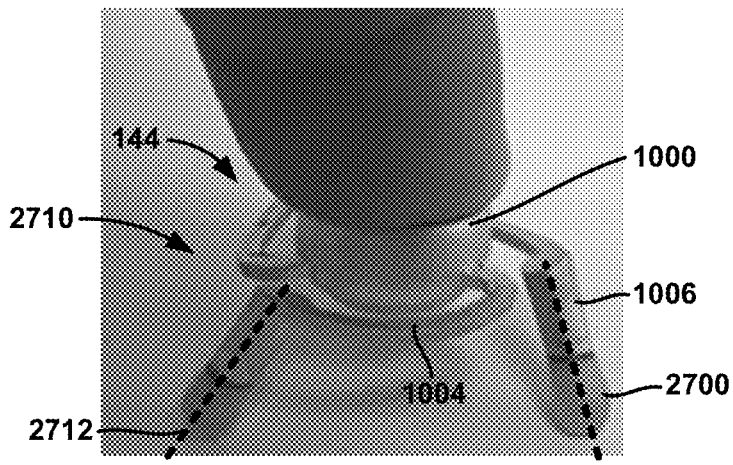
FIG. 27C is a black-and-white image showing a perspective view of a compressive force being applied to the detachable electrode tip shown in FIGS. 27A and 27B.

FIG. 27C illustrates that a compressive force can be applied to the detachable electrode tip 144 shown in FIGS. 27A and 27B and the electrode legs 1006 of the electrode tip 144 can deflect or spread-out in response to the compressive force.

The electrode legs 1006 can have a non-biased configuration 2708 (as shown in FIG. 27A) and a splayed configuration 2710 (as shown in FIG. 27C). For example, each of the electrode legs 1006 can have leg longitudinal axis 2712.

The leg longitudinal axis 2712 of each of the electrode legs 1006 can be oriented substantially parallel to one another when the electrode legs 1006 are in the non-biased configuration 2708 (as shown in FIG. 27A). However, the leg longitudinal axis 2712 of each of the electrode legs 1006 can be oriented substantially non-parallel to one another when the electrode legs 1006 are biased into the splayed configuration 2710. Moreover, as shown in FIG. 27C, one or more of the electrode arms 1004 can bend or flex when compressive forces are applied to the electrode tip 144.

When the electrode tip 144 is coupled to the electrode body 142 of the electrode connected to the headset 100, the electrode legs 1006 of the electrode tip 144 can be biased into the splayed configuration 2710 when one or more straps (e.g., the side straps or chin strap, shown in FIG. 17) of the headset 100 are tightened or when one of the bands of the headset 100 is adjusted such that the headset 100 fits on a head or scalp of the user. The design of the compressible electrode tips 144 (including the deflectable electrode legs 1006 and the bendable electrode arms 1004) can increase the comfort of the headset 100 when the headset 100 is worn by a user and can allow the headset 100 to accommodate different head topographies of different users. The signal quality of the bioelectrical signals obtained by the headset 100 can remain the same or even improve when the electrode tips 144 are compressed and the electrode legs 1006 are in the splayed configuration 2710. For example, a clinician or operator of the headset 100 can confirm that headset 100 is properly placed on a head of a user when the clinician or operator sees that the electrode tips 144 are compressed and the electrode legs 1006 of such electrode tips 144 are in the splayed configuration 2710. Electrode legs 1006 in the splayed configuration 2710 can also facilitate proper or adequate clearing or displacement of hair such that the conductive cushioning material 2700, the electrode feet 1008 (see FIGS. 10A-10D and 11A-11B), or a combination thereof makes physical contact with the scalp of the user.

Figure 28A:
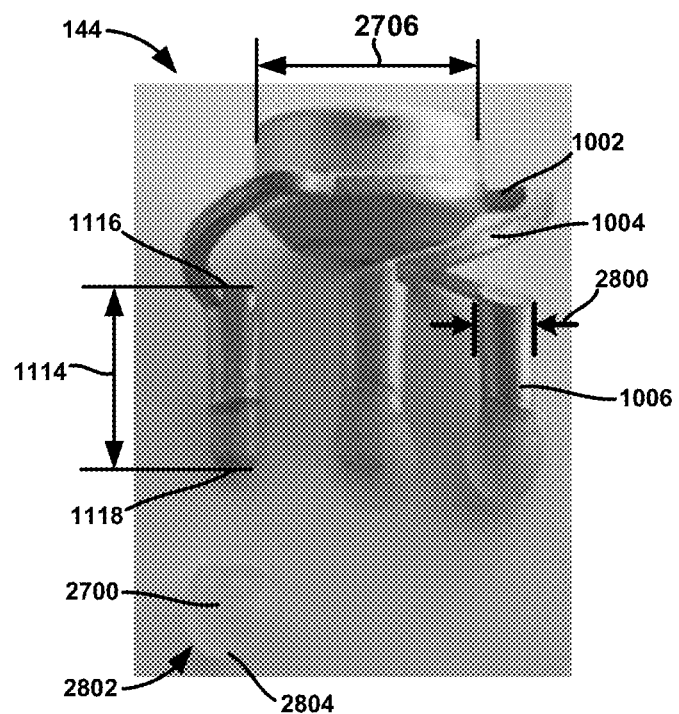
FIGS. 28A and 28B are black-and-white images showing side and bottom views, respectively, of a variation of a detachable electrode tip having a conductive cushioning material coating two electrode legs of the electrode tip and the conductive cushioning material removed from one of the electrode legs.

FIG. 28A illustrates that each of the electrode legs 1006 can have a leg height 1114 as measured from a leg proximal end 1116 to a leg distal end 1118. Moreover, each of the electrode legs 1006 can have a leg diameter 2800 (when the electrode legs 1006 are substantially shaped as elongate rods) or a maximum leg width (when the electrode legs 1006 are substantially shaped as elongate cuboids or other elongate three-dimensional polygonal shapes).

FIG. 28A also illustrates that the conductive cushioning material 2700 can be ovoid-shaped 2802 having a rounded bottom or terminal surface 2804. The conductive cushioning material 2700 can also be ovoid-shaped, ellipsoid-shaped, teardrop-shaped, or a combination thereof. Alternatively, the conductive cushioning material 2700 can also be substantially spherical-shaped. The shape of the conductive cushioning material 2700 can contribute to the comfort level of the user when the user wears the headset 100 having the electrode tips 144 coupled to the electrodes connected to the headset 100. The shape of the conductive cushioning material 2700 can also play a role in enhancing the signal quality of the bioelectrical signals measured by the headset 100.

Figure 28B:
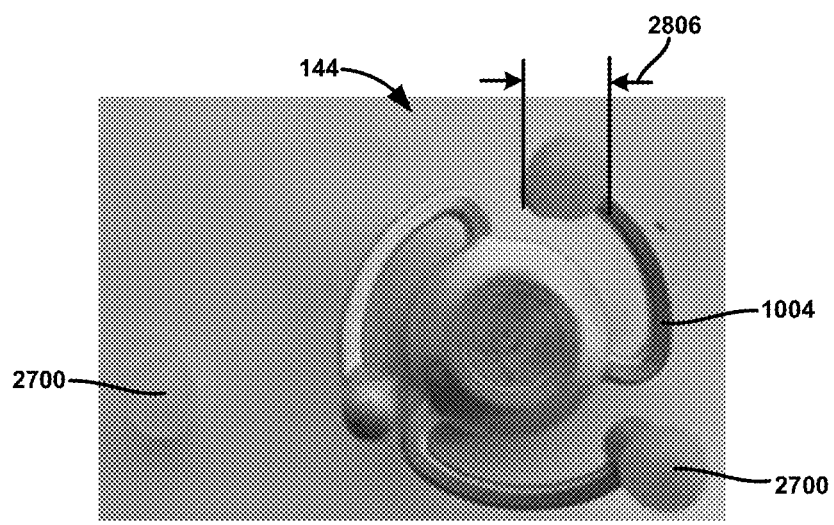

FIG. 28B illustrates that the conductive cushioning material 2700 can also have a maximum cushion diameter 2806. The maximum cushion diameter 2806 can be the diameter or horizontal width of the conductive cushioning material 2700 as measured along the thickest or widest part of the conductive cushioning material 2700. The maximum cushion diameter 2806 can be greater than the leg diameter 2800 of the electrode legs 1006. This design can increase the stability of the electrode tips 144 and increase the comfort level of a user wearing the headset 100.

FIGS. 28A and 2B also illustrate that the tip body diameter 2706 of the electrode tip body 1000 can be greater than the leg diameter 2800 and the maximum cushion diameter 2806. For example, the ratio of the leg diameter 2800 to the tip body diameter 2706 can be between about 1:2 and 1:10. More specifically, the ratio of the leg diameter 2800 to the tip body diameter 2706 can be about 1:3.

Figure 29:
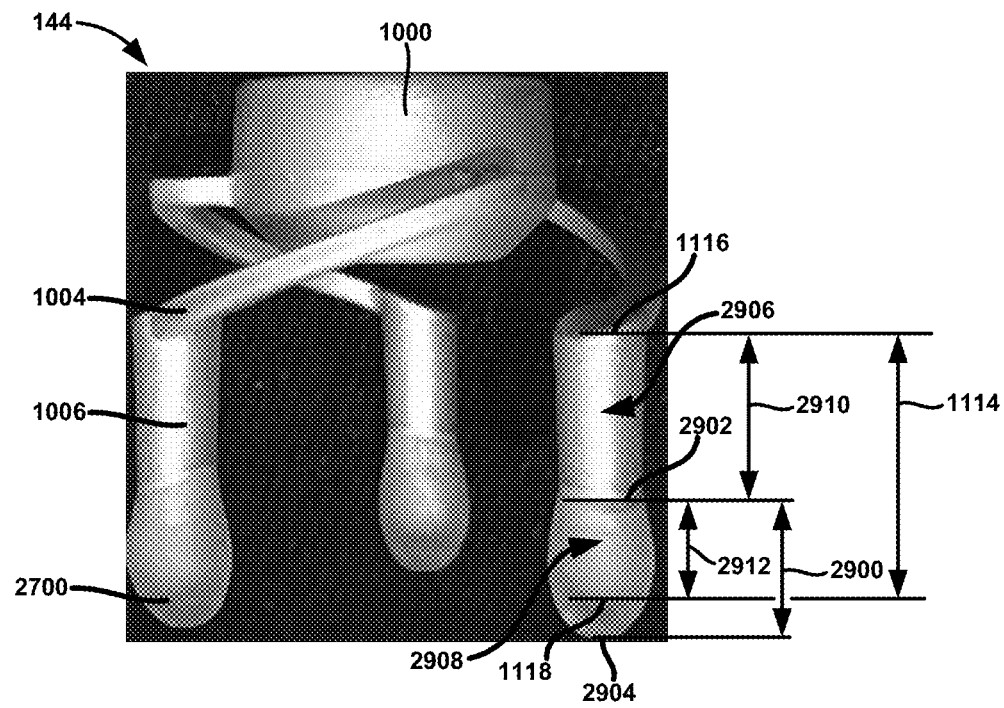
FIG. 29 is a black-and-white image showing a close-up view of a variation of a detachable electrode tip having a conductive cushioning material coating the electrode legs of the electrode tip.

FIG. 29 illustrates that the conductive cushioning material 2700 coating the electrode legs 1006 of the electrode tip 144 can extend vertically beyond the leg distal ends 1118 of the electrode legs 1006.

As previously discussed, each of the electrode legs 1006 can have a leg height 1114 as measured from a leg proximal end 1116 to a leg distal end 1118. For example, the leg height 1114 can be between about 2.0 mm to about 20.0 mm (e.g., 10.0 mm). The leg height 1114 can also be between about 20.0 mm to about 30.0 mm, or longer than 30.0 mm.

The conductive cushioning material 2700 can also have a cushion height 2900. The cushion height 2900 can be measured from a cushion proximal end 2902 of the conductive cushioning material 2900 to a cushion distal end 2904. The cushion distal end 2904 of the conductive cushioning material 2700 can extend vertically beyond (e.g., inferior to) to the leg distal end 1118 of the electrode leg 1006.

The cushion height 2900 can be less than the leg height 1114 of the electrode leg 1006 covered by the conductive cushioning material 2700. For example, the cushion height 2900 can be between about 2.0 mm to about 10.0 mm (e.g., 5.0 mm). The cushion height 2900 can also be between about 10.0 mm and 20.0 mm, or greater than 20.0 mm.

A ratio of the cushion height 2900 to leg height 1114 of the electrode leg 1006 covered by the conductive cushioning material 2700 can be between about 1:2 to 1:3. Moreover, the ratio of the cushion height 2900 to leg height 1114 of the electrode leg 1006 covered by the conductive cushioning material 2700 can be between about 1:3 to 1:5 (e.g., about 1:4).

Figure 32A:
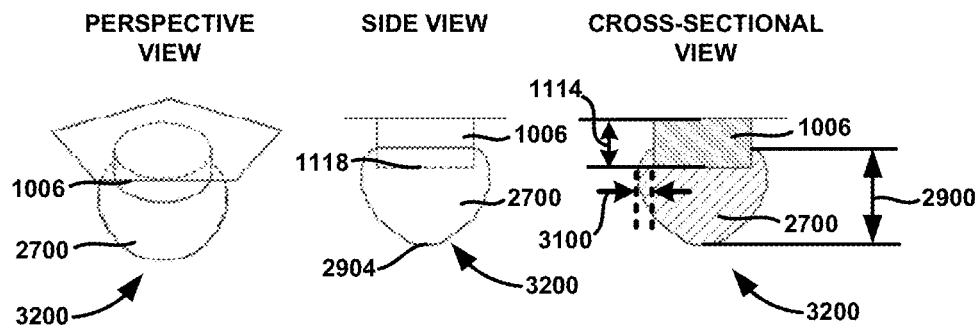
FIGS. 32A-32C illustrate perspective, side, and cross-sectional views of different variations of electrode legs coated by a conductive cushioning material.
Figure 32B:
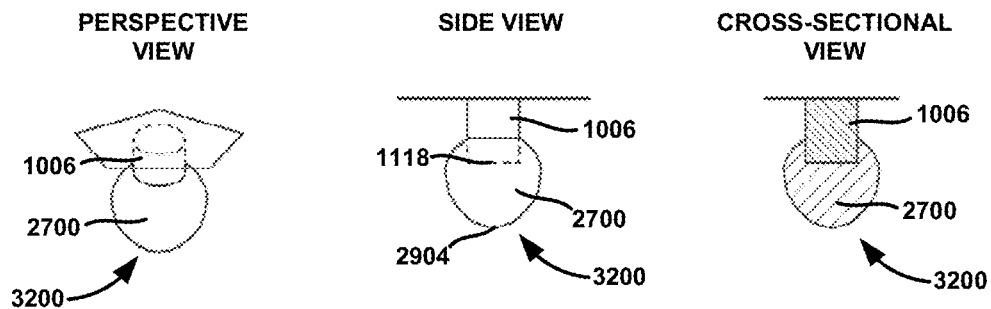

Alternatively, the cushion height 2900 can be greater than or equal to the leg height 1114 of the electrode leg 1006 covered by the conductive cushioning material 2700 (as shown in FIGS. 32A and 32B). For example, the ratio of the cushion height 2900 to leg height 1114 of the electrode leg 1006 covered by the conductive cushioning material 2700 can be between about 3:1 to 1:1 (e.g., 2:1).

When the leg distal end 1118 of the electrode leg 1006 is coated or covered by the conductive cushioning material 2700, the electrode leg 1006 can have a leg uncovered portion 2906 and a leg covered portion 2908. The leg uncovered portion 2906 can have an uncovered portion height 2910 and the leg covered portion 2908 can have a covered portion height 2912.

As shown in FIG. 29, the uncovered portion height 2910 can be greater than the covered portion height 2912. For example, the uncovered portion height 2910 can be between about 5.0 mm and 10.0 mm (e.g., 7.0 mm). The uncovered portion height 2910 can also be between about 10.0 mm and 20.0 mm, or greater than 20.0 mm. The covered portion height 2912 can between about 2.0 mm and 5.0 mm (e.g., 3.0 mm). The covered portion height 2912 can also be between about 5.0 mm and 10.0 mm, or greater than 10.0 mm. A ratio of the covered portion height 2912 to the uncovered portion height 2910 can be between about 1:2 to about 1:5.

In some instances, the covered portion height 2912 can be greater than the uncovered portion height 2910. For example, the covered portion height 2912 can be between about 5.0 mm and 10.0 mm (e.g., 7.0 mm). The covered portion height 2912 can also be between about 10.0 mm and 20.0 mm, or greater than 20.0 mm. The uncovered portion height 2910 can between about 2.0 mm and 5.0 mm (e.g., 3.0 mm). The uncovered portion height 2910 can also be between about 5.0 mm and 10.0 mm, or greater than 10.0 mm. A ratio of the uncovered portion height 2910 to the covered portion height 2912 can be between about 1:2 to about 1:5.

Figure 30:
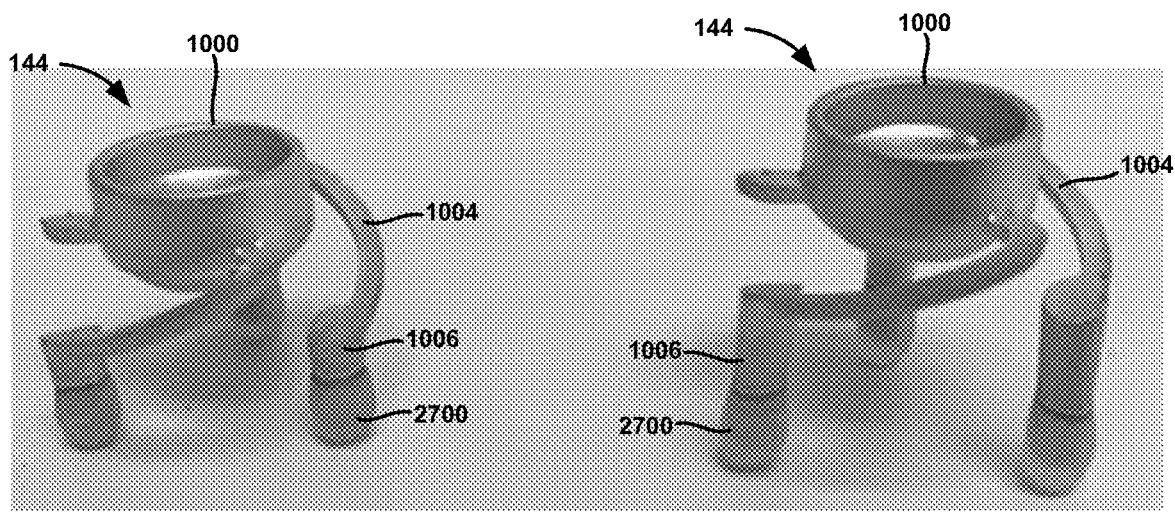
FIG. 30 is a black-and-white image showing two variations of a detachable electrode tip having different electrode leg heights and a conductive cushioning material coating the electrode legs.

FIG. 30 illustrates that the detachable electrode tips 144 can have different electrode leg heights 1114. This can allow a clinician or operator to select a size of the electrode tip 144 that is most appropriate for a user's head shape or head size.

Figure 31A:
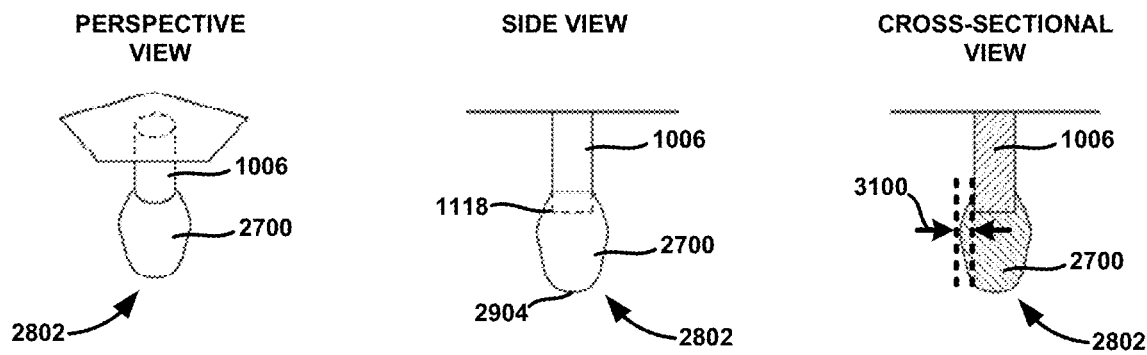
FIGS. 31A-31C illustrate perspective, side, and cross-sectional views of different variations of electrode legs coated by a conductive cushioning material.
Figure 31B:
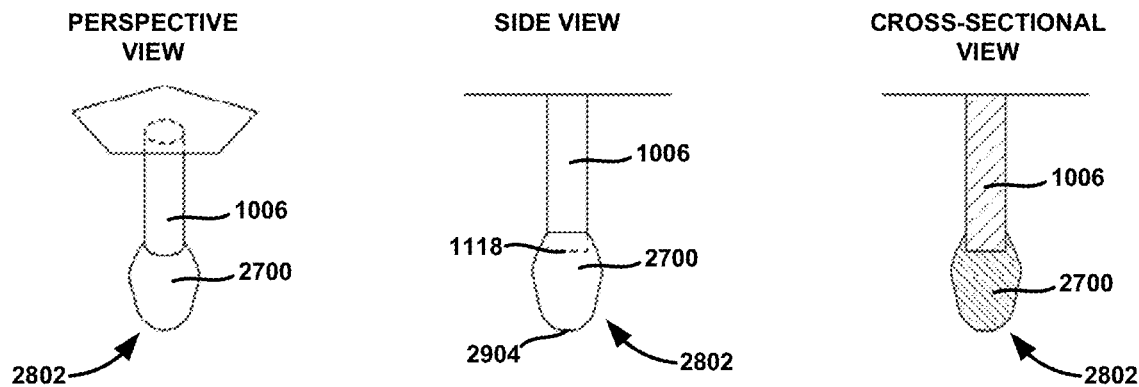
Figure 31C:
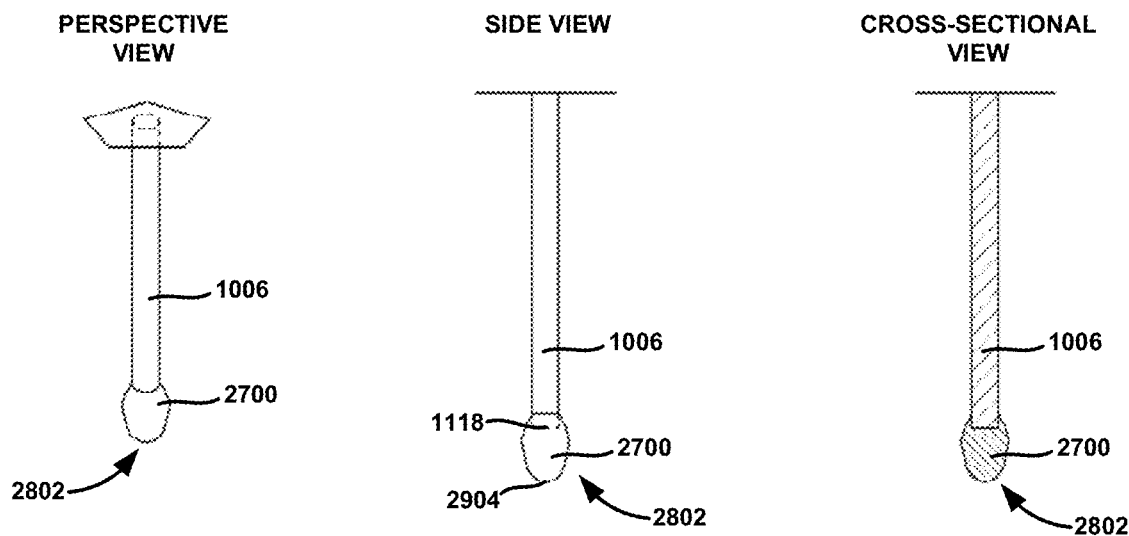

FIGS. 31A-31C illustrate that electrode legs 1006 of differing heights or lengths can be coated by the conductive cushioning material 2700. As shown in FIGS. 31A-31C, the conductive cushioning material 2700 can be substantially ovoid-shaped 2802, ellipsoid-shaped, or a combination thereof. The conductive cushioning material 2700 can also be teardrop-shaped, frusto-conic shaped, cuboid-shaped, cylindrical, or a combination thereof.

FIGS. 31A-31C also illustrate that the cushion distal end 2904 of the conductive cushioning material 2700 can extend beyond (vertically past) the leg distal end 1118. Although FIGS. 31A-31C show the conductive cushioning material 2700 covering or coating a distal segment of the electrode leg 1006, it is contemplated by this disclosure that the conductive cushioning material 2700 can cover or coat a segment of the electrode leg 1006 starting from a leg midpoint to the leg distal end 1118. Alternatively, the conductive cushioning material 2700 can cover or coat a segment of the electrode leg 1006 starting from a point in between the leg proximal end 1116 and the leg midpoint to the leg distal end 1118.

FIGS. 31A-31C also illustrate that the conductive cushioning material 2700 can have a maximum cushion thickness 3100. The maximum cushion thickness 3100 can be measured from a lateral surface of the electrode leg 1006 to an exterior surface of the conductive cushioning material 2700 along the widest or thickest portion of the conductive cushioning material 2700. The maxim cushion thickness 3100 can be between about 0.05 mm to about 10.0 mm. The maximum cushion thickness 3100 can also be between 10.0 mm and 20.0 mm. More specifically, the maxim cushion thickness 3100 can be between about 0.05 mm to about 2.50 mm. Even more specifically, the maxim cushion thickness 3100 can be between about 1.25 mm to about 2.00 mm (e.g., 1.50 mm).

Figure 32C:
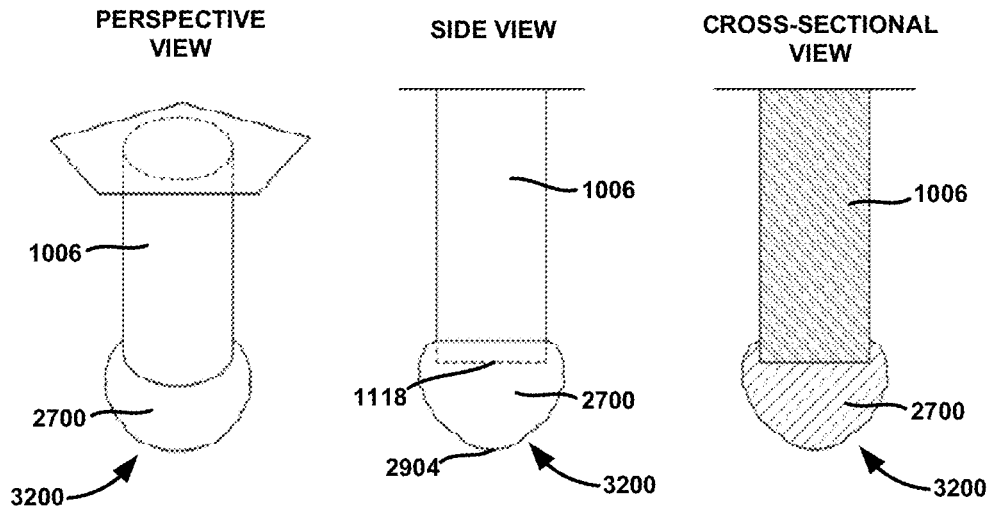

FIGS. 32A-32C also illustrate that electrode legs 1006 of differing heights or lengths can be coated by the conductive cushioning material 2700. FIGS. 32A-32C also illustrate that the conductive cushioning material 2700 can be substantially bulbous-shaped 3200 or globular. The conductive cushioning material 2700 can also be substantially spherical-shaped, dome-shaped, disk-shaped, or a combination thereof.

FIG. 32A illustrates that, in some instances, the cushion height 2900 of the conductive cushioning material 2700 can be greater than the leg height 1114 of the electrode leg 1006 covered or coated by the conductive cushioning material 2700. Alternatively, the leg height 1114 of the electrode leg 1006 covered or coated by the conductive cushioning material 2700 can be equal to or greater than the cushion height 2900 of the conductive cushioning material 2700.

The conductive cushioning material 2700 can be infused or saturated with or retain one or more conductors. The conductors can comprise conductive ions (e.g., ionic compounds or species), carbon, nanoparticles, or a combination thereof.

The conductive cushioning material 2700 can be a cured and/or plasticized polymeric material. For example, the conductive cushioning material 2700 can be a hydrogel. The hydrogel can be coated onto a segment of the electrode leg(s) 1006. More specifically, the conductive cushioning material 2700 can be crystallized and/or plasticized hydrogel. The hydrogel can be cured by ultraviolet (UV) radiation. The hydrogel can also be cured by thermal radiation (i.e., at elevated temperatures). In some instances, the hydrogel can be a crystallized hydrogel.

The hydrogel can be air dried at ambient temperatures (e.g., between about 33° Celsius to about 37° Celsius) The hydrogel can be coated onto the segment of at least one of the electrode legs 1006 by dip-coating. The electrode leg(s) 1006 can be dip-coated repeatedly or subjected to multiple dip-coating procedures. When the electrode tip 144 comprises multiple electrode legs 1006 all such electrode legs 1006 can be dip-coated all at once or each electrode leg 1006 can be dip-coated individually in sequence.

For example, the electrode leg(s) 1006 can be dipped into a polymeric solution, cured by UV or thermal radiation, dipped again into the polymeric solution, and cured again by UV or thermal radiation. The process can be repeated until the conductive cushioning material 2700 achieves a desired maximum cushion thickness 3100, cushion height 2900, or a combination thereof. For example, the electrode leg(s) 1006 can be dipped into the polymeric solution and cured by UV or thermal radiation between two times and ten times (e.g., 2 times, 3 times, 4 times, 5 times, 6 times, 7 times, 8 times, 9 times, and 10 times). The electrode leg(s) 1006 can also be dipped more than ten times.

The hydrogel can also be coupled to the one or more electrode legs 1006 by a mold-casting process or technique. For example, the one or more electrode legs 1006 can be placed into a mold prefabricated into a desired shape (bulbous- or ovoid-shaped) and the hydrogel can be allowed to form within the mold. The hydrogel can also be coupled to the one or more electrode legs 1006 by both mold-casting and dip-coating.

The hydrogel serving as the conductive cushioning material 2700 can absorb and retain a large amount of a conductor such as water comprising conductive ions. The hydrogel can also comprise a number of other conductors including ionic compounds (e.g., metal chlorides), carbon or carbon nanoparticles, and other conductive nanoparticles. The hydrogel can also be plasticized with a polyhydric alcohol such as glycerol or glycerin. For example, the hydrogel can comprise water, potassium chloride, and glycerin.

The hydrogel can be obtained by copolymerizing a mixture of monomeric acrylic acid with a glycolvinylether. The glycolvinylether can comprise at least one of hydroxybutyl vinyl ether ethyleneglycolvinylether, diethyleneglycolmonovinylether, and triethyleneglycolmethylvinylether. The hydrogel can also comprise a cross-linker or a cross-linking agent. The cross-linker can comprise at least one of methylene bisacrylamide, polyethylene glycol dimethacrylates and diacrylates, and ethoxylated trimethlolpropane triacrylate.

They hydrogel can also comprise a polyhydric alcohol to plasticize the cross-linked copolymers, absorb moisture, and promote the conductivity of the hydrogel. The polyhydric alcohol can comprise at least one of glycerol, sorbitol, and polyetheneglycol (PEG) and other polyhydroxyhydrocarbons and oxyalkyls.

The hydrogel can also comprise a thickening agent. The thickening agent can be a high molecular weight polymer or copolymer. The thickening agent can comprise at least one of a vinylacetate/N-vinylpyrrolidone copolymer, a maleic anhydride copolymer/methylvinylether, and an ethylene/maleic anhydride copolymer.

When the hydrogel is cured by UV radiation, the hydrogel or polymeric solution used to make the hydrogel can comprise a UV-sensitive curing agent. The UV-sensitive curing agent can comprise at least one of 2-hydroxy-2 methyl-1-phenyl-propan-2-one, 4-(2-hydroxyethoxy)phenyl (2-hydroxy-2-phenyl (2-hydroxy-2-propyl)ketone, 2,2-dimethoxy-2-phenyl acetophenone, 1-[4-(2-Hydroxyethoxy)-phenyl]-2-hydroxy-2-methyl-1-propane-1-one, and trimethyl benzoyl diphenyl phosphine oxide.

The hydrogel can also comprise additional buffers and neutralizing solutions including aluminum potassium sulfates, potassium sodium tartrates, hydrogen peroxide, hydroxyethylethylene urea, or a combination thereof.

The hydrogel can be non-residue forming such that the entire electrode tip 144 can be considered a "dry" electrode even though the electrode tip 144 provides the same signal quality as traditional "wet" electrodes requiring a wet conductive gel.

The conductive cushioning material 2700 can also be made of a soft conductive material capable of absorbing and retaining one or more conductors such as conductive ions or ionic compounds (e.g., potassium chloride), carbon, nanoparticles, or a combination thereof. For example, the conductive cushioning material 2700 can be a foam infused or saturated with the one or more conductors. The conductive cushioning material 2700 can also be an absorbent cotton padding infused or saturated with the one or more conductors. The conductive cushioning material 2700 can also be a sponge infused or saturated with the one or more conductors.

The electrode legs 1006 coated or covered by the conductive cushioning material 2700 can comprise or be made in part of a material stiffer or more rigid than the conductive cushioning material 2700. The electrode legs 1006 can comprise or be made in part of a material having a greater modulus of elasticity than the conductive cushioning material 2700. The conductive cushioning material 2700 can have a modulus of elasticity of between about 0.01 to about 0.50 Gigapascal (GPa). The electrode legs 1006 can have a modulus of elasticity of between about 1.0 GPa to about 220 GPa.

In addition to the electrode tips 144 disclosed herein, the conductive cushioning material 2700 can also be used to coat or cover any of the distal ends of electrodes and electrode tips described or depicted in any of U.S. Pat. Nos. 4,669,479, 4,967,038, 8,326,396, 9,237,857, U.S. patent application Ser. No. 12/517,664, and U.S. patent application Ser. No. 13/982,724, the contents of which are hereby incorporated by reference in their entireties.

Figure 33:
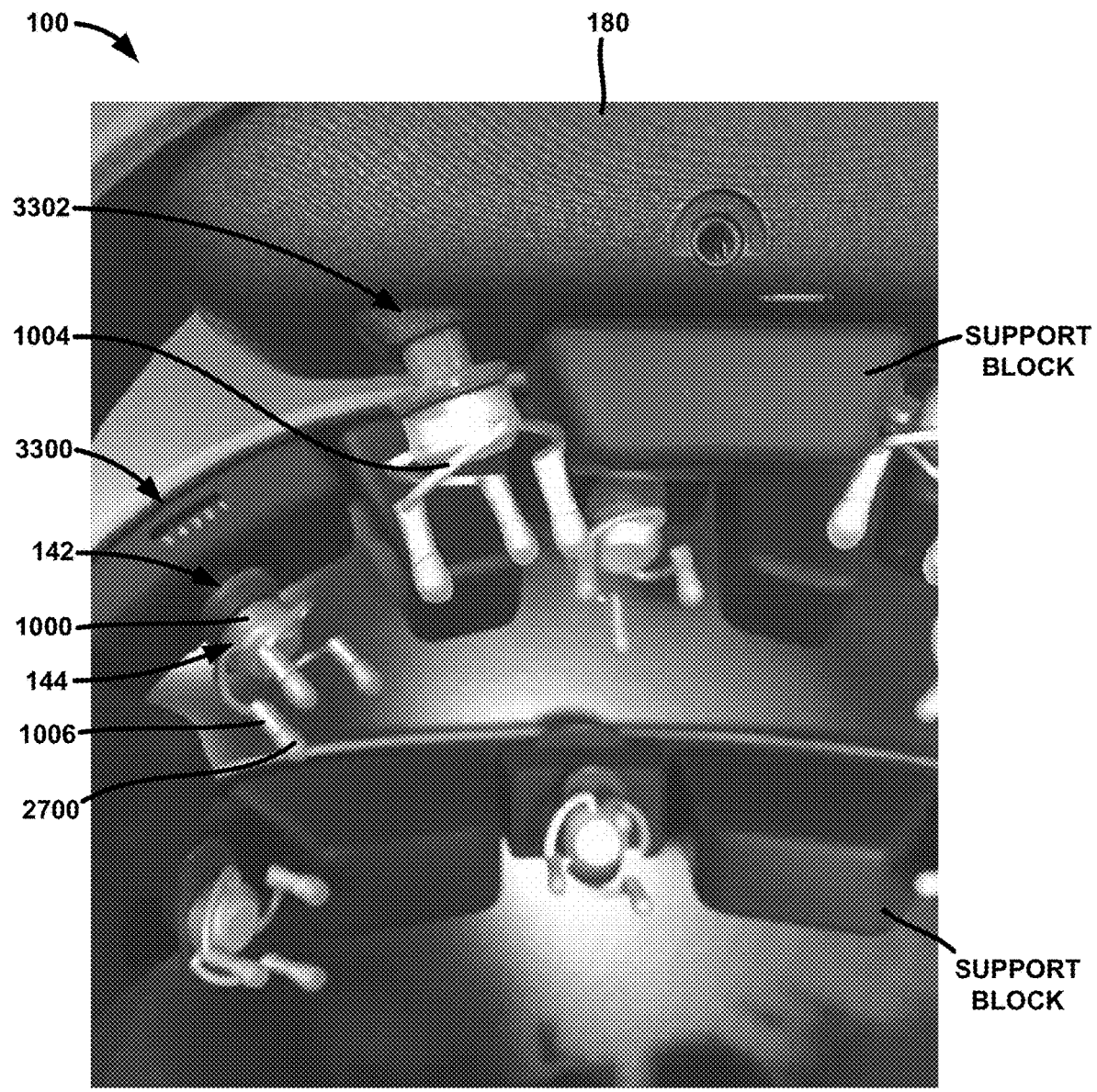
FIG. 33 is a black-and-white image showing a close-up view of a headset comprising detachable electrode tips having a conductive cushioning material coating the electrode legs of the electrode tips coupled to the headset.

FIG. 33 illustrates that the conductive cushioning material 2700 can coat or cover the electrode legs 1006 of the electrode tips 144 coupled to the electrode bodies 142 of the headset 100. As previously discussed, each of the electrodes coupled to the headset 100 can comprise an electrode body 142 comprising a first ferromagnetic component (e.g., the magnetic element 143, see FIG. 8) positioned at a distal end of the electrode body 142. The electrode tip 144 can comprise a second ferromagnetic component 2704 (see FIG. 27B or the ferrous element 148 of FIG. 8) configured to magnetically coupled to the first ferromagnetic component to attach the electrode tip 144 to the electrode body 142. The second ferromagnetic component 2704 can be encased within or coupled to an electrode tip body 1000 of the electrode tip 144.

The electrode tips 144 can be detachable such that any of the electrode tips 144 can be replaced with another electrode tip 144 of a different size (e.g., longer or shorter leg heights 1114), arm configuration, or cushion size or shape.

The one or more electrode legs 1006 can be coupled to the electrode tip body 1000. The electrode legs 1006 can be deflectable and have a non-biased configuration 2708 (see FIG. 27A) and a splayed configuration 2710 (see FIG. 27B). The electrode legs 1006 can be configured to spread out or fan out into the splayed configuration 2710 when the electrode is compressed. In other instances, the electrode legs 1006 can be configured to splay inwards into an inward splayed configuration when a compressive force is applied to the electrode tip body 1000 and the one or more electrode legs 1006. The electrodes can be compressed when the headset 100 is worn on a head of a patient and a number of straps coupled to the headset 100 (e.g., the chinstrap, the side-strap, etc.) are tightened.

The conductive cushioning material 2700 can be coupled to a segment of at least one of the electrode legs 1006. The conductive cushioning material 2700 can be infused or saturated with one or more conductors. The conductive cushioning material 2700 can absorb and retain the one or more conductors (e.g., water with conductive ions or ionic species and compounds) to maintain and enhance the conductivity of the electrode legs 1006.

FIG. 33 also illustrates that the electrode tips 144 comprising the conductive cushioning material 2700 coupled to the electrode legs 1006 of the electrode tips 144 can be coupled to an adjustable electrode 3300, a fixed electrode 3302, or a combination thereof. For example, the electrode tips 144 having the conductive cushioning material 2700 can be coupled to any of the adjustable electrodes shown in FIG. 6. Moreover, the electrode tips 144 having the conductive cushioning material 2700 can be coupled to any of the fixed electrodes shown in FIG. 6.

Figure 34A:
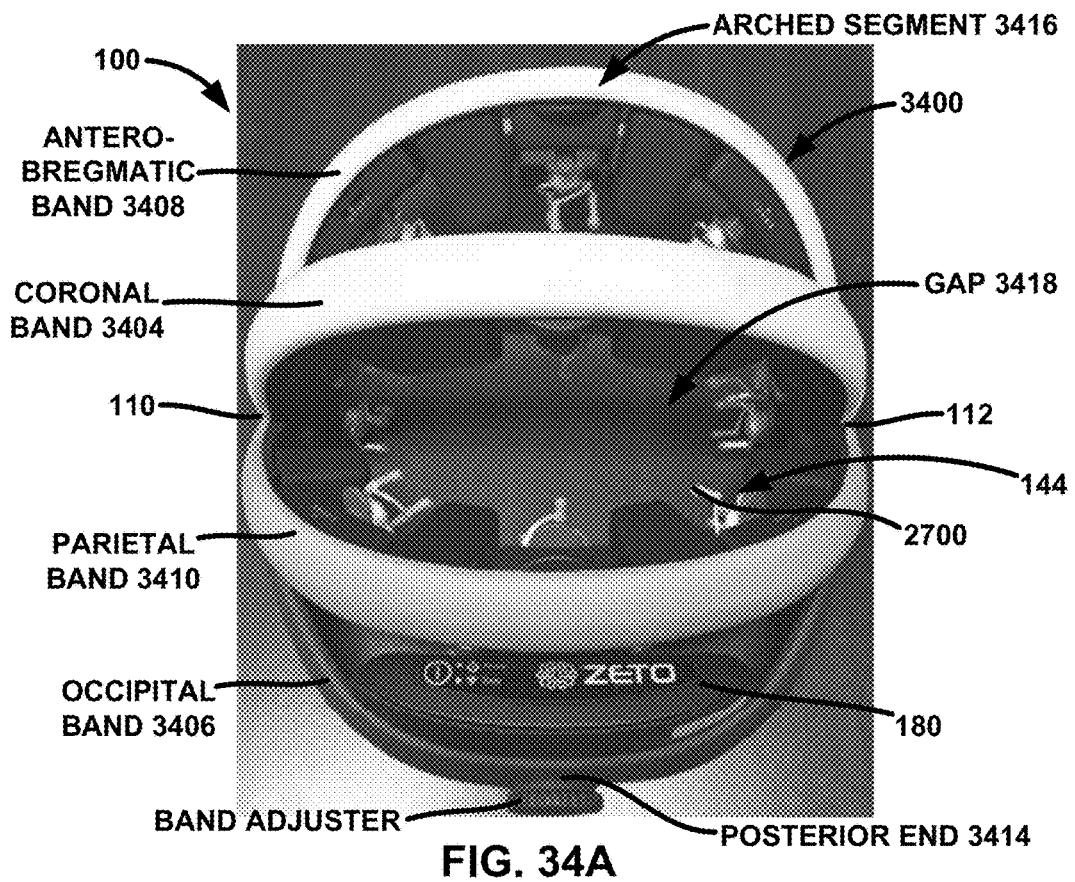
FIGS. 34A and 34B are black-and-white images showing top and bottom views, respectively, of a variation of a headset comprising detachable electrode tips having a conductive cushioning material coating the electrode legs of the electrode tip.
Figure 34B:
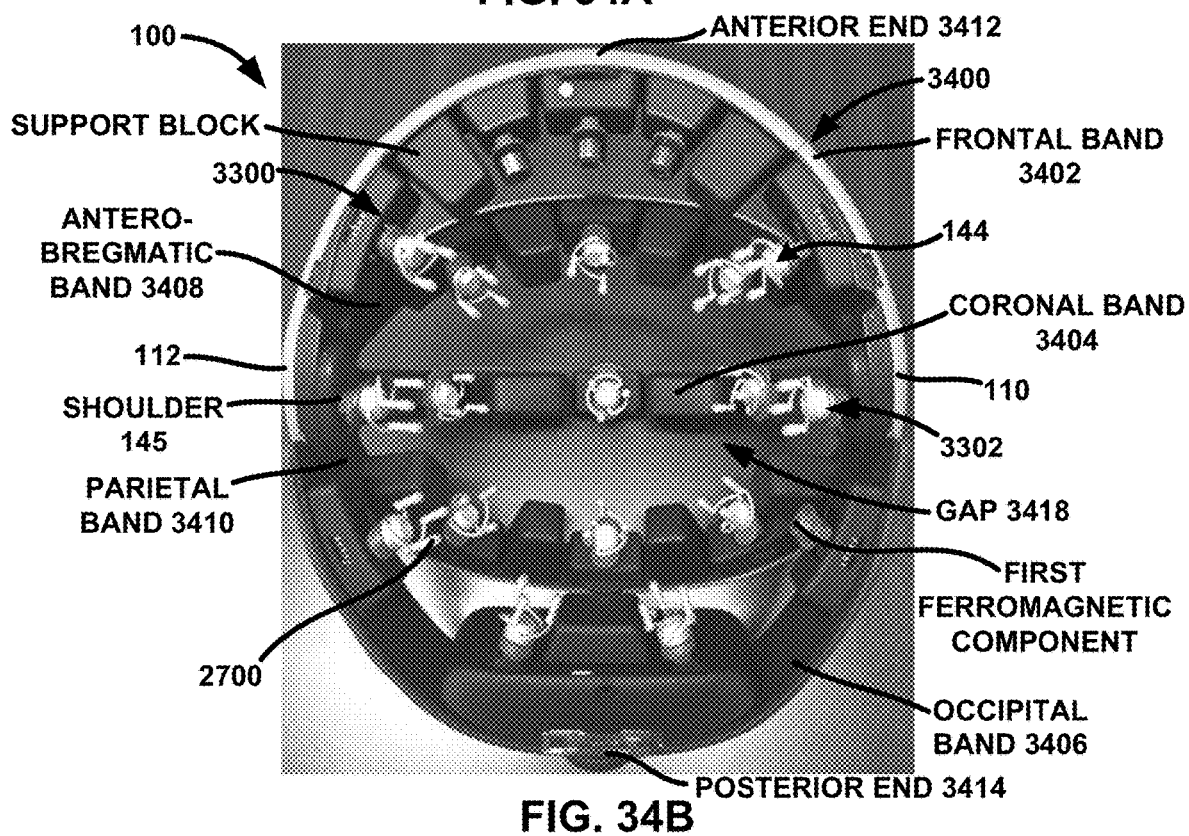

FIGS. 34A and 34B illustrate that electrode tips 144 comprising the conductive cushioning material 2700 coupled to the electrode legs 1006 of the electrode tips 144 can be coupled to any of the length-adjustable bands 3400 connecting the left junction 110 of the headset 100 with the right junction 112. As shown in FIGS. 34A-34B, the length adjustable bands 3400 can comprise a frontal band 3402, a coronal band 3404, an occipital band 3406, an antero-bregmatic band 3408, and a parietal band 3410.

The frontal band 3402 can be the length-adjustable band 3400 closest to an anterior end 3412 of the headset 100. The front band 3402 can also be the length-adjustable band 3400 closest to a nasion (i.e., the most anterior point of the frontonasal suture) of a patient/user when the headset 100 is worn on a head of the patient/user.

The coronal band 3404 can be the length-adjustable band 3400 positioned closest to the vertex of patient/user when the headset 100 is worn on the head of the patient/user. The vertex can be the highest point on the scalp of the patient/user. The occipital band 3406 can be the length-adjustable band 3400 positioned closest to a posterior end 3414 of the headset 100. The occipital band 3406 can also be the length-adjustable band 3400 positioned closest to an inion (i.e., the occipital protuberance) of the patient/user when the headset 100 is worn on the head of the patient/user.

The antero-bregmatic band 3408 can be the length-adjustable band 3400 positioned in between the frontal band 3402 and the coronal band 3404. The antero-bregmatic band 3408 can also be the length-adjustable band 3400 positioned slightly anterior to the bregma of the patient/user when the headset 100 is worn on the head of the patient/user. The parietal band 3410 can be the length-adjustable band 3400 positioned in between the coronal band 3404 and the occipital band 3406. The parietal band 3410 can also be the length-adjustable band 3400 spanning a posterior portion of the parietal bone of the patient/user when the headset 100 is worn on the head of the patient/user.

The electrode tip 144 comprising the conductive cushioning material 2700 can serve as the distal ends of any of the adjustable electrodes 3300 coupled to any of the frontal band 3402, the coronal band 3404, the occipital band 3406, the antero-bregmatic band 3408, and the parietal band 3410. The electrode tip 144 comprising the conductive cushioning material 2700 can serve as the distal ends of any of the fixed electrodes 3302 coupled to any of the frontal band 3402, the coronal band 3404, the occipital band 3406, the antero-bregmatic band 3408, and the parietal band 3410.

As shown in FIGS. 34A-34B, each of the length-adjustable bands 3400 can comprise an arched segment 3416. The arched segment 3416 of one of the length-adjustable bands 3400 can be separated from the arched segment 3416 of an immediately adjacent length-adjustable band 3400 by a gap 3418 or void space. This can allow each of the length-adjustable bands 3400 to have its own length adjusted without affecting the lengths of neighboring bands 3400, thereby enhancing the customizability of the headset 100 for different sized and shaped heads.

Figure 35A:
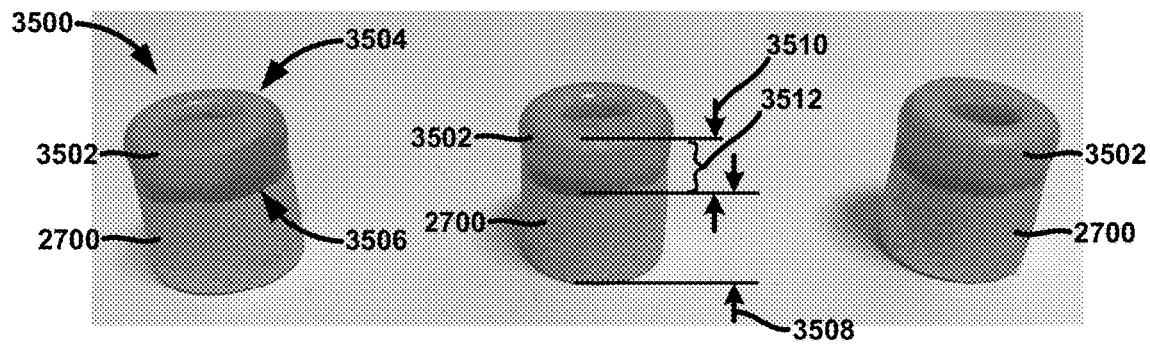
FIGS. 35A-35C are black-and-white images showing additional variations of an electrode tip having a substantially planar distal side coated or covered by a conductive cushioning material.
Figure 35B:
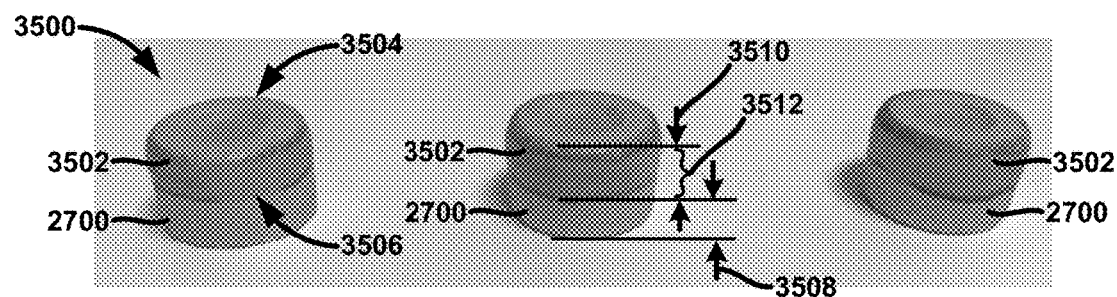
Figure 35C:
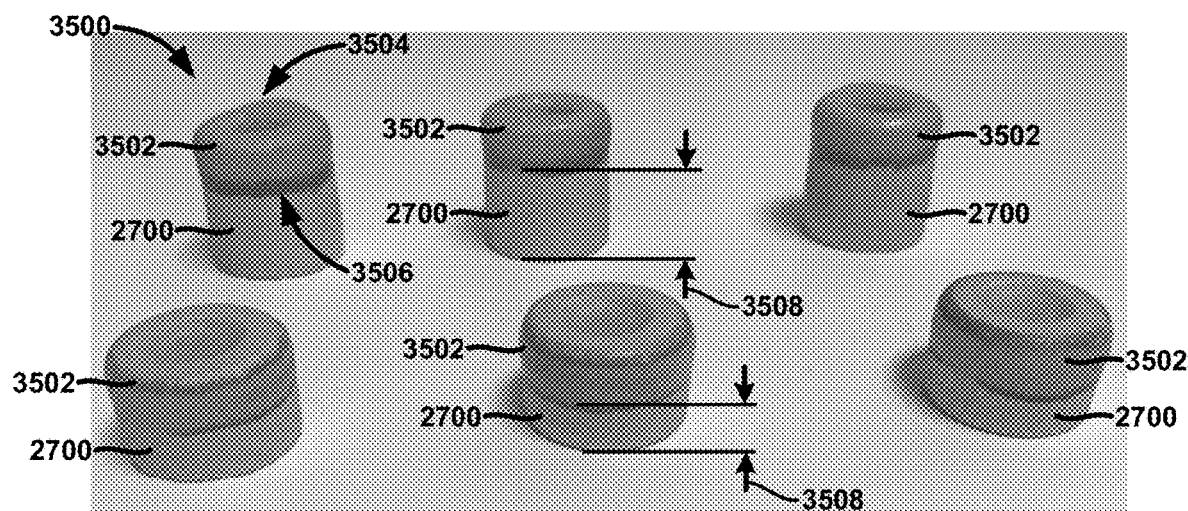

FIGS. 35A-35C illustrate additional variations of an electrode tip 3500 for sensing bioelectrical potential. The electrode tip 3500 can comprise an electrode tip body 3502 (similar to the electrode tip body 1000 described and depicted with respect to the electrode tip 144 previously described) comprising a proximal side 3504 and a substantially planar distal side 3506. The substantially planar distal side 3506 can be a substantially flat or level side or surface of the electrode tip body 3502. The conductive cushioning material 2700 can be coupled to or coated onto the distal side 3506. The conductive cushioning material 2700 can retain or be saturated with one or more conductors.

The conductive cushioning material 2700 can be a cured polymeric material. The one or more conductors can comprise at least one of carbon, metal chlorides, conductive ions, and conductive nanoparticles. The conductive cushioning material 2700 can be a hydrogel. The hydrogel can be coated on to the distal side 3506 by dip-coating, adhesives, or a combination thereof. The hydrogel can also be coupled to the distal side 3506 by mold casting, adhesives, or a combination thereof. For example, the hydrogel can be dip-coated by dipping a distal segment of the electrode tip body 3502 including the distal side 3506 into a polymeric solution and then cured by UV or thermal radiation. The distal segment of the electrode tip body 3502 can then be dipped again into the polymeric solution and cured again by UV or thermal radiation. The process can be repeated until the conductive cushioning material 2700 achieves a desired maximum cushion thickness, cushion height, or a combination thereof.

The hydrogel can be cured by ultraviolet (UV) radiation. The hydrogel can comprise glycerin. The hydrogel can be the same type of hydrogel (having the same composition) previously discussed.

The conductive cushioning material 2700 can also be a foam saturated or infused with the one or more conductors. Alternatively, the conductive cushioning material 2700 can be an absorbent cotton padding saturated or infused with the one or more conductors. The conductive cushioning material 2700 can also be a conductive sponge saturated or infused with the one or more conductors.

The conductive cushioning material 2700 can have a maximum thickness or cushion thickness. The cushion thickness can range from about 0.05 mm to about 2.5 mm as measured from an exterior surface of the electrode tip body 3502. The conductive cushioning material 2700 can be substantially cylindrical-shaped. The conductive cushioning material 2700 can also be substantially ovoid-shaped, spherical-shaped, hemispherical-shaped, cuboid-shaped, pyramidal-shaped, conical-shaped, and frustoconical-shaped. The conductive cushioning material 2700 can be non-residue-forming such that no residue is left on a skin surface of the patient after use.

The conductive cushioning material 2700 can have a cushion height 3508. As shown in FIG. 35A, the cushion height 3508 can be greater than a height dimension 3510 of an exposed segment 3512 of the electrode tip body 3502. The cushion height 3508 can also be less than a height dimension 3510 of the exposed segment 3512 of the electrode tip body 3502 as shown in FIG. 35B. FIG. 35C illustrates that the cushion height 3508 of the electrode tip 3500 can vary. For example, the cushion height 3508 can be between about 2.0 mm to about 10.0 mm (e.g., 5.0 mm). The cushion height 3508 can also be between about 10.0 mm and 20.0 mm. The cushion height 3508 can also be between about 2.0 mm and 40.0 mm. The cushion height 3508 can also be greater than 40.0 mm. When the conductive cushioning material 2700 is a hydrogel, the variation in the cushion height 3508 can be the result of the number of times the electrode tip body 3502 is dipped into a polymeric solution used to make the hydrogel.

Figure 36:
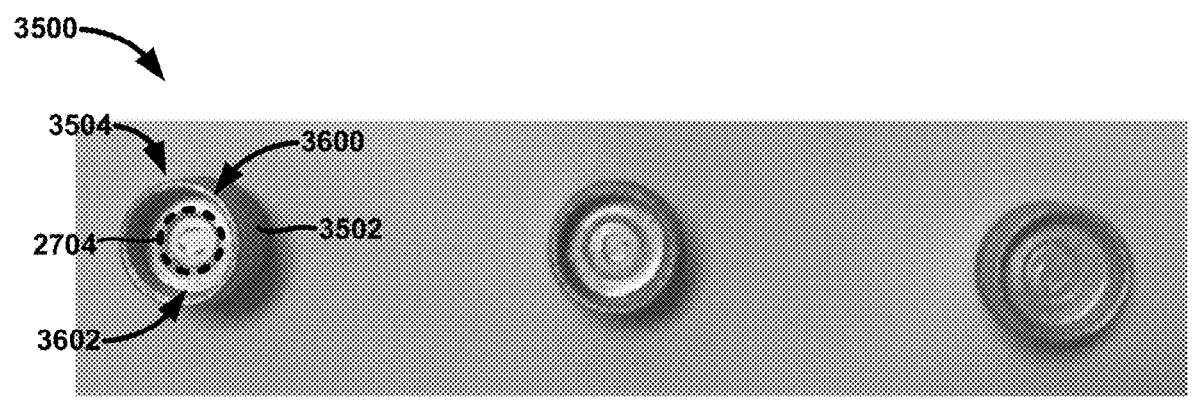
FIG. 36 is a black-and-white image showing a top plan view of a variation of an electrode tip having a substantially planar distal side coated or covered by a conductive cushioning material.

FIG. 36 illustrates that the electrode tip 3500 can comprise a second ferromagnetic component 2704 (represented using the circle in broken lines in FIG. 36). The second ferromagnetic component 2704 can be complementary to a first ferromagnetic component such that the first ferromagnetic component can magnetically couple to the second ferromagnetic component 2704 when the first ferromagnetic component is positioned or placed in proximity to the second ferromagnetic component 2704. The second ferromagnetic component 2704 can also refer to or be the same as the ferrous element 148 (see FIG. 8).

As previously discussed, an electrode body 142 of an electrode coupled to the headset 100 can comprise the first ferromagnetic component or a magnetic element 143 (see FIG. 8). The first ferromagnetic component can be positioned at a distal or terminal end of the electrode body 142. For example, the first ferromagnetic component can be positioned distal or beyond the shoulder 145 of the electrode. The first ferromagnetic component (e.g., the magnetic element 143) can be partially encased or surrounded by part of the electrode body 142. The first ferromagnetic component can be coupled to the electrode body 142 by adhesives (e.g., conductive adhesives), an interference fit, latches, clips, or a combination thereof.

The second ferromagnetic component 2704 can be encased within a portion of the electrode tip body 3502 of the electrode tip 3500 (similar to the electrode tip body 1000 of electrode tip 144). The electrode tip body 3502 of the electrode tip 3500 can comprise a cup-shaped portion 3600 defined along the proximal side 3504 of the electrode tip 3500 (the cup-shaped portion 3600 can be the same as the cup-shaped portion 2702 of electrode tip 144).

The second ferromagnetic component 2704 can be positioned or secured within part of a void 3602 of the electrode tip body 3502 and covered or sealed by additional material used to make the remainder of the electrode tip body 3502. For example, the second ferromagnetic component 2704 can be embedded or encased within the electrode tip body 3502 immediately below (i.e., vertically inferior to) the bottom of the void 3602. In other variations, the second ferromagnetic component 2704 can be visible and extend out from the void 3602, fill at least part of the void 3602, be coupled to the bottom of the cup-shaped portion 3600, or a combination thereof.

The electrode tip 3500 can detachably or removably couple to the electrode body 142 when the cup-shaped portion 3600 of the electrode tip body 3502 is pushed onto or otherwise biased toward the first ferromagnetic component. The void 3602 or hollow center defined by the cup-shaped portion 3600 can be configured to surround or cup over at least part of the first ferromagnetic component. By doing so, the second ferromagnetic component 2704 can be biased or brought closer to the first ferromagnetic component and the electrode tip 3500 can be magnetically coupled to the electrode body 142.

As previously discussed, the first ferromagnetic component can comprise or be made in part of a permanent magnet, an electropermanent magnet, a ferromagnetic metal or ferrous metal, or a combination thereof. The second ferromagnetic component 2704 can comprise or be made in part of a permanent magnet, an electropermanent magnet, a ferromagnetic metal or ferrous metal, or a combination thereof. For example, the first ferromagnetic component (e.g., the magnetic element 143) can be a permanent magnet and the second ferromagnetic component 2704 can be a ferromagnetic or ferrous metal configured to magnetically couple to the permanent magnet. Alternatively, the first ferromagnetic component can be a ferromagnetic or ferrous metal and the second ferromagnetic component 2704 can be a permanent magnet configured to magnetically couple to the ferromagnetic or ferrous metal. At least part of the electrode tip body 3502 can also be made of a ferromagnetic material.

The second ferromagnetic component 2704 can be sized to fit within the void 3602 defined by the cup-shaped portion 3600 of the electrode tip 3500. For example, the second ferromagnetic component 2704 can have a component diameter or width and the component diameter or width can be smaller than a tip body diameter of the electrode tip body 3502.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. An electrode tip for sensing bioelectrical potentials, comprising:
an electrode tip body;
electrode arms coupled to the electrode tip body; and
electrode legs coupled to the electrode arms,
wherein the electrode legs have a non-biased configuration and a splayed configuration, and
wherein the electrode legs are configured to translate into the splayed configuration when a compressive force is applied to the electrode tip body and the one or more electrode legs, wherein each of the electrode legs is an elongate rod having a leg diameter, wherein the electrode tip body is a cylindrical body having a tip body diameter, and wherein a ratio of the leg diameter to the tip body diameter is between 1:2 and 1:10.

2. The electrode tip of claim 1, wherein each of the electrode legs has a leg longitudinal axis, wherein the leg longitudinal axes of the electrode legs are parallel to one another when the electrode legs are in the non-biased configuration, and wherein the leg longitudinal axes of the electrode legs are non-parallel to one another when the electrode legs are in the splayed configuration.

3. The electrode tip of claim 1, wherein the electrode arms curve along a spiral pattern or trajectory such that each of the electrode arms curve in at least one of a clockwise or left-handed rotational direction and a counterclockwise or right-handed rotational direction.

4. The electrode tip of claim 1, wherein each of the electrode arms comprises a proximal arm end and a distal arm end, and wherein the distal arm end is planar or of the same vertical height as the proximal arm end.

5. The electrode tip of claim 1, wherein each of the electrode arms comprises a proximal arm end and a distal arm end, and wherein each of the electrode arms curves along a pitched or descending helical trajectory such that the distal arm end is vertically lower or below the proximal arm end.

6. The electrode tip of claim 1, further comprising lateral struts extending radially from the electrode tip body, wherein at least one of the lateral struts couple at least one of the electrode arms to the electrode tip body.

7. The electrode tip of claim 6, wherein the electrode tip body has a circular transverse cross-section, and wherein the lateral struts are coupled to the electrode tip body at positions arranged uniformly around a circumference of the electrode tip body.

8. The electrode tip of claim 1, wherein each of the electrode legs is an elongate rod having a leg diameter, a leg proximal end, and leg distal end, wherein each of the electrode legs is coupled to an electrode foot at the leg distal end.

9. The electrode tip of claim 8, wherein the electrode foot has a maximum foot diameter, and wherein the maximum foot diameter is greater than the leg diameter.

10. The electrode tip of claim 8, wherein the electrode foot is made in part of a solid conductive material.

11. Th electrode tip of claim 8, wherein each of the electrode legs has a leg height as measured from the leg proximal end to the leg distal end, wherein the electrode foot has a foot proximal end, a foot distal end, and a foot height as measured from the foot proximal end to the foot distal end, wherein the leg height is greater than the foot height.

12. The electrode tip of claim 11, wherein a ratio of the foot height to the leg height is between 1:1 and 1:10.

13. The electrode tip of claim 1, further comprising a ferromagnetic component coupled to the electrode tip body.

* * * * *